US010806423B2

(12) United States Patent
Sugihara et al.

(10) Patent No.: US 10,806,423 B2
(45) Date of Patent: Oct. 20, 2020

(54) X-RAY IMAGING APPARATUS AND X-RAY IMAGING METHOD

(71) Applicant: J. MORITA MANUFACTURING CORPORATION, Kyoto-Shi, Kyoto (JP)

(72) Inventors: Yoshito Sugihara, Kyoto (JP); Tomoyuki Sadakane, Kyoto (JP); Hideki Yoshikawa, Kyoto (JP)

(73) Assignee: J. MORITA MANUFACTURING CORPORATION, Kyoto (JP)

( * ) Notice: Subject to any disclaimer, the term of this patent is extended or adjusted under 35 U.S.C. 154(b) by 49 days.

(21) Appl. No.: 16/108,101

(22) Filed: Aug. 22, 2018

(65) Prior Publication Data

US 2019/0059842 A1 Feb. 28, 2019

(30) Foreign Application Priority Data

Aug. 23, 2017 (JP) .................................. 2017-160599

(51) Int. Cl.
*A61B 6/00* (2006.01)
*A61B 6/03* (2006.01)
(Continued)

(52) U.S. Cl.
CPC ............ *A61B 6/5282* (2013.01); *A61B 6/032* (2013.01); *A61B 6/035* (2013.01); *A61B 6/04* (2013.01);
(Continued)

(58) Field of Classification Search
CPC ......... A61B 6/5282; A61B 6/032; A61B 6/54; A61B 6/035; A61B 6/04; A61B 6/4085;
(Continued)

(56) References Cited

U.S. PATENT DOCUMENTS 4,741,007 A * 4/1988 Virta ........................ A61B 6/14
378/39
2006/0256921 A1* 11/2006 Tachibana ................ A61B 6/14
378/116
(Continued)

FOREIGN PATENT DOCUMENTS

| EP | 2156792 A1 | 2/2010 |
| EP | 2774540 A1 | 9/2014 |
| JP | 2006-288726 A | 10/2006 |

OTHER PUBLICATIONS

The Search Report from the corresponding European Patent Application No. 18189936.0 dated Feb. 12, 2019.

*Primary Examiner* — David P Porta
*Assistant Examiner* — Gisselle M Gutierrez
(74) *Attorney, Agent, or Firm* — Shinjyu Global IP

(57) ABSTRACT

An X-ray imaging apparatus receives mode selection using a mode selection receiving unit including a mode setting unit and an operation display. When a CT mode is selected by the mode selection receiving unit, an X-ray beam shape adjuster shapes an X-ray beam into an X-ray cone beam in which a center beam that is a center of the X-ray beam is orthogonally incident on a body axis of a head. When a panoramic mode is selected, the X-ray beam shape adjuster shapes the X-ray beam into an X-ray narrow beam in which the center beam is incident on the body axis from obliquely below to obliquely above, the X-ray narrow beam having a length in a direction of the body axis.

21 Claims, 35 Drawing Sheets

(51) Int. Cl.
  *A61B 6/04* (2006.01)
  *A61B 6/14* (2006.01)
  *A61B 6/06* (2006.01)
(52) U.S. Cl.
  CPC .................. *A61B 6/06* (2013.01); *A61B 6/14* (2013.01); *A61B 6/4085* (2013.01); *A61B 6/4225* (2013.01); *A61B 6/54* (2013.01)
(58) Field of Classification Search
  CPC ........... A61B 6/4225; A61B 6/14; A61B 6/06; A61B 6/0457
  USPC .......................................................... 378/19
  See application file for complete search history.

(56) References Cited

U.S. PATENT DOCUMENTS

| | | | |
|---|---|---|---|
| 2012/0307960 A1* | 12/2012 | Choi ..................... | A61B 6/545 378/4 |
| 2014/0126687 A1* | 5/2014 | Yoshikawa ............. | A61B 6/145 378/16 |
| 2014/0254745 A1* | 9/2014 | Nakai .................... | A61B 6/466 378/4 |
| 2015/0010126 A1* | 1/2015 | Rotondo ................ | A61B 6/032 378/19 |
| 2015/0117600 A1* | 4/2015 | Jun ........................ | A61B 6/14 378/39 |
| 2015/0164446 A1* | 6/2015 | Toimela .................. | A61B 6/14 378/39 |
| 2015/0374320 A1 | 12/2015 | Suuronen et al. | |
| 2016/0071238 A1* | 3/2016 | Kimura .............. | H04N 5/23238 348/36 |
| 2016/0199014 A1* | 7/2016 | Choi ....................... | A61B 6/14 378/39 |
| 2017/0245812 A1* | 8/2017 | Choi ....................... | A61B 6/00 |
| 2018/0310898 A1* | 11/2018 | Ahn ........................ | A61B 6/00 |
| 2019/0139272 A1* | 5/2019 | Pan ....................... | A61B 6/5258 |
| 2019/0307415 A1* | 10/2019 | Antikainen .............. | A61B 6/08 |

* cited by examiner

F I G. 6
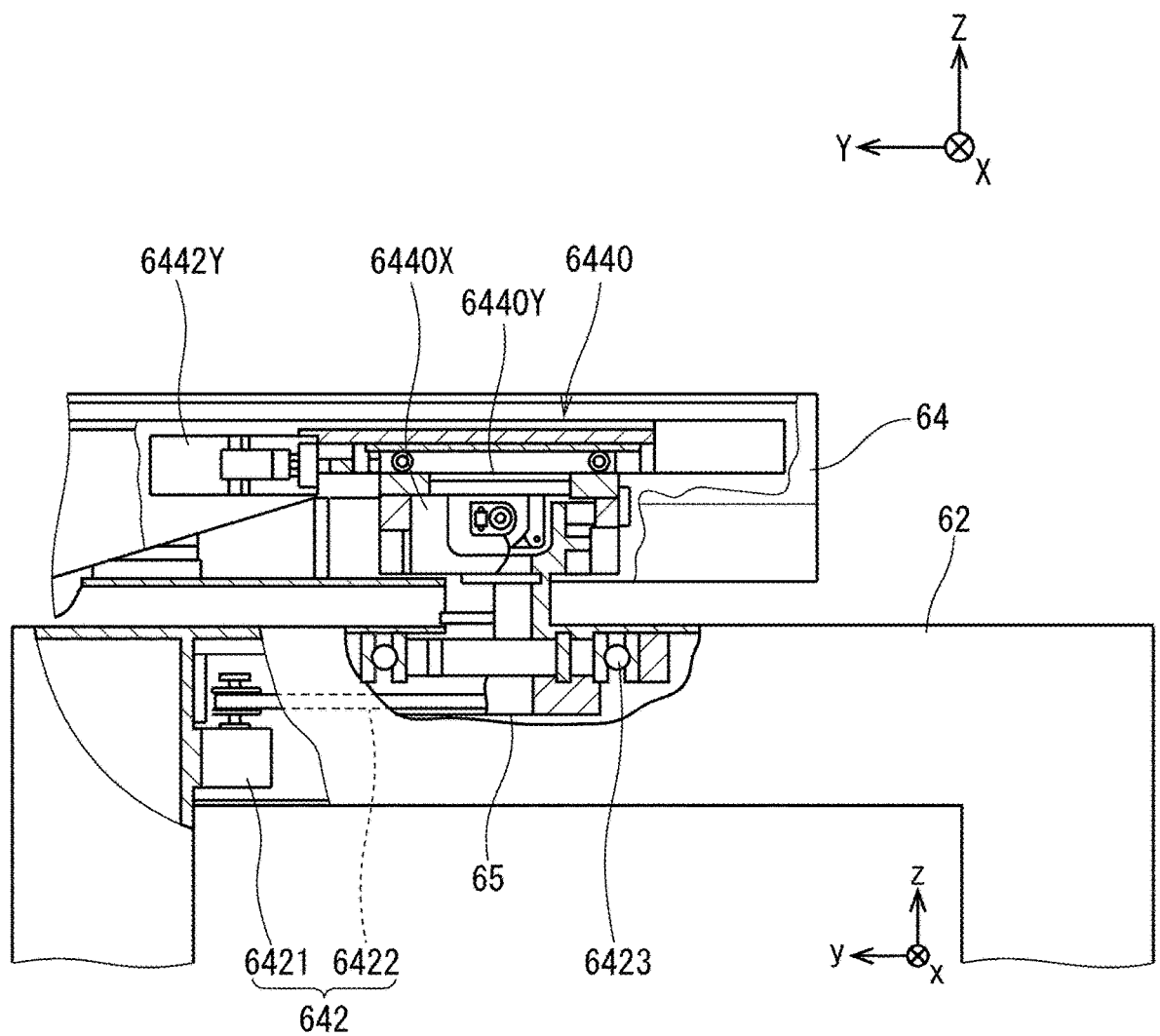

F I G. 3 2
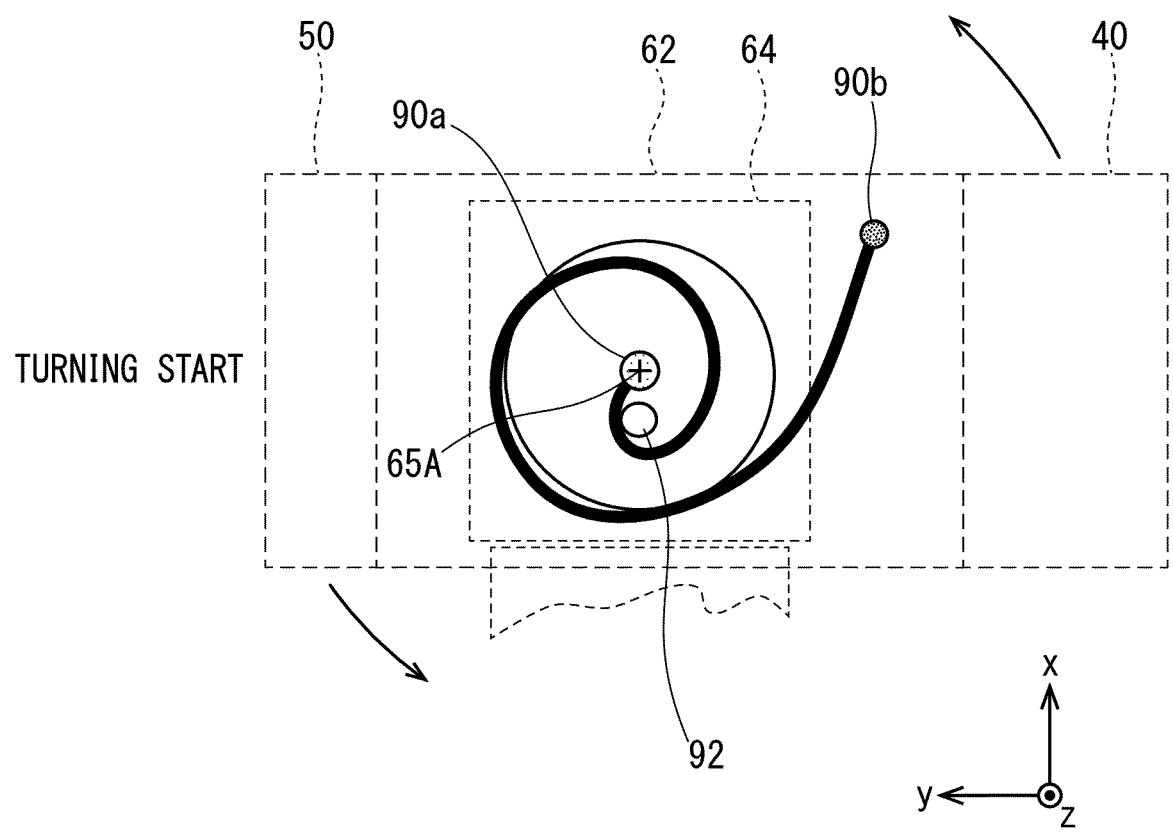

X-RAY IMAGING APPARATUS AND X-RAY IMAGING METHOD

CROSS-REFERENCE TO RELATED APPLICATIONS

This application claims priority to Japanese Patent Application No. 2017-160599 filed on Aug. 23, 2017. The entire disclosure of Japanese Patent Application No. 2017-160599 is hereby incorporated herein by reference.

TECHNICAL FIELD

Certain implementations relate to an X-ray imaging apparatus, particularly to a combination type X-ray imaging apparatus for panoramic imaging and CT imaging.

BACKGROUND

The combination type X-ray imaging apparatus capable of executing both the panoramic imaging for acquiring an image in which a section along a curved dental arch is developed in a plane and the CT imaging for acquiring a slice image of a region of interest is known in the field of dentistry and the like.

An X-ray generator and an X-ray image detector may be turned in an opposing state while a subject is sandwiched therebetween. An X-ray beam with which an imaging object is irradiated is shaped into a shape corresponding to various kinds of imaging by a slit disposed in front of an X-ray source. Specifically, the X-ray beam has a longitudinally elongated shape in the case of the panoramic imaging, and the X-ray beam has a fan beam shape spreading in a longitudinal direction and a crosswise direction in the case of the CT imaging. The X-ray generator and the X-ray detector are moved on an orbit for the panoramic imaging or the CT imaging.

SUMMARY

However, a shade obstacle that becomes an obstacle in a diagnosis may exist in a panoramic image acquired by typical panoramic imaging. For example, the shade obstacle is shades of a hard palate, a lower jaw corner, and a spine. For this reason, in the panoramic imaging, there is a demand for a technique of reducing the shade obstacle.

In the CT imaging, sometimes a radial artifact (metal artifact) is generated in a CT image when metal is included in the subject. When the metal artifact is generated, the shapes of the metal and its surroundings become obscure. For this reason, in the CT imaging, there is a demand for a technique of reducing an influence of the metal artifact on the CT image.

An object of certain implementations is to provide a technique capable of reducing the influence of shade obstacle in the panoramic imaging and the influence of the metal artifact in the CT imaging in the X-ray imaging apparatus capable of executing the panoramic imaging and the CT imaging.

Certain implementations are directed to an X-ray imaging apparatus.

In certain implementations, an X-ray imaging apparatus includes: an X-ray generator; an X-ray detector; a support that supports the X-ray generator and the X-ray detector while opposing the X-ray generator and the X-ray detector to each other; a turning driving unit that turns the X-ray generator and the X-ray detector, which are supported by the support; a head holder that holds a head of a subject; a mode setting receiving unit that receives selection of a mode among a plurality of modes including a panoramic mode in which a curved section corresponding to a dental arch is imaged and a CT mode in which a predetermined imaging region is imaged; and an X-ray beam shape adjuster that adjusts a shape of an X-ray beam emitted from the X-ray generator according to the mode of which the selection is received by the mode setting receiving unit. In the CT mode, the X-ray beam shape adjuster shapes an X-ray cone beam in which a center beam that is a center of the X-ray beam is incident orthogonally to a body axis of the head in the CT mode, and the X-ray beam shape adjuster shapes an X-ray narrow beam in which the center beam of the X-ray beam is incident upward from below with respect to the body axis, the X-ray narrow beam having a length in a direction of the body axis.

According to certain implementations, in the CT mode, the subject is irradiated with the X-ray cone beam in which the center beam is orthogonal to the body axis. In this case, a metal artifact and distortion can be reduced as compared with the case that the subject is irradiated with the X-ray cone beam in which the center beam is not orthogonal to the body axis. In the panoramic mode, the subject is irradiated with the X-ray narrow beam in which the center beam is incident on the body axis from obliquely below to obliquely above. In this case, the shade obstruct such as a hard palate on the panoramic image is reduced as compared with the case that the subject is irradiated with the X-ray narrow beam in which the center beam is orthogonal to the body axis. Consequently, image quality of the panoramic image can be expected to be improved.

Preferably, in the X-ray imaging apparatus, an SID (Source to Image receptor Distance) that is an interval between a generation point of the X-ray beam in the X-ray generator and a detection surface of the X-ray beam in the X-ray detector may range from 500 mm to 900 mm.

According to certain implementations, turning radii of the X-ray generator and X-ray detector necessary for panoramic imaging or CT imaging of the jaw of the human head can satisfactorily be ensured by setting the interval from the generation point of the X-ray beam to the detection surface to the range of 500 mm to 900 mm.

Preferably, the X-ray imaging apparatus may further include a magnification ratio changing mechanism that changes a magnification ratio by relatively moving the X-ray detector with respect to the head held by the head holder. The magnification ratio changing mechanism decreases the magnification ratio in the panoramic mode as compared with the magnification ratio in the CT mode.

According to certain implementations, resolution of the panoramic image can be improved by decreasing the magnification ratio during the panoramic imaging.

Preferably, the turning driving unit may rotate the support about a rotation axis line parallel to a vertical direction, the X-ray beam shape adjuster may shape the X-ray beam into the X-ray cone beam in which the center beam is incident in parallel to a horizontal direction in the CT mode, and the X-ray beam shape adjuster may shape the X-ray beam into the X-ray narrow beam in which the center beam is incident upward from below with respect to the horizontal direction in the panoramic mode.

According to certain implementations, in the CT mode, the head is irradiated with the X-ray cone beam in which the center beam is perpendicularly incident on the body axis. In this case, the metal artifact and the distortion can be reduced as compared with the case that the head is irradiated with the X-ray cone beam in which the center beam is obliquely incident on the body axis. In the panoramic mode, the head is irradiated with the X-ray narrow beam in which the center beam is incident on the body axis from obliquely below to obliquely above. In this case, the shade obstacle such as the hard palate on the panoramic image is reduced as compared with the case that the head is irradiated with the X-ray narrow beam in which the center beam is orthogonal to the body axis. Consequently, image quality of the panoramic image can be expected to be improved.

Preferably, hb=(SID/m)tan θ and 15<hb<65 is satisfied with respect to the X-ray narrow beam formed in the panoramic mode, where the curved section imaged in panoramic mode is a panoramic section, hb is a distance between a point on the panoramic section through which the center beam and a point on the panoramic section through which a horizontal line extending from an generation point of the X-ray narrow beam, SID is an interval between the generation point of said X-ray beam in the X-ray generator and a detection surface of the X-ray beam in the X-ray detector, m is a magnification ratio, and θ is an angle formed between the center beam and the horizontal direction.

According to certain implementations, a height dimension (=(SID/m)tan θ) from a position through which the center beam of the X-ray narrow beam passes to a position through which the X-ray perpendicularly incident on the X-ray detection surface passes can fall within the range of 15 mm to 60 mm. This enables the panoramic section to include from a tip of the jaw to the hard palate.

Preferably, the X-ray imaging apparatus may further include: a support post rising in the vertical direction; and a vertical movement driving unit that independently and vertically moves the support and the head holder along the support post.

According to certain implementations, the head can vertically be moved with respect to the X-ray generator by vertically moving the head holder. The X-ray generator can vertically be moved with respect to the head by vertically moving the support. Consequently, the shooting-up irradiation during the panoramic imaging and horizontal irradiation during the CT imaging can easily be performed.

Preferably, the vertical movement driving unit may position the support in the CT mode onto a vertically upper side than the support in the panoramic mode.

According to certain implementations, the X-ray cone beam can horizontally be output by locating the support in the upper side in the CT mode.

Preferably, the X-ray imaging apparatus may further include an X-ray generator vertically moving driving unit that vertically moves the X-ray generator with respect to the support.

Preferably, the X-ray imaging apparatus may further include: a bracket that suspends and supports the support and moves vertically using an elevating unit; and an electric cable that is routed from the bracket to an inside of the support through an opening formed in an upper portion of the support. The electric cable is accommodated into a spiral shape inside the support.

According to certain implementations, the support rotates in the opposite direction to the winding direction of the spiral of the electric cable with respect to the bracket, which allows shortage of the electric cable to be prevented. The electric cable is wound in the spiral shape when the support returns to an initial position, so that a surplus portion of the electric cable can be prevented from obstructing the rotation of the support.

Preferably, the X-ray imaging apparatus may further include: an arm extending horizontally from the bracket; and a cephalographic imaging head fixing unit that is provided at a distal end of the arm to fix the head.

According to certain implementations, the cephalographic imaging (head standard X-ray imaging) can be executed while the head is properly fixed.

Preferably, the CT mode may include a mode in which the turning driving unit rotates the X-ray generator and the X-ray detector by 360 degrees and a mode in which the turning driving unit rotates the X-ray generator and the X-ray detector by 180 degrees.

According to certain implementations, the CT imaging can selectively be executed at rotation angles of 180 degrees and 360 degrees.

Preferably, the plurality of modes may include an entire jaw panoramic mode in which an entire jaw is set to be an imaging object and a partial panoramic mode in which a part of the entire jaw is set to be the imaging object.

According to certain implementations, in the partial panoramic mode, a part of the entire jaw is restrictively irradiated with the X-ray, so that an exposure dose of the subject can be reduced.

Preferably, the vertical movement driving unit may adjust a height position of the support with respect to the head holder such that the center beam is incident on an occlusal position of an upper jaw and a lower jaw of a front tooth or a position below the occlusal position when the subject is irradiated with the X-ray cone beam during pre-imaging introduction of the subject in the CT mode.

According to certain implementations, before the imaging region is set, the height of the support is adjusted such that the center beam passes through a front-tooth occlusal position. The support is moved up and down according to the position of the subsequently-set imaging region. In dental practice, the center of the imaging region is often set around the front-tooth occlusal position. Consequently, the height of the support can efficiently be adjusted according to the subsequently-set imaging region by previously adjusting the support to the height at which the center beam passes through the occlusal position Preferably, the X-ray imaging apparatus may further include an X-ray detector vertically moving driving unit that vertically moves the X-ray detector with respect to the support. The CT mode includes a large irradiation field CT mode having a relatively large imaging region and a small irradiation field CT mode having a relatively small imaging region, and the X-ray detector vertically moving driving unit lowers the X-ray detector in the large irradiation field CT mode as compared with the small irradiation field CT mode.

Certain implementations are directed to an X-ray imaging method.

According to certain implementations, an X-ray imaging method includes: (a) a step of holding a head of a subject by a head holder; (b) a step of turning around the head an X-ray generator and an X-ray detector that are supported by a support while opposing the X-ray generator and the X-ray detector to each other; (c) a step of detecting an X-ray beam emitted from the X-ray generator using the X-ray detector in the step (b); (d) a step of receiving selection of a mode from a plurality of modes including a panoramic mode in which a curved section corresponding to a dental arch is imaged and a CT mode in which a predetermined imaging region is imaged; and (e) a step of adjusting a shape of the X-ray beam emitted from the X-ray generator in the step (c) by an X-ray beam shape adjuster according to the mode of which the selection is received in the step (d). In the CT mode, the X-ray beam shape adjuster forms an X-ray cone beam in which a center beam that is a center of the X-ray beam is incident orthogonally to a body axis of the head in the CT mode, and the X-ray beam shape adjuster forms an X-ray narrow beam in which a center beam that is a center of the X-ray beam is incident upward from below with respect to the body axis, the X-ray narrow beam having a length in a direction of the body axis.

These and other objects, features, aspects and advantages will become more apparent from the following detailed description when taken in conjunction with the accompanying drawings.

BRIEF DESCRIPTION OF THE DRAWINGS

FIGS. 5 and 6 are schematic plan views illustrating an upper frame 64 of the first preferred embodiment;

FIGS. 32 to 34 are plan views illustrating the electric cable 90 in the turning arm 62 during rotation.

DETAILED DESCRIPTION

Figure 1:
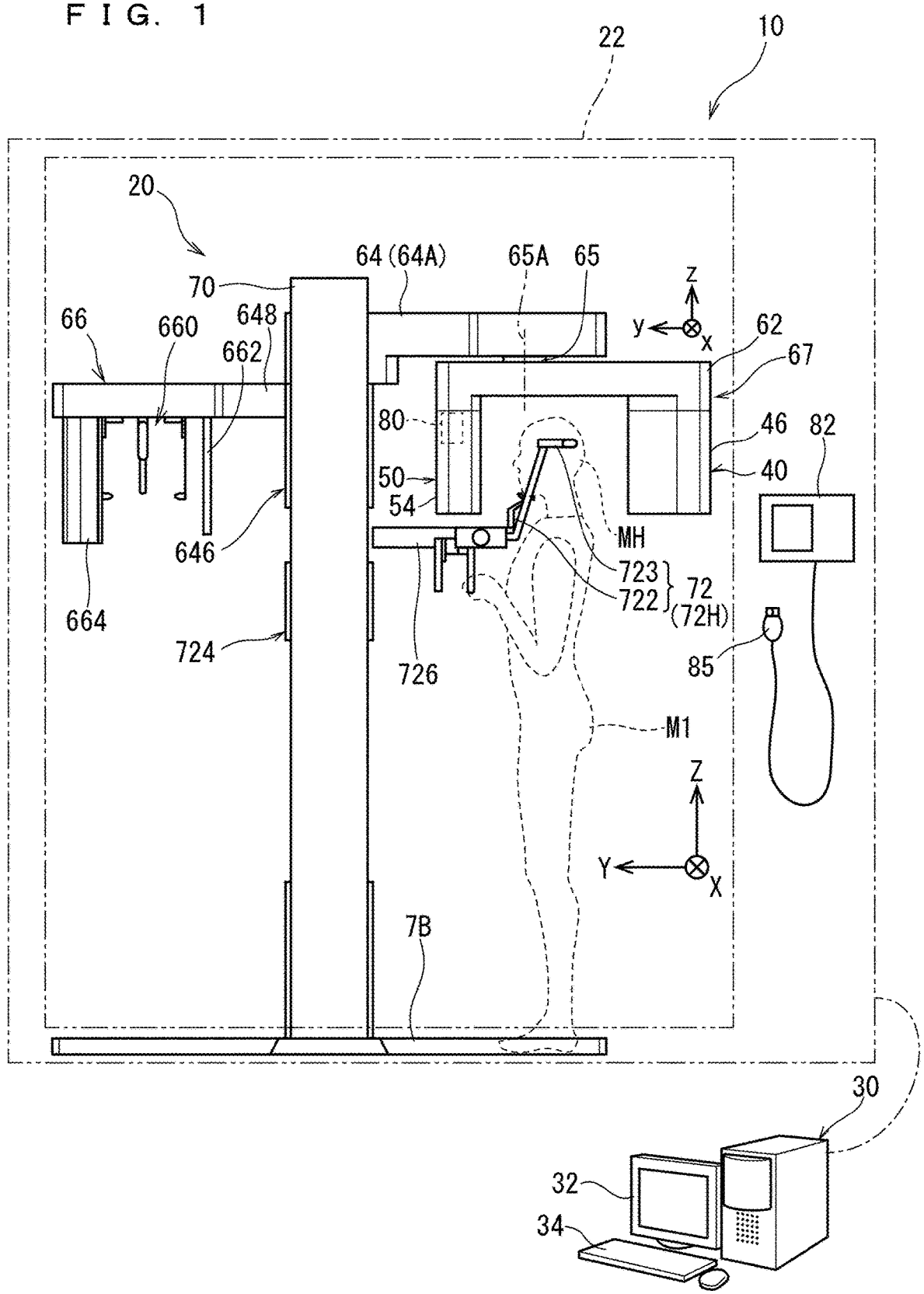
FIG. 1 is a general view illustrating a configuration of an X-ray imaging apparatus 10 according to a first preferred embodiment.

Hereinafter, preferred embodiments of the present invention will be described with reference to the accompanying drawings. Constituent elements described in the preferred embodiments are merely examples, but the scope of the present invention is not limited to the constituent elements of the preferred embodiments. In the drawings, for ease of understanding, sometimes dimensions and the number of each portion may be exaggerated or simplified as necessary.

As used throughout this disclosure, the singular forms "a," "an," and "the" include plural reference unless the context clearly dictates otherwise. Thus, for example, a reference to "a composition" includes a plurality of such compositions, as well as a single composition.

1. First Preferred Embodiment

Figure 2:
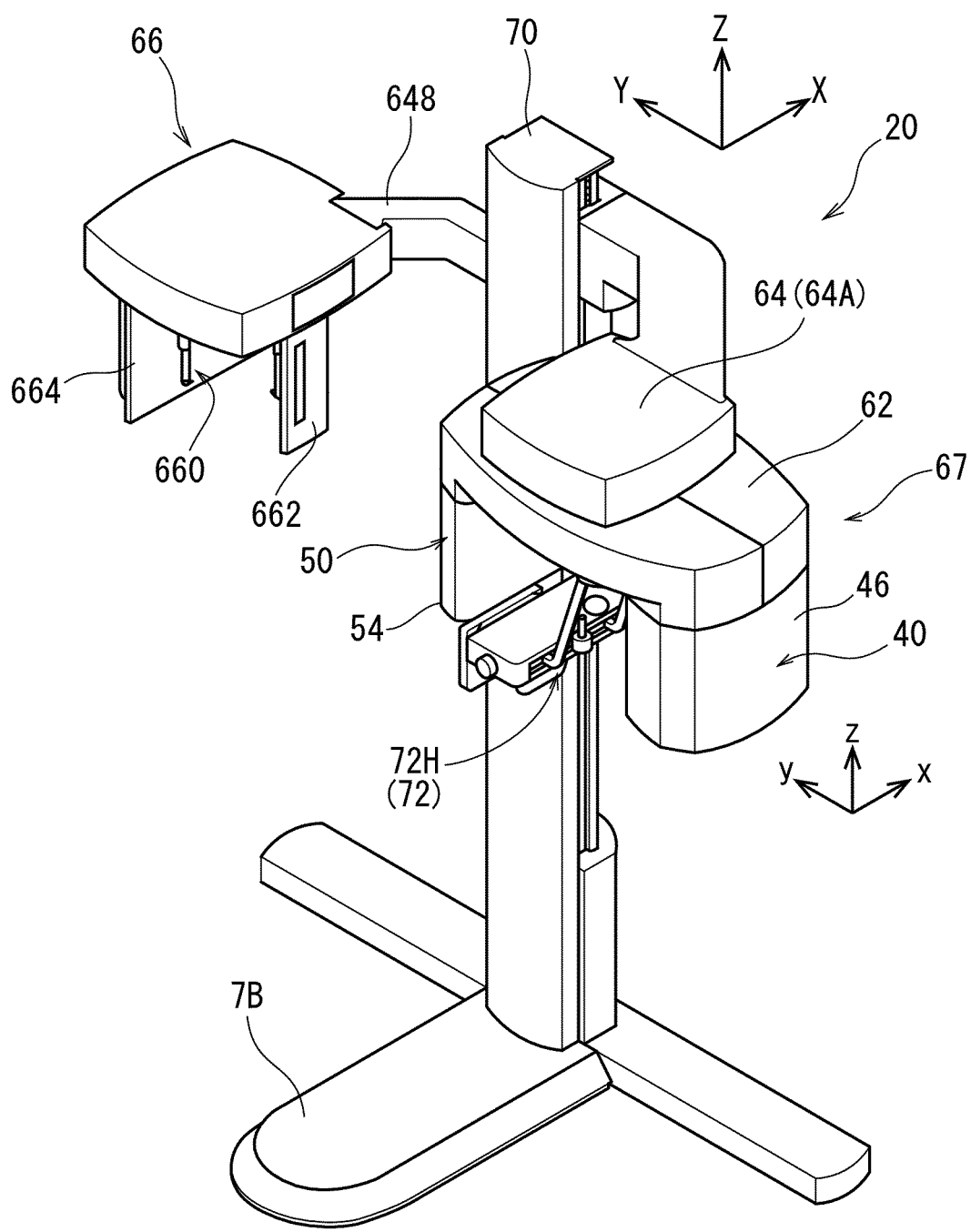
FIG. 2 is a perspective view illustrating an imaging unit 20 of the first preferred embodiment when the imaging unit 20 is viewed from obliquely above.
Figure 3:
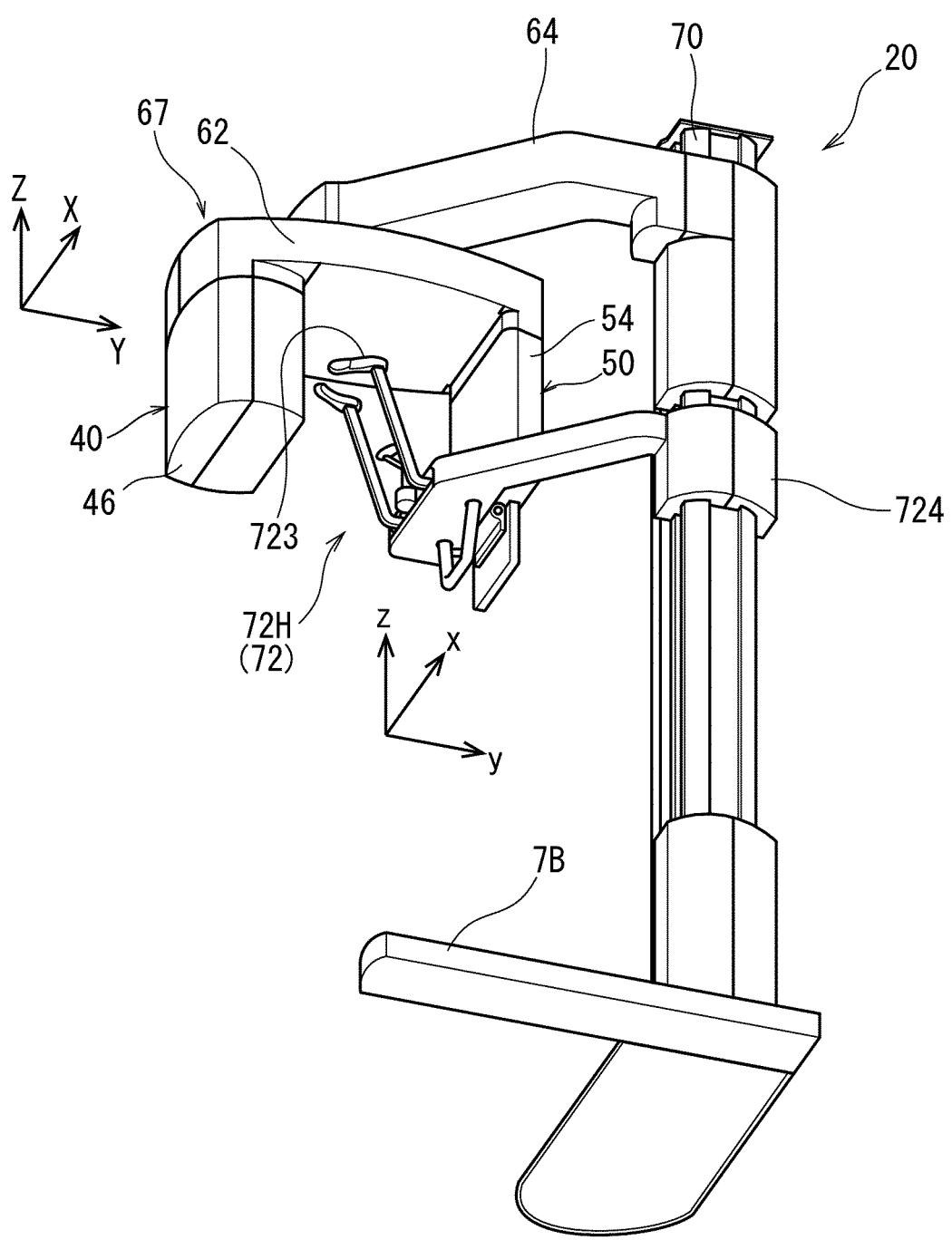
FIG. 3 is a perspective view illustrating the imaging unit 20 of the first preferred embodiment when the imaging unit 20 is viewed obliquely from below.
Figure 4:
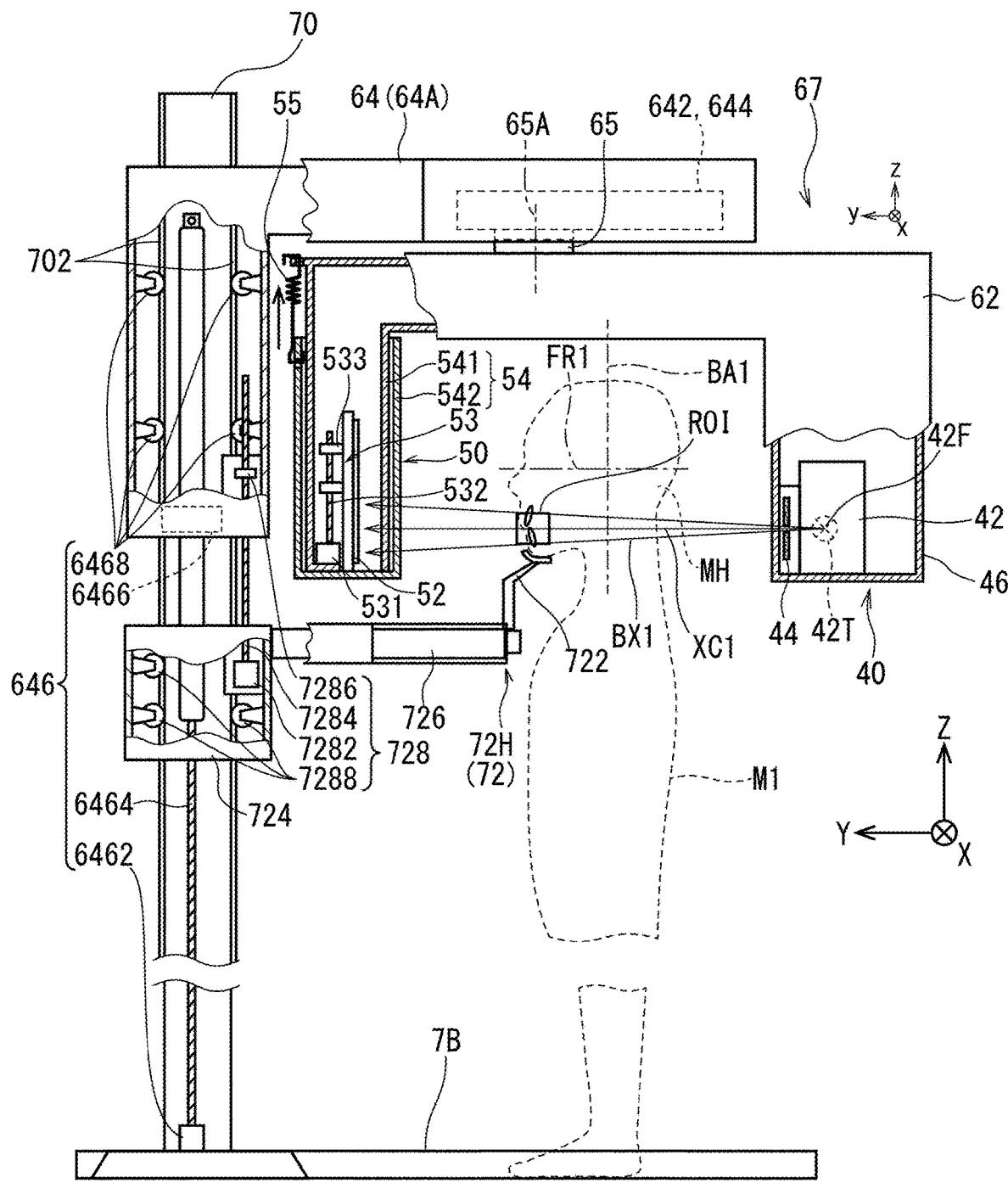
FIG. 4 is a schematic side view illustrating the imaging unit 20 of the first preferred embodiment.

FIG. 1 is a general view illustrating a configuration of an X-ray imaging apparatus 10 according to a first preferred embodiment. FIG. 2 is a perspective view illustrating an imaging unit 20 of the first preferred embodiment when the imaging unit 20 is viewed from obliquely above. FIG. 3 is a perspective view illustrating the imaging unit 20 of the first preferred embodiment when the imaging unit 20 is viewed obliquely from below. In FIG. 3, a cephalographic unit 66 is eliminated. FIG. 4 is a schematic side view illustrating the imaging unit 20 of the first preferred embodiment in which the cephalographic unit 66 is eliminated as in FIG. 3.

Figure 5:
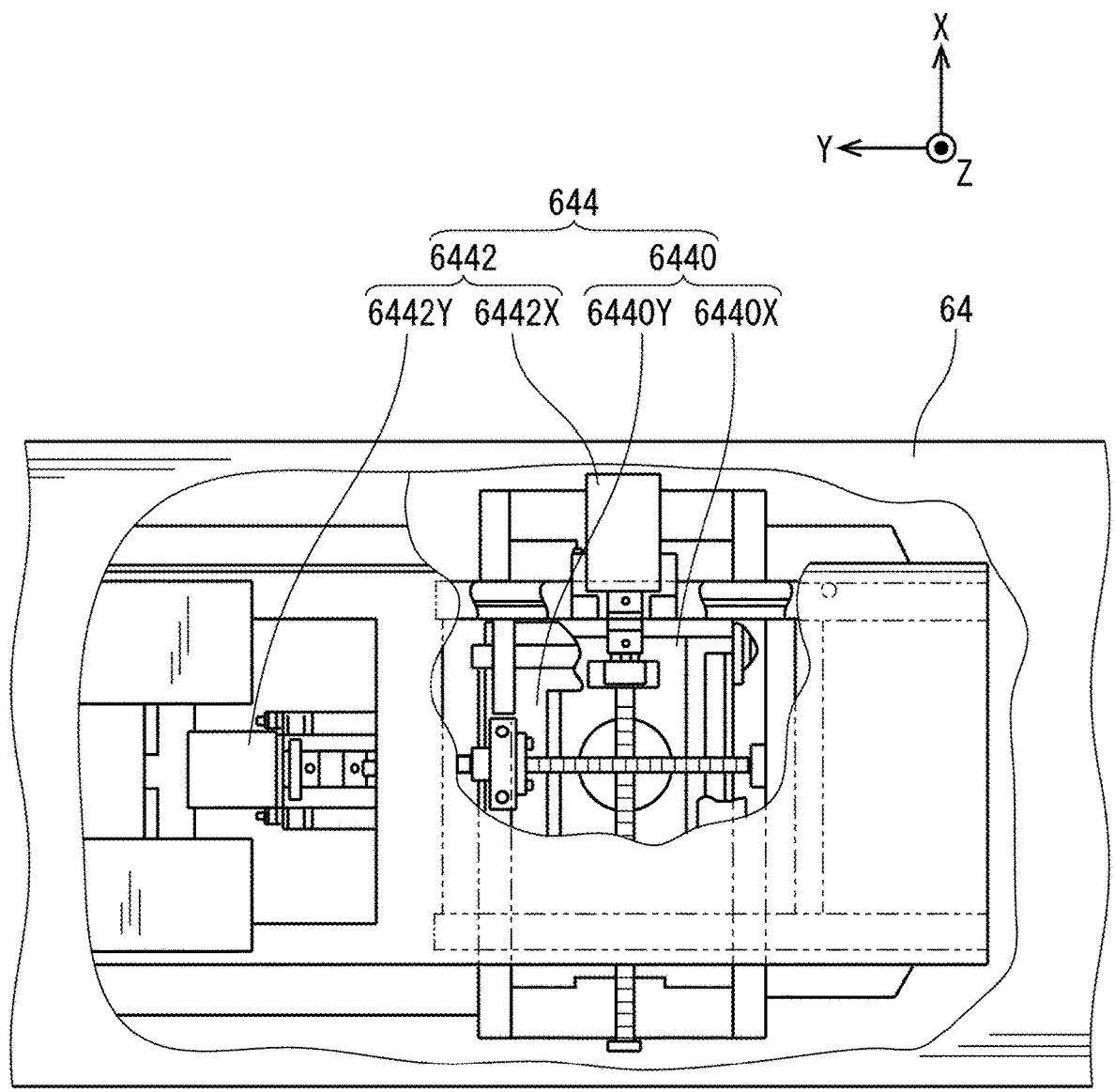
Figure 7:
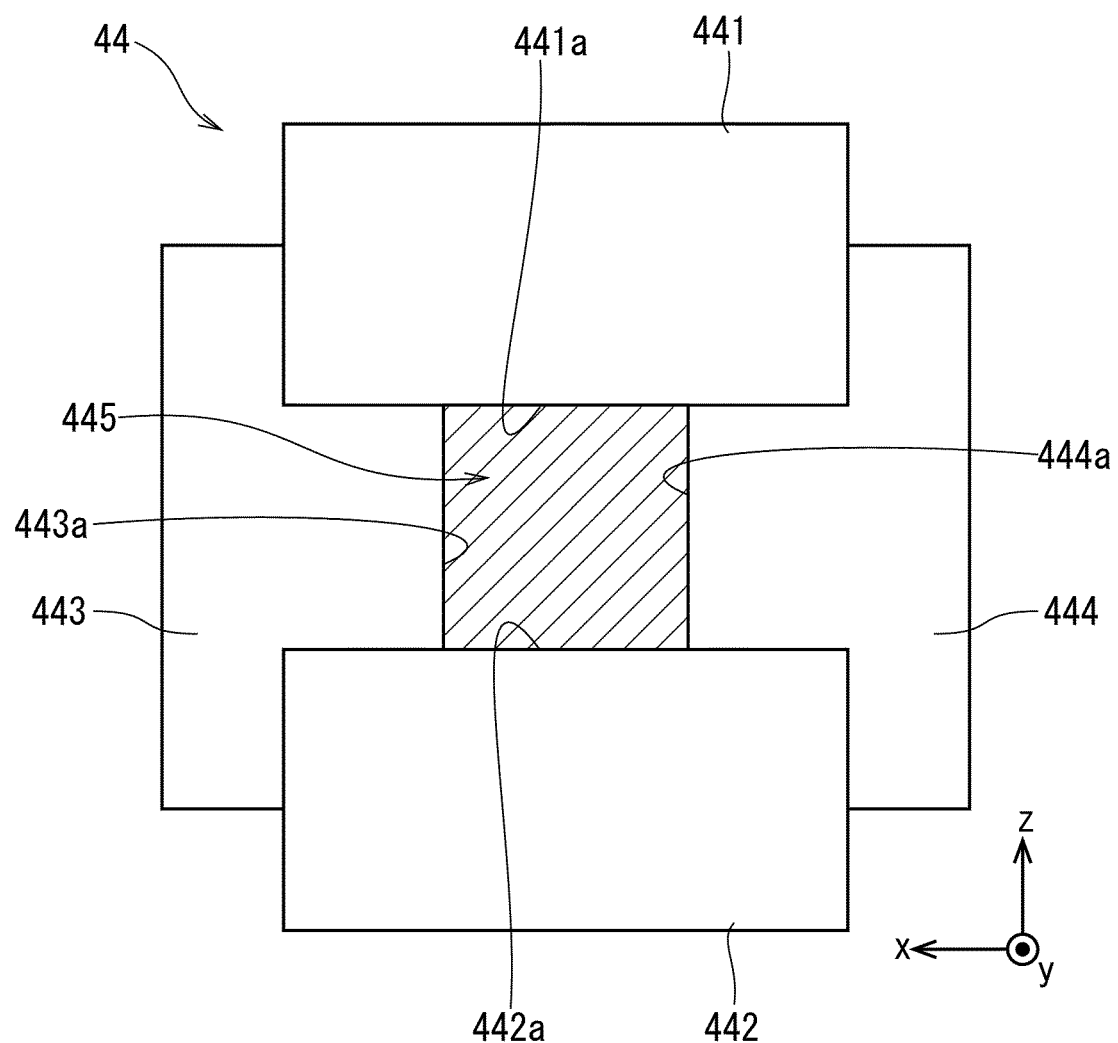
FIGS. 7 to 9 are schematic front views illustrating an X-ray beam shape adjuster 44 of the first preferred embodiment.
Figure 8:
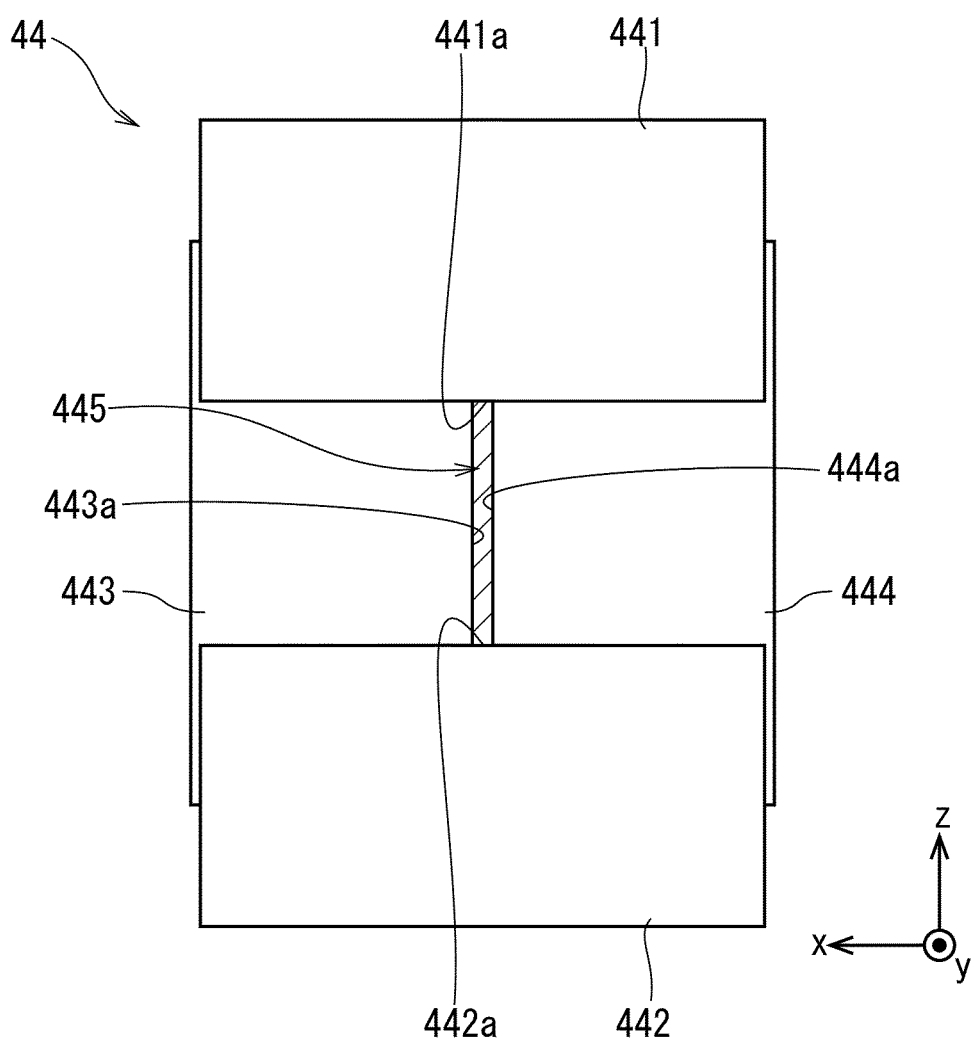
Figure 9:
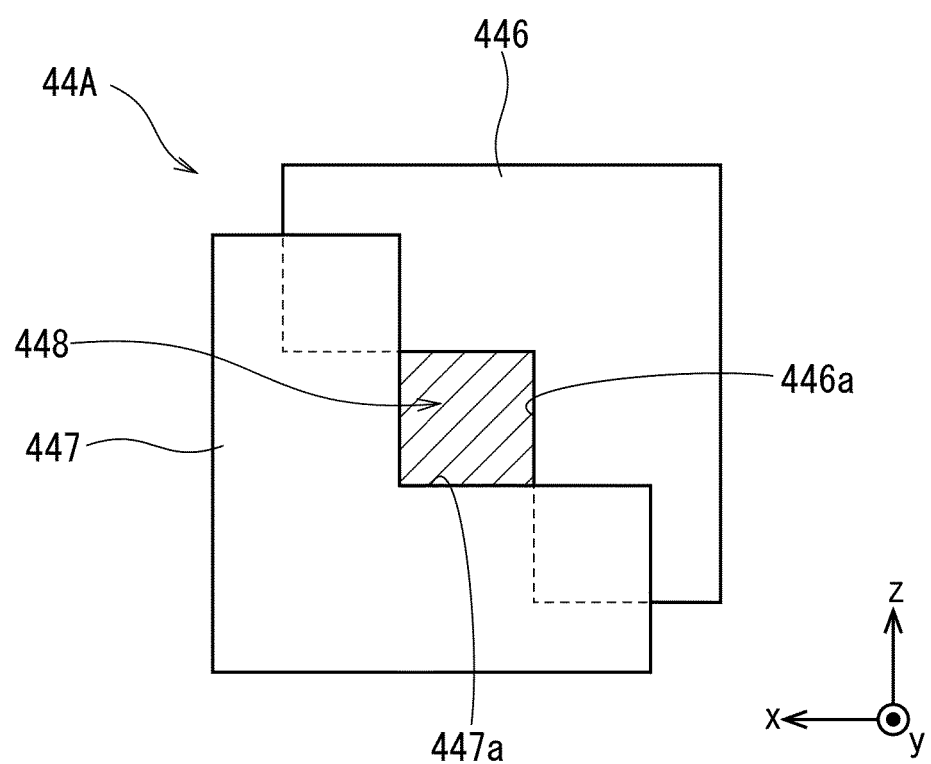
Figure 10:
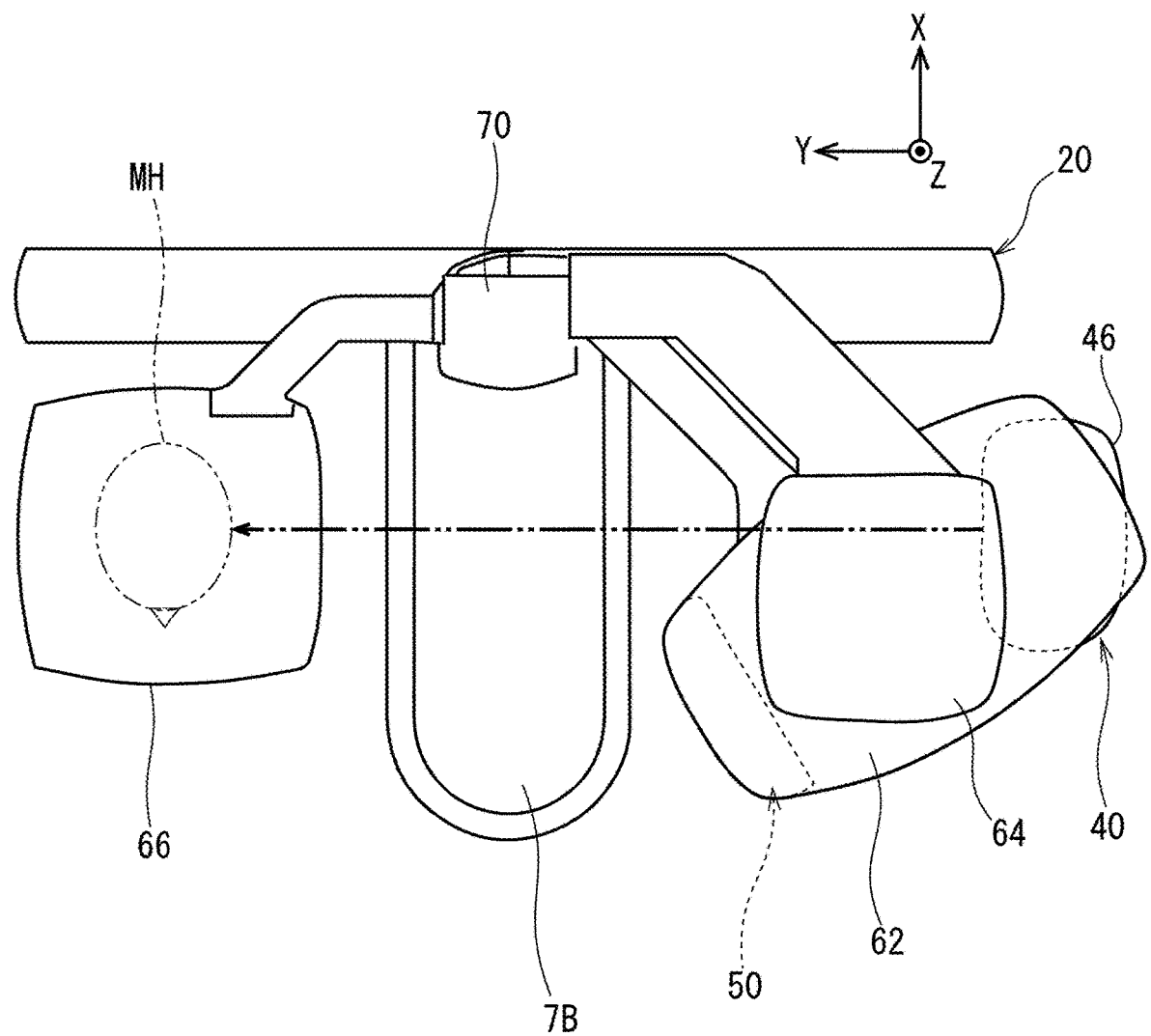
FIG. 10 is a plan view illustrating an X-ray irradiation path during cephalographic imaging of the first preferred embodiment.
Figure 11:
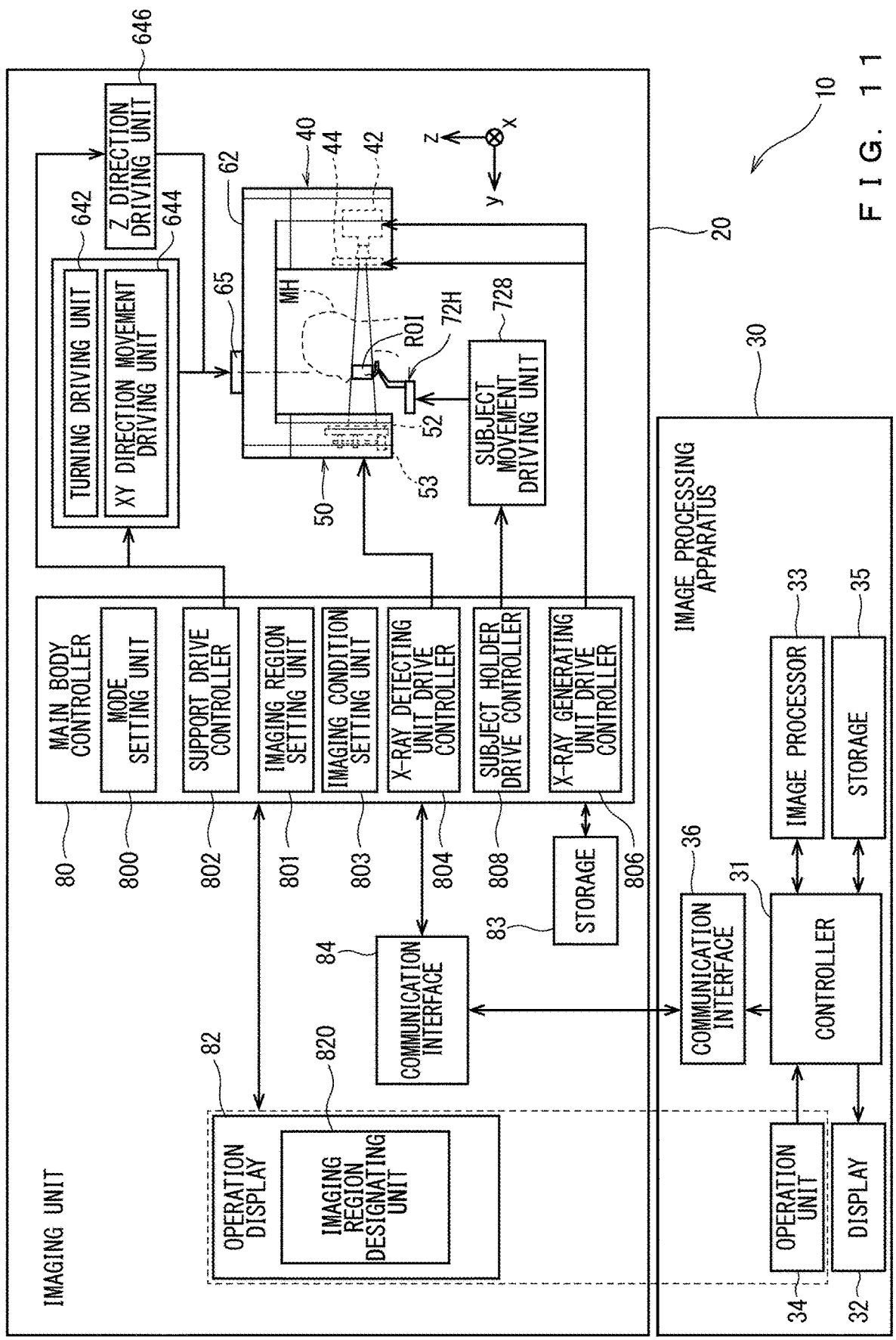
FIG. 11 is a block diagram illustrating a configuration of the X-ray imaging apparatus 10 of the first preferred embodiment.

FIG. 5 is a schematic plan view illustrating an upper frame 64 of the first preferred embodiment. FIG. 6 is a schematic side view illustrating the upper frame 64 of the first preferred embodiment. FIG. 7 is a schematic front view illustrating an X-ray beam shape adjuster 44 of the first preferred embodiment (during large irradiation field CT imaging (to be described later)). FIG. 8 is a schematic front view illustrating the X-ray beam shape adjuster 44 of the first preferred embodiment (during panorama imaging (to be described later)). FIG. 9 is a schematic front view illustrating the X-ray beam shape adjuster 44 of the first preferred embodiment (during small irradiation field CT imaging (to be described later)). FIG. 10 is a plan view illustrating an X-ray irradiation path during cephalographic imaging of the first preferred embodiment. FIG. 11 is a block diagram illustrating a configuration of the X-ray imaging apparatus 10 of the first preferred embodiment.

A right-handed XYZ (X-axis, Y-axis, Z-axis) orthogonal coordinate system and a right-handed xyz (x-axis, y-axis, z-axis) orthogonal coordinate system are sometimes defined in the drawings. In the drawing, a direction toward which a tip of an arrow is oriented is defined as a +(plus) direction, and the opposite direction is defined as a −(minus) direction.

In this case, in a state in which a head MH of a subject M1 introduced into the imaging unit 20 is held by a subject holder 72, a front of the head MH is defined as a +Y direction and a rear of the head MH is defined as a −Y direction when viewed from the subject M1. A right-handed direction is defined as a +X direction and the left hand direction is defined as a −Y direction when viewed from the subject M1. An upward direction is defined as a +Z direction and a downward direction is a −Z direction when viewed from the subject M1.

The xyz orthogonal coordinate system is a coordinate system defined on a turning arm 62 rotating with respect to the fixed portion such as the support post 70 standing on a base 7B. In this case, the direction from an X-ray generating unit 40 toward an X-ray detecting unit 50 is defined as the +y direction, and the opposite direction is defined as the −y direction. The right-handed direction from the X-ray generating unit 40 toward the X-ray detecting unit 50 is defined as the +x direction, and the left-handed direction is defined as the −x direction. The upward direction from the X-ray generating unit 40 toward the X-ray detecting unit 50 is defined as the +z direction, and the downward direction is defined as the −z direction. The z-axis direction is parallel to the Z-axis direction. As described later, the turning arm 62 rotates about a rotation axis line 65A parallel to the Z-axis direction and the z-axis direction, whereby the xyz orthogonal coordinate system also rotates about the z-axis direction.

The X-ray imaging apparatus 10 includes the imaging unit 20 and an image processing apparatus 30. The imaging unit 20 is an apparatus that collects X-ray projection data by executing X-ray imaging of the subject M1. For example, the imaging unit 20 is used while accommodated in an X-ray protective room 22. The image processing apparatus 30 processes the X-ray projection data collected by the imaging unit 20, and generates various X-ray images (specifically, a panoramic image, a CT image, and a cephalographic image).

<Imaging Unit 20>

The imaging unit 20 includes the X-ray generating unit 40, the X-ray detecting unit 50, the turning arm 62 (support), the support post 70, and a main body controller 80. A configuration or a function of each unit will be described below.

<X-Ray Generating Unit 40>

As illustrated in FIG. 4, the X-ray generating unit 40 includes an X-ray generator 42 and the X-ray beam shape adjuster 44. The X-ray generator 42 and the X-ray beam shape adjuster 44 are accommodated in a casing 46. The casing 46 is supported by the turning arm 62.

The X-ray generator 42 includes an X-ray tube that is an X-ray source that emits the X-ray beam. Intensity (output intensity) of the X-ray beam emitted from the X-ray generator 42 is controlled by changing voltage and/or current supplied to an X-ray tube 42T (see FIG. 4). The X-ray generator 42 (in particular, the control of a voltage amount and/or a current amount) is controlled by tan X-ray generating unit drive controller 806 of the main body controller 80.

The X-ray beam shape adjuster 44 regulates spread of the X-ray beam emitted from the X-ray generator 42, and adjusts the X-ray beam into a shape according to imaging purpose. That is, the X-ray beam shape adjuster 44 controls an X-ray irradiation range with respect to the subject M1 (examinee). The X-ray beam shape adjuster 44 is controlled by the X-ray generating unit drive controller 806.

FIGS. 7 and 8 are views illustrating a configuration example of the X-ray beam shape adjuster 44. In this case, the X-ray beam shape adjuster 44 includes four shielding members 441 to 444 disposed close to the X-ray generator 42. The shielding members 441 to 444 are made of a material (such as lead) absorbing the X-rays, and are formed into a rectangular plate shape.

The shielding members 441, 442 are disposed on upper and lower sides (a +z side and a −z side) in a front view of an emission port of the X-ray generator 42, and are disposed such that each long side is parallel to the x-axis direction. The X-ray beam shape adjuster 44 includes a moving mechanism (not illustrated) that moves the shielding members 441, 442 in a longitudinal direction (z-axis direction). For example, the moving mechanism can be constructed with a ball screw mechanism or a linear motor mechanism.

The shielding members 443, 444 are disposed on left and right sides (a +x side and a −x side) in a front view of the emission port of the X-ray generator 42, and are disposed such that each long side is parallel to the z-axis direction. The X-ray beam shape adjuster 44 includes a moving mechanism (not illustrated) that moves each of the shielding members 443, 444 in a crosswise direction (x-axis direction). For example, the moving mechanism can be constructed with a ball screw mechanism or a linear motor mechanism.

An opening 445 formed by opposing edges 441a, 442a of the shielding members 441, 442 and opposing edges 443a, 444a of the shielding members 443, 444 is adjusted to the shape and size according to the imaging purpose by controlling the positions of the shielding members 441 to 444 using the moving mechanisms.

For example, as illustrated in FIG. 7, a distance between the edge portions 441a, 442a and a distance between the edges 443a, 444a are relatively largely adjusted, so that the opening 445 has a square shape in a front view. The X-ray beam emitted from the X-ray generator 42 is shaped into an X-ray cone beam spreading in a regular quadrangular pyramidal shape toward the X-ray detecting unit 50 by passing through the square-shaped opening 445. The X-ray cone beam is suitable for large irradiation field CT imaging (to be described later).

As illustrated in FIG. 8, the distance between the edges 443a, 444a is adjusted relatively large and the distance between the edges 441a, 442a is adjusted small, so that the opening 445 becomes a vertically elongated rectangular shape in a front view. The X-ray beam emitted from the X-ray generator 42 is shaped into an X-ray narrow beam spreading in a vertically elongated truncated pyramidal shape by passing through the rectangular opening 445. The X-ray narrow beam is suitable for the panoramic imaging.

FIG. 9 is a view illustrating another example of the X-ray beam shape adjuster 44. The X-ray beam shape adjuster 44 may include shielding members 446, 447 in FIG. 9 instead of the shielding members 441 to 444. The shielding members 446, 447 are formed into an L-shaped plate shape, and edges 446a, 447a constituting interior corners of the he shielding members 446, 447 are combined to form an opening 448. Each of the shielding members 446, 447 is movable in the longitudinal direction (z-axis direction) and the crosswise direction (x-axis direction) by a moving mechanism (not illustrated). The shape of the opening 448 is adjusted by adjusting the positions of the shielding members 446, 447 using the moving mechanism.

The X-ray beam shape adjuster 44 in FIGS. 7 to 9 is constructed with the plurality of shielding members 441 to 444 or the shielding members 446, 447 and the moving mechanism. Alternatively, the X-ray beam shape adjuster 44 may also be constructed with a single shielding member in which a plurality of openings are formed according to the imaging purpose and the moving mechanism. In this case, the single shielding member may be moved by the moving mechanism such that the X-ray beam emitted from the X-ray generator 42 passes through the opening according to the imaging purpose.

<X-Ray Detecting Unit 50>

Referring to FIG. 4, the X-ray detecting unit 50 includes an X-ray detector 52 and an X-ray detector vertical movement driving unit 53. The X-ray detector 52 detects the X-ray beam emitted from the X-ray generating unit 40. For example, the X-ray detector 52 may be constructed with a flat panel detector (FPD) including a detection surface spreading flat or an X-ray fluorescence intensifier (Image Intensifier (I.I.)).

The plurality of detecting elements arranged on the detection surface of the X-ray detector 52 convert the intensity of the incident X-ray into an electric signal. The electric signal is input to the main body controller 80 or the image processing apparatus 30 as an output signal, and an X-ray projection image is generated based on the output signal.

The X-ray detector 52 is attached to a side facing the X-ray generator 42 in a casing 54. The detection surface of the X-ray detector 52 is irradiated with the X-ray beam emitted from the X-ray generator 42. The casing 54 is supported by the turning arm 62 while the X-ray detector 52 and the X-ray detector vertical movement driving unit 53 are accommodated in the casing 54.

The X-ray detector vertical movement driving unit 53 moves the X-ray detector 52 in the vertical direction (z-axis direction) with respect to the turning arm 62. The X-ray detector vertical movement driving section 53 includes a motor 531, a ball screw 532, and a nut 533. The motor 531 rotates the ball screw 532 extending in the Z-axis direction about the Z axis. The nut 533 is screwed in the ball screw 532, and the side of the nut 533 is attached to a back surface of the X-ray detector 52. The X-ray detector 52 is guided by a rail (not illustrated) so as to move in the Z-axis direction.

The motor 531 is controlled by the X-ray detecting unit drive controller 804. The motor 531 rotates the ball screw 532 based on a control signal from the X-ray detecting unit drive controller 804, whereby the nut 533 and the X-ray detector 52 are moved in the Z-axis direction. The X-ray detector 52 is guided by a guide rail (not illustrated) so as to move along the Z-axis direction.

As illustrated in FIG. 4, the casing 54 includes a tubular unit 541 that is formed in a tubular shape opened downward while extending downward from an end of the turning arm 62 and an outer box 542 that covers the outside of tubular unit 541 while being opened upward.

The motor 531 of the X-ray detector vertical movement driving section 53 is fixed to the tubular unit 541. The outer box 542 is biased upward by a spring 55 attached to the tubular unit 541. A lower end of the X-ray detector 52 abuts on an inner bottom surface of the outer box 542.

When the X-ray detector vertical movement driving unit 53 moves the X-ray detector 52 downward, the X-ray detector 52 pushes down the outer box 542. At this point, since the spring 55 becomes longer than the natural length, so that restoring force is accumulated in the spring 55. When the X-ray detector vertical movement driving unit 53 moves the X-ray detector 52 upward, the outer box 542 is pulled upward by the restoring force of the spring 55. Consequently, the outer box 542 rises while abutting on the rising X-ray detector 52.

The outer box 542 moves up and down with respect to the inner tubular unit 541 according to a height position of the X-ray detector 52, whereby a height width of the casing 54 expands and contracts as a whole. The X-ray detector 52 in which the position in the height direction changes can properly be protected by the expansion and contraction of the casing 54 in this manner. The outer box 542 is disposed at a position as high as possible by the spring 55, so that the prevention of the rotation of the casing 54 can be reduced during the X-ray imaging.

In the first preferred embodiment, when the X-ray detector 52 is disposed at the highest position (that is, when the outer box 542 is disposed at the highest position), the lowermost end (that is, the lowermost end of the casing 54) of the outer box 542 is located lower than the lowermost end of the casing 46 of the X-ray generating unit 40. That is, regardless of the height of the X-ray detector 52, the lowermost end of the casing 54 is always located lower than the lowermost end of the casing 46. However, the lowermost end of the casing 54 is not necessarily located lower than the lowermost end of the casing 46.

<Turning Arm 62>

The turning arm 62 is suspended from the upper frame 64 with a rotation shaft 65 interposed therebetween. The casing 46 is attached to one end of the turning arm 62, and the casing 54 is attached to the other end of the turning arm 62. That is, the turning arm 62 supports the X-ray generator 42 at one end side with the casing 46 interposed therebetween, and supports the X-ray detector 52 at the other end side with the casing 54 interposed therebetween.

The insides of the casings 46, 54 and the turning arm 62 form a series of cavities. Wirings, such as a signal wiring, a power supply wiring, a control wiring, and an electric cable 90 (to be described later), which operate the respective units of the X-ray generating unit 40 and the X-ray detecting unit 50, are disposed in the cavity. A working opening used to attach the wirings and a control board or an opening used to radiate heat may be provided at appropriate positions of the casings 46, 54 and the turning arm 62.

As illustrated in FIGS. 1 to 4, the upper frame 64 is attached to the support post 70. The rotation shaft 65 extending in the Z-axis direction is attached to the upper frame 64, and the end of the rotation shaft 65 is connected to an intermediate position between portions supporting the X-ray generating unit 40 and the X-ray detecting unit 50 in the turning arm 62. Consequently, the turning arm 62 is suspended from the upper frame 64 with the rotation shaft 65 interposed therebetween.

As illustrated in FIG. 6, a turning driving unit 642 is provided in the turning arm 62. The turning driving unit 642 turns the turning arm 62 about the rotation shaft 65 by rotating a turning motor 6421 provided in the turning arm 62. As illustrated in FIG. 6, the turning driving unit 642 includes the turning motor 6421 and an endless belt 6422. The turning driving unit 642 (specifically, the turning motor 6421) is controlled by a support drive controller 802. The endless belt 6422 is entrained around the turning motor 6421 and the rotation shaft 65. The endless belt 6422 is rotated by driving the turning motor 6421, which allows the rotation of the turning arm 62.

A bearing 6423 (see FIG. 6) is interposed between the rotation shaft 65 and the turning arm 62. The turning arm 62 can smoothly rotate with respect to the rotation shaft 65 by the bearing 6423.

The turning driving unit 642 may be provided in the upper frame 64. In this case, the rotation shaft 65 rotatable with respect to the upper frame 64 is rotated together with the turning arm 62 fixed to the rotation shaft 65.

A rotation axis line 65A is set inside the rotation shaft 65 that is an axis on which the turning arm 62 turns mechanically. As illustrated in FIG. 4, the turning arm 62, the casing 46, and the casing 54 constitute a turning unit 67. The upper frame 64 is a turning support 64A that supports the turning unit 67 with the rotation shaft 65 interposed therebetween. The turning arm 62 turns about the axis of the rotation shaft 65, whereby the turning unit 67 turns about the rotation axis line 65A.

The turning arm 62 supports the casing 46 at one end side, and supports the casing 54 at the other end side opposite thereto. Consequently, a part of the turning arm 62 supports the X-ray generator 42 while another part supports the X-ray detector 52 with the rotation axis line 65A sandwiched therebetween. That is, the support rotatably supports the subject M1 while the X-ray generator 42 and the X-ray detector 52 are opposed to each other.

An XY direction movement driving unit 644 that moves the rotation shaft 65 in the X-axis direction and the Y-axis direction is provided in the upper frame 64. The XY direction movement driving unit 644 moves the turning arm 62 in the X-axis direction and the Y-axis direction by moving the rotation shaft 65 in the X-axis direction and the Y-axis direction. The XY direction movement driving unit 644 includes an XY table 6440 and a driving motor 6442 as illustrated in FIG. 5.

The XY table 6440 includes an X table 6440X and a Y table 6440Y. The X table 6440X moves the turning arm 62 in the crosswise direction (X-axis direction). The Y table 6440Y moves the turning arm 62 in a front-back direction (Y-axis direction). The X table 6440X is fixed to the Y table 6440Y, and moves in the Y-axis direction in association with the movement of the Y table 6440Y.

The driving motor 6442 includes an X-axis driving motor 6442X that drives the X table 6440X and a Y-axis driving motor 6442Y that drives the Y table 6440Y.

In the X-ray imaging apparatus 10, as illustrated in FIG. 11, the support drive controller 802 of the main body controller 80 controls the XY direction movement driving unit 644.

The XY direction movement driving unit 644 moves the turning driving unit 642 in the X-axis direction and the Y-axis direction together with the rotation axis 65. Consequently, the rotation shaft 65 is movable in an XY plane, and is rotatable about the Z-axis that is an axial center position of the rotation shaft 65 at a specific position after the movement in the XY plane.

The XY direction movement driving unit 644 may be provided in the turning arm 62. In this case, the other end of the rotation shaft 65 fixed at a constant position in the XY plane of the upper frame 64 is fixed to the XY table 6440 provided in the turning arm 62. The XY table 6440 moves in the X-axis direction and the Y-axis direction, whereby the turning arm 62 relatively moves in the X-axis direction and the Y-axis direction with respect to the rotation axis 65 at the constant position.

Both of the turning driving unit 642 and the XY direction movement driving unit 644 may be provided in the turning arm 62. In this case, the turning arm 62 moves relatively in the X-axis direction and the Y-axis direction and rotates relatively with respect to the rotation shaft 65, which is fixed at the constant position in the XY plane and does not rotate.

As illustrated in FIG. 4, a Z direction driving unit 646 (vertical movement driving unit) that elevates the upper frame 64 in the Z-axis direction is attached to the support post 70. The Z direction driving unit 646 includes a motor 6462, a ball screw 6464, a nut 6466, and a plurality (four in this case) of rollers 6468.

The motor 6462 rotates the ball screw 6464 extending in the Z-axis direction about the Z-axis. The nut 6466 is screwed in the ball screw 6464. Each of the rollers 6468 is vertically movably engaged with a pair of rails 702 provided on the support post 70, and the movement direction of the roller 6468 is restricted so as to move only in the extending direction (Z-axis direction) of the pair of rails 702.

In the example of FIG. 4, the motor 6462 disposed on the base 7B is attached to a lower portion of the support post 70, and the nut 6466 is fixed to the upper frame 64. Each roller 6468 is attached to the upper frame 64.

The motor 6462 rotates the ball screw 6464 clockwise or counterclockwise, whereby the nut 6466 moves upward or downward along the ball screw 6464. At this point, each of the rollers 6468 moves on the pair of rails 702, whereby the upper frame 64 is elevated in the Z-axis direction. The X-ray generating unit 40 and the X-ray detecting unit 50, which are supported by the turning arm 62, move in the Z-axis direction in association with the elevating movement of the upper frame 64. The Z direction driving unit 646 is an example of the vertical movement driving unit that vertically moves the turning arm 62 and the upper frame 64 by vertically moving the upper frame 64.

<Cephalographic Unit 66>

The cephalographic unit 66 is a unit used to acquire a head X-ray standard photograph. As illustrated in FIGS. 1 and 2, the cephalographic unit 66 is provided at a tip of an arm 648 extending horizontally from the upper frame 64. The cephalographic unit 66 includes a head fixture 660, a secondary slit mechanism 662, and an X-ray detector 664.

The head fixture 660 is a device that positions the head MH. In this case, the head fixture 660 includes an ear rod that positions both ears by inserting a pair of rod-shaped tips into the ears on both sides of the head portion MH and a forehead rod that abuts on a forehead of the head MH to position the head MH. At this point, the head MH is positioned by the head fixture 660 such that the front of the head MH faces the +X side.

The secondary slit mechanism 662 includes a slit member in which a slit extending in the Z-axis direction is formed and a moving mechanism that moves the slit member in the Y direction. The head MH fixed to the head fixture 660 is irradiated with the X-ray passing through the slits among the X-rays emitted from the X-ray generator 42. In the cephalographic imaging, the slit member moves in the X-axis direction, whereby the head MH is scanned using the X-ray.

The X-ray detector 664 detects the X-ray transmitted through the head MH positioned by the head fixture 660. The X-ray detector 664 includes a detector that detects the X-ray and a moving mechanism that moves the detector in the Y-axis direction. The detector includes a detection surface extending in the +Z direction, the detection surface corresponding to the shape of the slit of the secondary slit mechanism 662. The moving mechanism moves the detector in the Y-axis direction according to the movement of the slit member in the Y-axis direction. Consequently, the detector detects the X-ray, which passes through the slit and is transmitted through the head MH.

When the cephalographic imaging is executed by the X-ray imaging apparatus 10, as illustrated in FIG. 10, the turning arm 62 rotates by a predetermined angle, and the casing 46 releases the opposing relationship with the X-ray detecting unit 50 and rotates so as to face the X-ray detector 664 for the cephalographic imaging, whereby the X-ray detecting unit 50 is disposed at a position out of a line connecting the X-ray generating unit 40 and the cephalographic unit 66. The casing 46 of the X-ray generating unit 40 is turned about the Z-axis with respect to the turning arm 62, whereby the emission port (an opening 445 of the X-ray beam shape adjuster 44) of the X-ray of the X-ray generator 42 is directed to the X-ray detector 664 of the cephalographic unit 66. The mechanism that turns the casing 46 may be manually operable, or operable under the control of the main body controller 80. The X-ray beams are emitted from the X-ray generating unit 40 while the X-ray generating unit 40 and the cephalographic unit 66 are disposed in the positional relationship in FIG. 10, whereby the cephalographic imaging is executed.

<Support Post 70>

The support post 70 is a member extending in the Z-axis direction, and supports the upper frame 64 and the subject holder 72.

<Subject Holder 72>

The subject holder 72 is a member that holds the subject M1 (head MH). The subject holder 72 includes a chin rest 722, a head holder 723, a lower frame 724, an arm 726, and a subject movement driving unit 728.

The chin rest 722 supports the tip of the lower jaw of the head MH, thereby supporting the head MH. The head holder 723 positions the head MH with respect to the X-axis direction by holding the head holder 723 from both sides of the head MH. The chin rest 722 and the head holder 723 are connected to the lower frame 724 with the arm 726 interposed therebetween. A mechanical element constructed with the chin rest 722 and the head holder 723 to fix the head MH of the subject M1 constitutes the subject holder 72 or a part of the subject holder 72 as a head holder 72H.

The lower frame 724 is attached to the support post 70, and moves in the Z-axis direction. As the lower frame 724 moves in the Z-axis direction, the chin rest 722 fixed to the arm 726 moves in the Z-axis direction.

The arm 726 is a member that connects the lower frame 724 and the chin rest 722. In the example of FIG. 4, the arm 726 is constructed with a portion extending in parallel to the XY plane from the lower frame 724 and a portion, which extends to the Z-axis and is connected to the chin rest 722.

The subject movement driving unit 728 includes a motor 7282, a ball screw 7284, a nut 7286, and a plurality of (four in this case) rollers 7288.

The motor 7282 rotates the ball screw 7284 extending in the Z-axis direction. The nut 7286 is screwed in the ball screw 7284. Each of the rollers 7288 is engaged with the pair of rails 702, and the moving direction of the roller 7288 is restricted so as to move only in the extending direction (Z-axis direction) of the pair of rails 702.

In the example of FIG. 4, the motor 7282 and the ball screw 7284 are fixed to the lower frame 724. The nut 7286 is fixed to the upper frame 64. In the illustrated example, the ball screw 7284 extends in the +Z direction from a top of the lower frame 724, and is screwed in the nut 7286 fixed in the vicinity of the bottom of the upper frame 64. Each of the rollers 7288 is attached to the lower frame 724.

When the motor 7282 rotates the ball screw 7284 clockwise or counterclockwise, the lower frame 724 moves upward or downward with respect to the nut 7286 fixed to the upper frame 64. At this point, each of the rollers 7288 moves along the pair of rails 702, whereby the lower frame 724 moves in the Z-axis direction.

As the lower frame 724 moves in the Z axis direction, the chin rest 722 moves along the Z-axis. The turning arm 62 is relatively elevated with respect to the head MH while the height of the head MH is kept constant, which allows a point irradiated with the X-ray on the head MH to be changed in the Z-axis direction. Specifically, the turning arm 62 and the subject holder 72 are elevated by the Z direction driving unit 646 according to the actual position of the head MH, whereby the head MH is fixed to the head holder 72H. Then, the subject holder 72 may be lowered by the subject movement driving unit 728 while the turning arm 62 is raised by the Z direction driving unit 646. Alternatively, the subject holder 72 may be raised by the subject movement driving unit 728 while the turning arm 62 is lowered by the Z direction driving unit 646.

The turning arm 62 and the subject holder 72 (the head holder 72H) are integrally moved up and down by the Z direction driving unit 646. The subject holder 72 is vertically moved up and down relative to the turning arm 62 by the subject movement driving unit 728. That is, the turning arm 62 and the subject holder 72 can independently be moved up and down by the Z direction driving unit 646 and the subject movement driving unit 728.

The position where the head of the subject M1 is supported may be changed by changing the positions in the Z-axis direction of the chin rest 722 and the head holder 723. For example, the positions of the chin rest 722 and the head holder 723 are set according to the position of the head of the subject M1 in an upright posture. As illustrated in FIG. 4, in the case that the subject M1 has a standard skeleton, a Frankfurt's plane FR1 of the subject M1 becomes horizontal when the head MH is held by the subject holder 72. A body axis BA1 passing through the head MH becomes parallel to the vertical direction when the head MH is held by the subject holder 72. AS used herein, the body axis means a symmetrical axis that is set when the human body is considered to be substantially symmetrical as viewed from the front of the human body.

<Main Body Controller 80>

The main body controller 80 controls each element of the imaging unit 20 to cause the imaging unit 20 to execute the X-ray imaging. A hardware configuration of the main body controller 80 is similar to that of a general computer or a work station. That is, the main body controller 80 includes a CPU that performs various arithmetic processing, a ROM that is a read-only memory in which a basic program is stored, a RAM that is a readable and writable memory in which various pieces of information are stored, and a storage in which a control application or data is stored.

Referring to FIG. 11, the main body controller 80 includes a mode setting unit 800, an imaging region setting unit 801, a support drive controller 802, an imaging condition setting unit 803, an X-ray detecting unit drive controller 804, and an X-ray generating unit drive controller 806, and a subject holder drive controller 808. Each controller is a function implemented by the operation of the CPU (general-purpose circuit) according to a controlling application. A part or all of these functions may be implemented in a hardware manner by construction of a dedicated circuit. Among the circuits of the CPU, portions used for various kinds of control by various control applications may be grasped as the controllers 800, 802, 804, 806, 808, and a combination thereof may be grasped as the main body controller 80.

The mode setting unit 800 sets an imaging type (mode) of the X-ray imaging apparatus 10. The X-ray imaging apparatus 10 executes various kinds of imaging according to the imaging mode set by the mode setting unit 800. The modes corresponding to the panoramic X-ray imaging, the CT imaging, and the cephalographic imaging are previously defined in the X-ray imaging apparatus 10. In the X-ray imaging apparatus 10, an operation display 82 receives selection of the mode, and the mode setting unit 800 sets the imaging mode according to the selection content. In the first preferred embodiment, the mode setting unit 800 and the operation display 82 constitute a mode setting receiving unit that receives the selection of one imaging mode from a plurality of imaging modes.

The imaging region setting unit 801 sets the imaging region (a range of an imaging object) according to the mode executed in the X-ray imaging apparatus 10. The imaging region setting unit 801 displays a region setting screen suitable for the imaging mode set by the mode setting unit 800 on the operation display 82. The mode setting unit 800 sets the imaging region based on operation input performed on the operation display 82 by a manipulator. The operation display 82 constitutes an imaging region designating unit 820 that designates the imaging region.

The support drive controller 802 controls the turning of the turning arm 62 by controlling the turning driving unit 642. Specifically, the support drive controller 802 rotates the X-ray generator 42 supported by the turning arm 62 about the rotation axis 65, whereby changing a projection angle of the X-ray beam (X-ray cone beam BX1) with respect to the subject M1.

The support drive controller 802 controls the movement in the X-axis direction and the Y-axis direction of the turning arm 62 by controlling the XY direction movement driving unit 644. Consequently, the support drive controller 802 moves the X-ray generator 42 and the X-ray detector 52 in the X-axis direction and the Y-axis direction.

The support drive controller 802 controls the Z direction drive unit 646 to move the turning arm 62 in the Z direction.

The X-ray detecting unit drive controller 804 controls the X-ray detecting unit 50. For example, the X-ray detecting unit drive controller 804 controls the X-ray detector vertical movement driving unit 53 to vertically move the X-ray detector 52. The X-ray detecting unit drive controller 804 controls positional movement of the X-ray detector 664.

The X-ray generating unit drive controller 806 controls the X-ray generating unit 40. For example, the X-ray generating unit drive controller 806 controls the X-ray generator 42. Specifically, on and off of the X-ray beam emitted from the X-ray generator 42 and the intensity of the X-ray beam are controlled by controlling the voltage or current supplied to the X-ray tube. The X-ray generating unit drive controller 806 also control the shielding of the X-ray beam by controlling the X-ray beam shape adjuster 44. The X-ray beam (for example, the X-ray narrow beam and the X-ray cone beam) having the shape according to the imaging purpose is formed by the shielding control of the X-ray beam. The X-ray generating unit drive controller 806 controls the X-ray beam shape adjuster 44 to prevent the irradiation of the region other than the imaging region ROI in the subject M1 with the X-ray beam.

The subject holder drive controller 808 controls the subject movement driving unit 728 to move the head holder 72H in the Z direction.

The operation display 82 is connected to the main body controller 80. The operation display 82 is provided to display various pieces of information. The operation display 82 is constructed with a touch panel display. The operation display 82 is provided such that various pieces of information are displayed as the image, and such that the manipulator can input various pieces of information (including an imaging condition) to the main body controller 80. As illustrated in FIG. 1, the operation display 82 is provided on an outer wall surface of the X-ray protective room 22. The operation display 82 may be provided on a part of the imaging unit 20, for example, on the outside surface of the casing 54 (outer box 542).

<Image Processing Apparatus 30>

The hardware configuration of the image processing apparatus 30 is similar to that of a general computer or a workstation. That is, the image processing apparatus 30 includes a CPU that performs various arithmetic processing, a ROM that is a read-only memory in which a basic program is stored, and a RAM that is a readable and writable memory in which various pieces of information are stored. The CPU operating according to the control program to function as a controller 31. The controller 31 is connected to an image processor 33 and a storage 35. The image processor 33 acquires the X-ray image by processing an X-ray transmission image, which is generated based on a signal output by the X-ray detector 52 (or the X-ray detector 664 of the cephalographic unit 66) when the imaging unit 20 executes X-ray imaging. The storage 35 stores an application, data, and the like.

The image processor 33 is a function implemented by the operation of the CPU according to the application program. The image processor 33 may be constructed with a GPU (Graphics Processing Unit).

For example, in the case that the panoramic imaging is executed by the imaging unit 20, the image processor 33 performs the arithmetic processing of acquiring the panoramic image in which a target section is imaged. Specifically, the image processor 33 acquires one panoramic image by performing shift-add processing, in which a pixel value is added to a plurality of strip-shaped X-ray projection images acquired by the imaging unit 20 while the plurality of X-ray projection images are mutually shifted according to the position on the section.

In the case that the CT imaging is executed by the imaging unit 20, the image processing unit 33 generates the CT image of each section obtained by slicing the imaging region by performing predetermined pre-processing, filtering, and back-projection processing on the plurality of acquired projection images.

A display 32 that displays the images indicating various pieces of information and an operation unit 34 with which an input operation is performed by the manipulator are connected to the controller 31. The image processing apparatus 30 and the main body controller 80 are connected to each other through communication interfaces 36, 84 so as to be able to communicate with each other.

Figure 12:
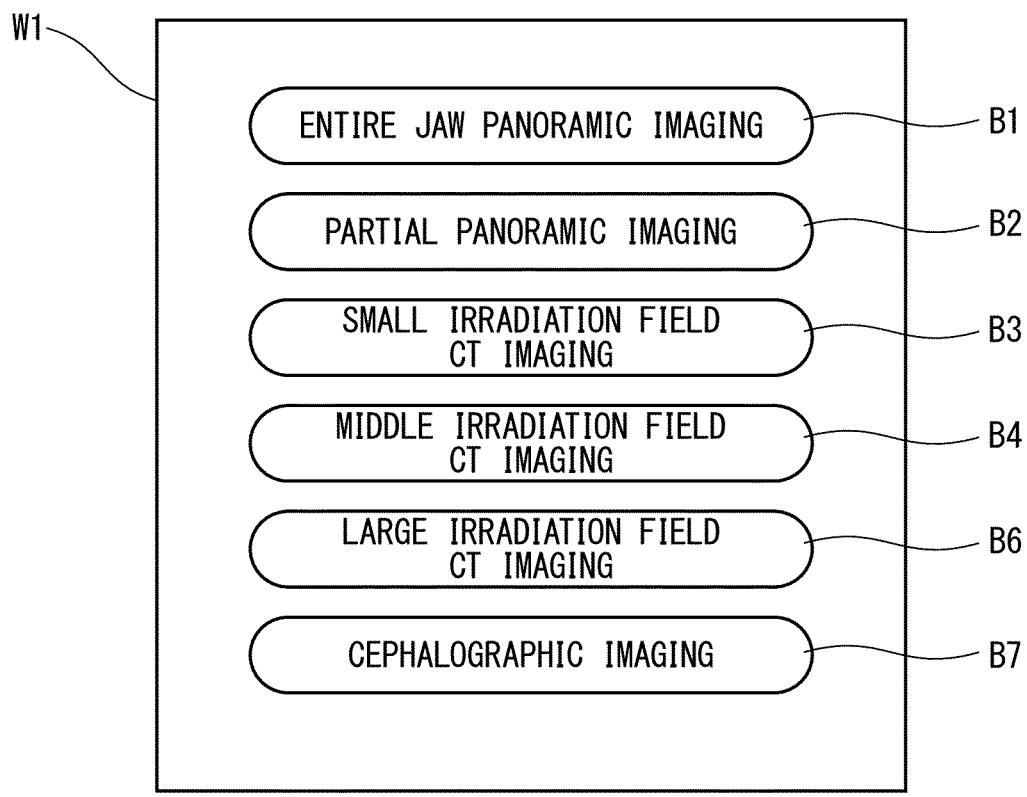
FIG. 12 is a view illustrating an example of a mode setting screen W1.

FIG. 12 is a view illustrating an example of a mode setting screen W1. The mode setting unit 800 outputs a display signal to the operation display 82, thereby displaying the mode setting screen W1 on the operation display 82. The mode setting screen W1 may be displayed on the display 32.

The mode setting screen W1 includes buttons B1 to B7. The buttons B1 to B7 correspond to various imaging modes of entire jaw panoramic imaging, partial panoramic imaging, small irradiation field CT imaging, middle irradiation field CT imaging, large irradiation field CT imaging, and cephalographic imaging, respectively.

The entire jaw panoramic mode is a mode in which the panoramic imaging is executed with the section (entire jaw panoramic section) across the entire jaw (total teeth and upper and lower jaw bones including a temporomandibular joint) in the standard skeleton as the imaging region. The partial panoramic mode is a mode in which the panoramic imaging is executed with a partial section (partial panoramic section) of the section across the entire jaw as the imaging region. In the following description, in the case that the entire jaw panoramic mode and the partial panoramic mode are not distinguished from each other, sometimes the entire jaw panoramic mode and the partial panoramic mode are collectively referred to as a panoramic mode. In the case that the entire jaw panoramic section and the partial panoramic section are not distinguished from each other, sometimes the entire jaw panoramic section and the partial panoramic section are collectively referred to as a panoramic section (or a panoramic layer).

The small irradiation field CT mode is a mode in which the CT imaging is executed in a relatively small imaging region. In this case, the imaging region is formed into a substantially cylindrical shape having a diameter of 40 mm and a height of 40 mm. The large irradiation field CT mode is a mode in which the CT imaging is executed in a relatively large imaging region. In this case, the imaging region is formed into a substantially cylindrical shape having a diameter of 80 mm and a height of 80 mm. The middle irradiation field CT mode is a mode in which the CT imaging is executed in the imaging region that is larger than the imaging region of the small irradiation field CT mode and is smaller than the imaging region of the large irradiation field CT mode. In this case, the imaging region is formed into a substantially cylindrical shape having a diameter of 80 mm and a height of 40 mm. It is needless to say that the size of the imaging region in each mode is not limited to these values. In the following description, in the case that the small irradiation field CT mode, the large irradiation field CT mode, and the middle irradiation field CT mode are not distinguishing from one another, sometimes the small irradiation field CT mode, the large irradiation field CT mode, and the middle irradiation field CT mode are collectively referred to as a CT mode.

The mode setting screen W1 is a screen that is displayed before the X-ray imaging apparatus 10 starts the imaging after being started up. The manipulator performs an input operation to press any one of the buttons B1 to B7 through the operation display 82. Consequently, the mode setting unit 800 sets the imaging mode of the X-ray imaging apparatus 10 based on the input operation.

The imaging region setting unit 801 receives an operation input by the operator and sets the imaging region according to the operation content. The imaging region setting unit 801 causes the display 32 to display an region setting screen suitable for the imaging mode set by the mode setting unit 800, and sets the imaging region based on the input operation performed on the screen.

For example, in the entire jaw panoramic mode, a sectional surface extending over the entire jaw including the upper and lower jaws in the head MH becomes the imaging object. On the other hand, in the partial panoramic mode, a part of the entire jaw becomes the imaging object. For this reason, processing of selecting a part of the entire jaw panoramic section to set the imaging region is performed in the partial panoramic mode.

Figure 13:
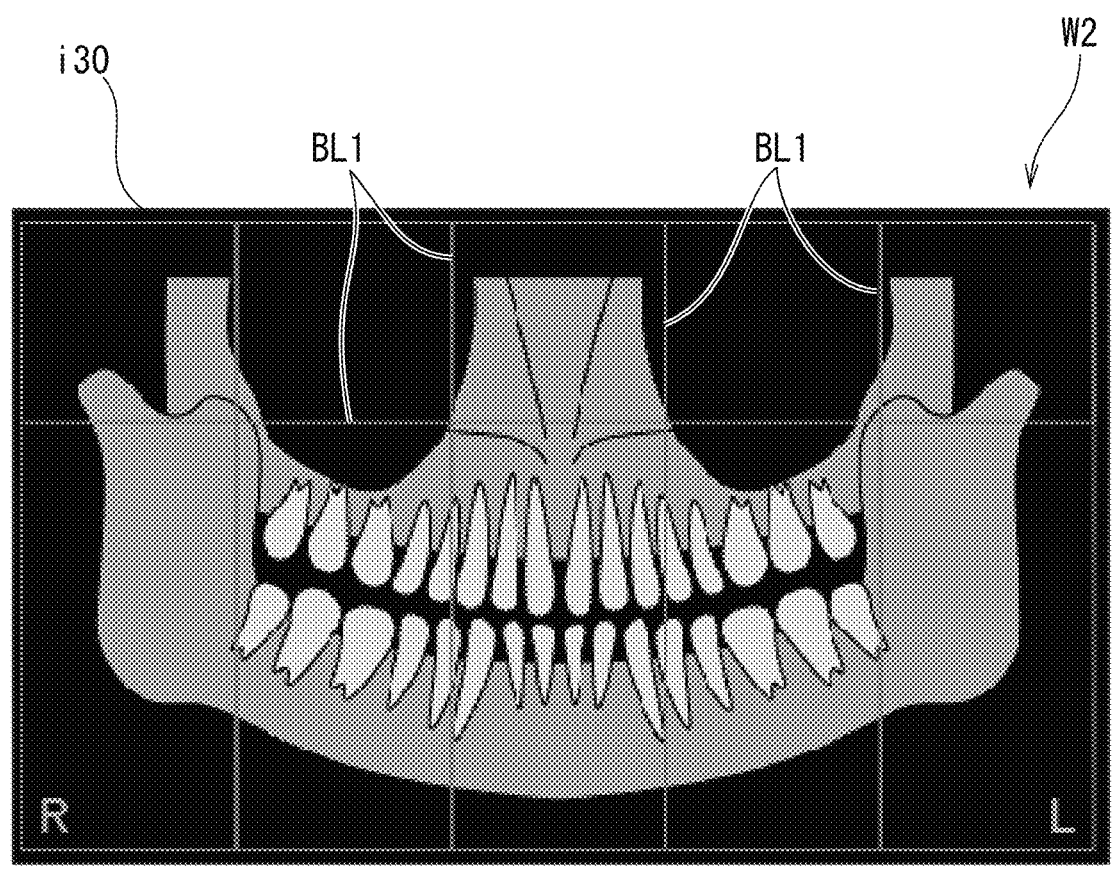
FIG. 13 is a view illustrating an example of a region setting screen W2 displayed in a partial panoramic mode.
Figure 14:
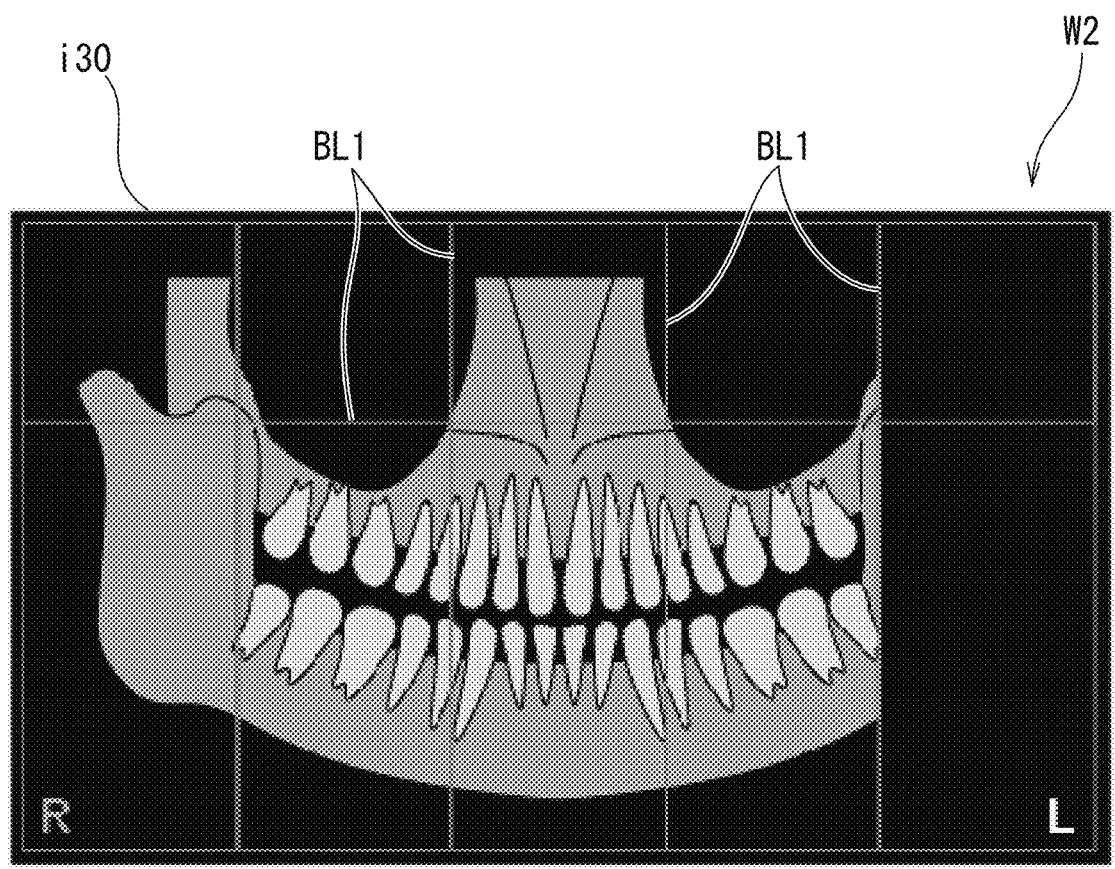
FIG. 14 is a view illustrating an example of the region setting screen W2 displayed in the partial panoramic mode.

FIGS. 13 and 14 are views illustrating examples of a region setting screen W2 displayed in the partial panoramic mode. In the example of FIGS. 13 and 14, an illustration image i30 illustrating the entire jaw panoramic image is displayed on the region setting screen W2. The entire jaw (that is, the same region as the illustration image i30 in FIGS. 13 and 14) is set to the imaging object in the entire jaw panoramic mode, and a part of the entire jaw is set to the imaging object in the partial panoramic imaging. According to the partial panoramic imaging, only the region necessary for the diagnosis can be irradiated with the X-ray, so that the exposure dose can be suppressed.

A boundary line BL1 dividing the illustration image i30 of the entire jaw panorama into a plurality of unit regions is displayed in the region setting screen W2 of FIGS. 13 and 14. The manipulator can select the region included in the panoramic imaging in each region divided by the boundary line BL1. In this case, the region that is not selected by the manipulator (that is, the region that is not included in the imaging region) is not displayed as illustrated in FIG. 14, but only the region selected as the imaging region is displayed.

In FIGS. 13 and 14, the boundary line BL1 is displayed so as to be distinguishable by the manipulator, but this is not required. That is, the boundary line BL1 may be a line, which is virtually defined but cannot visually be recognized by the operator. In FIGS. 13 and 14, the upper and lower jaws are not divided, but a boundary line dividing the upper and lower jaws may be set. In FIGS. 13 and 14, the region selected as the imaging region and the region that is not selected as the imaging region can be distinguished from each other by displaying and non-displaying, but the regions may be distinguishable by color-code.

Figure 15:
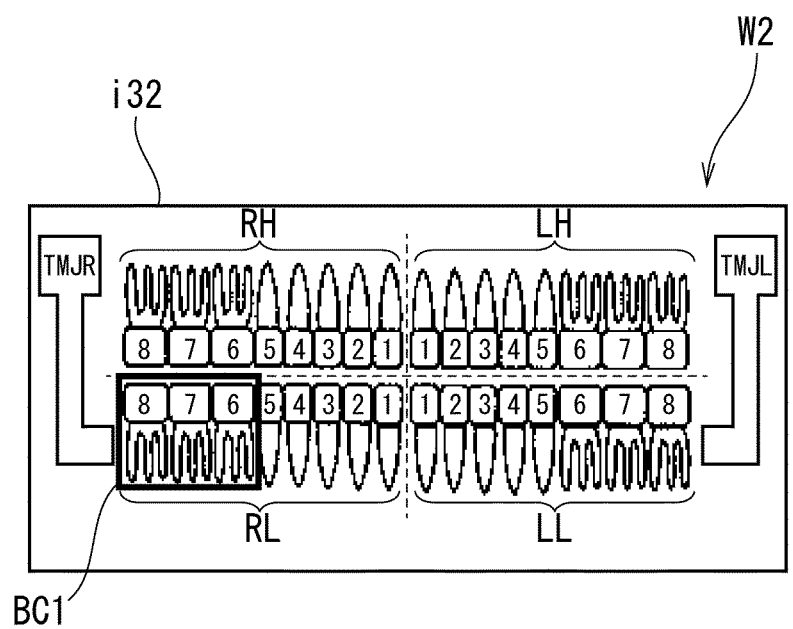
FIG. 15 is a view illustrating another example of the region setting screen W2 in the partial panoramic mode.

FIG. 15 is a view illustrating another example of the region setting screen W2 in the partial panoramic mode. An illustration image i32 in FIG. 15 is not realistically illustrated unlike the illustration image i30 in FIGS. 13 and 14, but schematically illustrated. In the illustration image i32, the front teeth to the molars on the right side of the upper jaw are formed into a group RH of No. 1 to No. 8, the front teeth to the molars on the left side of the upper jaw are formed into a group LH of No. 1 to No. 8, the front teeth to the molars on the right side of the lower jaw are formed into a group RL of No. 1 to No. 8, and the front teeth to the molars on the left side of the lower jaw are formed into a group LL of No. 1 to No. 8. A character string TMJR indicates a right temporomandibular joint, and a character string TMJL indicates a left temporomandibular joint.

In the case that the setting of the imaging region is received on the region setting screen W2 in FIG. 15, for example, when the manipulator can select numbers (1 to 8) indicating the teeth and character strings (TMJR, TMJL) indicating the temporomandibular joints. The imaging region setting unit 801 may set the tooth or the temporomandibular joint corresponding to the selected number or character string to the imaging region in the panoramic mode.

As illustrated in FIG. 15, when the operator surrounds the interest tooth or temporomandibular joint using a closed loop-shaped frame cursor BC1, the imaging region setting unit 801 may set the surrounded region to the imaging region in the panoramic mode. The frame cursor BC1 may be deformable (including magnification and reduction) by a predetermined operation. A plurality of non-consecutive regions may be set to the imaging region by simultaneously setting a plurality of frame cursors BC1.

Figure 16:
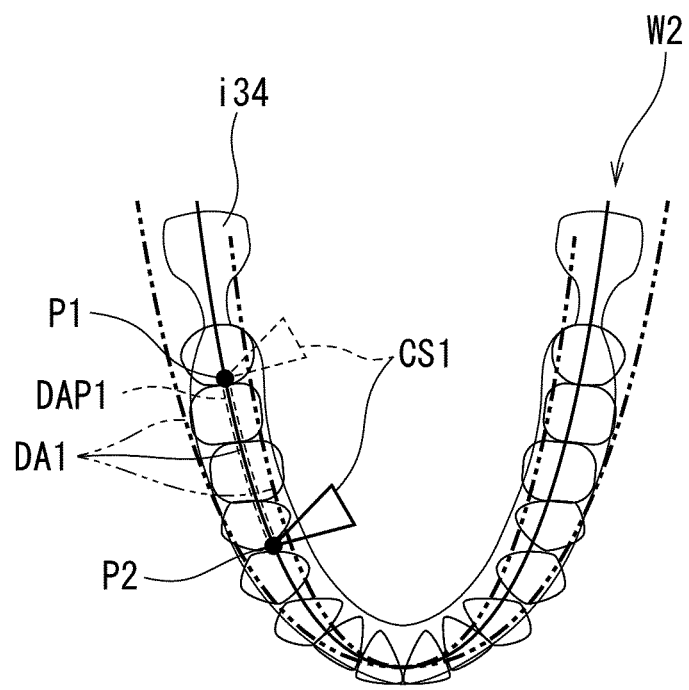
FIG. 16 is a view illustrating still another example of the region setting screen W2 in the partial panoramic mode.

FIG. 16 is a view illustrating still another example of the region setting screen W2 in the partial panoramic mode. An illustration image i34 in FIG. 16 is a plan view of the entire lower jaw. In the region setting screen W2, a dental arch model DA1 that is a curved panoramic section is illustrated as the imaging region in the panoramic mode. The dental arch model DA1 means a virtual three-dimensional shape along the dental arch of a human body that is a statistic standard. In this case, the dental arch model means a virtual imaging object (section), which has a horseshoe shape in planar view and has a predetermined thickness corresponding to a panoramic section. In the panoramic mode, the X-ray imaging is executed on a portion in which the dental arch model DA1 exists.

The dental arch model DA1 occupies a fixed position with respect to the subject holder 72 (head holder 72H) in the real space (three-dimensional space). The position of the panoramic section indicated by the dental arch model DA1 is specified in the real space, so that the position (standard position) of the dental arch model is specified as coordinate information about a three-dimensional coordinate. Information about the dental arch model DA1 is readably stored in the storage 83 (or the storage 35).

In the partial panoramic mode, the manipulator performs an operation to designate a region of interest on the region setting screen W2 using a pointer (pointer cursor CS1). For example, in the example of FIG. 16, the manipulator performs an operation to designate two points P1, P2 on the dental arch model DA1 using the pointer cursor CS1. Consequently, the imaging region setting unit 801 sets a dental arch portion DAP1 between the points P1, P2 of the dental arch model DA1 to the imaging region. The dental arch model DA1 may previously be divided into a plurality of pieces and the operation to designate the imaging region may be received in each division unit.

As illustrated by a two-dot chain line in FIG. 10, the dental arch model DA1 may be deformable according to a predetermined operation of the manipulator. A curvature of the dental arch model DA1 may be changed according to the jaw shape of the subject M1 or the position of the region of interest. The dental arch model DA1 may be moved in the front back direction or the like with respect to the illustration image i34. The imaging region setting unit 801 sets the imaging region in the panoramic mode based on the deformed shape of the dental arch model DA1 and the post-movement position. The dental arch portion DAP1 may be set on the deformed dental arch model DA1.

The imaging region setting unit 801 may set the position in the height direction (Z-axis direction) of the panoramic section. In this case, the operation display 82 (or the operation unit 34) receives the input of designation operation while the imaging region setting unit 801 displays the screen receiving the designation of the height position of the panorama section on the operation display 82 (or the display 32). The imaging region setting unit 801 may set the panoramic section at the designated height position.

Figure 17:
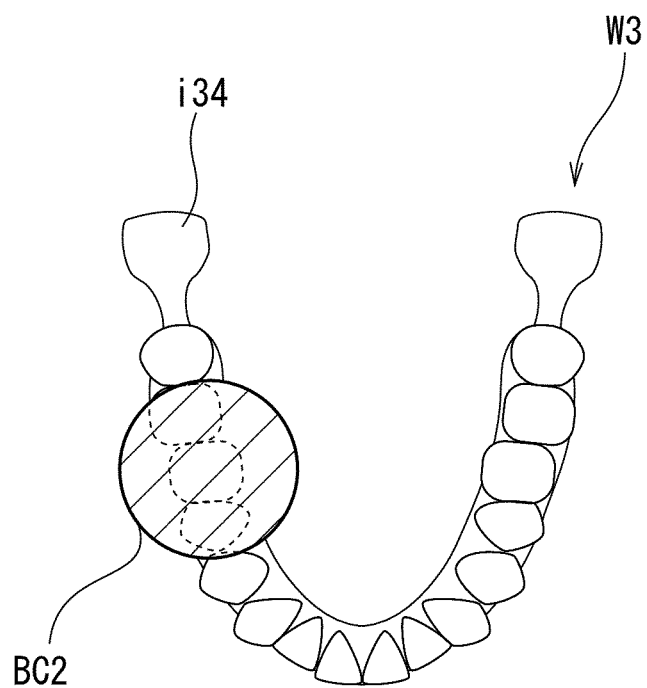
FIG. 17 is a view illustrating an example of a region setting screen W3 in a CT mode.

FIG. 17 is a view illustrating an example of a region setting screen W3 in the CT mode. The illustration image i34 in FIG. 17 is a plan view of the entire lower jaw. In the region setting screen W3, when the manipulator surrounds the interest teeth and temporomandibular joints using a closed loop-shaped frame cursor BC2, the imaging region setting unit 801 sets the surrounded region to the imaging region of the CT imaging.

Although the frame cursor BC2 is circularly displayed on the illustration image i34, the imaging region on the real space has substantially columnar shape extending in the Z-axis direction. The frame cursor BC2 is set to a different size in each CT mode set by the mode setting unit 800. For the large irradiation field CT imaging, for example, a large-size frame cursor BC2 capable of including the entire jaw is prepared in order to set the imaging region having a radius of 80 cm. For the small irradiation field CT imaging, for example, a small-size frame cursor BC2 corresponding to the imaging region having a radius of 40 cm is prepared (see FIG. 17). For the medium irradiation field CT imaging, an intermediate-size frame cursor BC2 between the large-size frame cursor BC2 in the large irradiation field CT imaging and the small-size frame cursor BC2 in the small irradiation field CT imaging is prepared. The radius size of the frame cursor BC2 may be fixed in each CT mode, but the radius size may be changed by a predetermined operation.

The shape of the imaging region in planar view is not limited to a circle. For example, the shape of the imaging region can be changed into various shapes such as an elliptical shape, an oval shape, and a substantially triangular shape by controlling the X-ray beam shape adjuster 44 during the CT imaging.

The dimension in the height direction of the imaging region may be fixed in each CT mode, but the dimension in the height direction of the imaging region may be designated by the manipulator according to the dimension including the region of interest. For example, the operator can select one of the upper jaw, the lower jaw, and the upper and lower jaws suitable for the position of the region of interest, and the imaging region setting unit 801 may set the dimension in the height direction of the imaging region according to the standard dimension of the selected region.

The position in the height direction of the imaging region may be designated by the manipulator. The imaging region setting unit 801 may set the imaging region according to the height position designated by the manipulator.

As illustrated in FIG. 17, in the case that the circular frame cursor BC2 surrounding the entire jaw is set, the imaging region setting unit 801 calculates the coordinate and dimension on the real space corresponding to the position of the frame cursor BC2.

In the case that the imaging region in the CT mode is set, it is also conceivable to use the region setting screen W2 in FIG. 13 or FIG. 15. For example, in the case that the region setting screen W2 in FIG. 7 is used, the manipulator selects one region divided by the boundary line BL1. The imaging region setting unit 801 may set the region on the real space corresponding to the selected region to the imaging region of the CT imaging. In the case that the region setting screen W2 in FIG. 15 is used, the region corresponding to the tooth or temporomandibular joint selected by the manipulator may be set to the imaging region of the CT imaging.

In FIGS. 13 to 17, the imaging region is set using the illustration image. However, the imaging region may be set using an image obtained by imaging the head MH. For example, the imaging region may be set while two simple X-ray projection images obtained by irradiating the head MH with the X-ray from two directions is used as a scout image. Alternatively, the panoramic image may be used as the scout image.

The imaging condition setting unit 803 sets an imaging condition necessary for performing various imaging modes. For example, the imaging condition setting unit 803 sets the size of the subject M1. As described above, in the first preferred embodiment, the imaging region is set on the image illustrating the head MH (mainly the jaw), and the image used at this time is the standard model of the subject M1. For this reason, in the case that the size of the subject M1 is different from the standard size, the imaging region on the real space decided by default from the standard model deviates from the region of interest in the actual subject M1. The imaging condition setting unit 803 receives designation of the actual size of the subject M1. Consequently, the imaging region setting unit 801 converts the imaging region set in the standard model into the region in the actual subject M1. The imaging condition setting unit 803 may read the human body feature information (such as sexuality, a height, a weight, and age) of the subject M1 from the electronic medical chart stored in the storage 83 (or the storage 35), and automatically set the size of the subject M1.

The imaging condition setting unit 803 sets a current value and/or an applied voltage value supplied to the X-ray tube of the X-ray generator 42. The current value and/or the voltage value may be a predetermined value according to the imaging mode set by the mode setting unit 800, or may be changeable by a manipulator as appropriate.

The imaging condition setting unit 803 sets the turning angles of the X-ray generator 42 and the X-ray detector 52 in the CT mode. At this point, the imaging condition setting unit 803 sets the projection angle to one of 180 degrees and 360 degrees. The selection of the projection angle is performed by the predetermined designation operation of the manipulator. The projection angle is not necessarily set to the angle selected from among predetermined angles. However, for example, the manipulator may designate any angle.

Based on the imaging mode set by the mode setting unit 800 and the imaging region set by the imaging region setting unit 801, the support drive controller 802, the X-ray detection section drive controller 804, the X-ray generating unit drive controller 806, and the subject holder drive controller 808 of the main body controller 80 control the respective elements to perform X-ray imaging.

<Operation of X-ray Imaging Apparatus 10>

Figure 18:
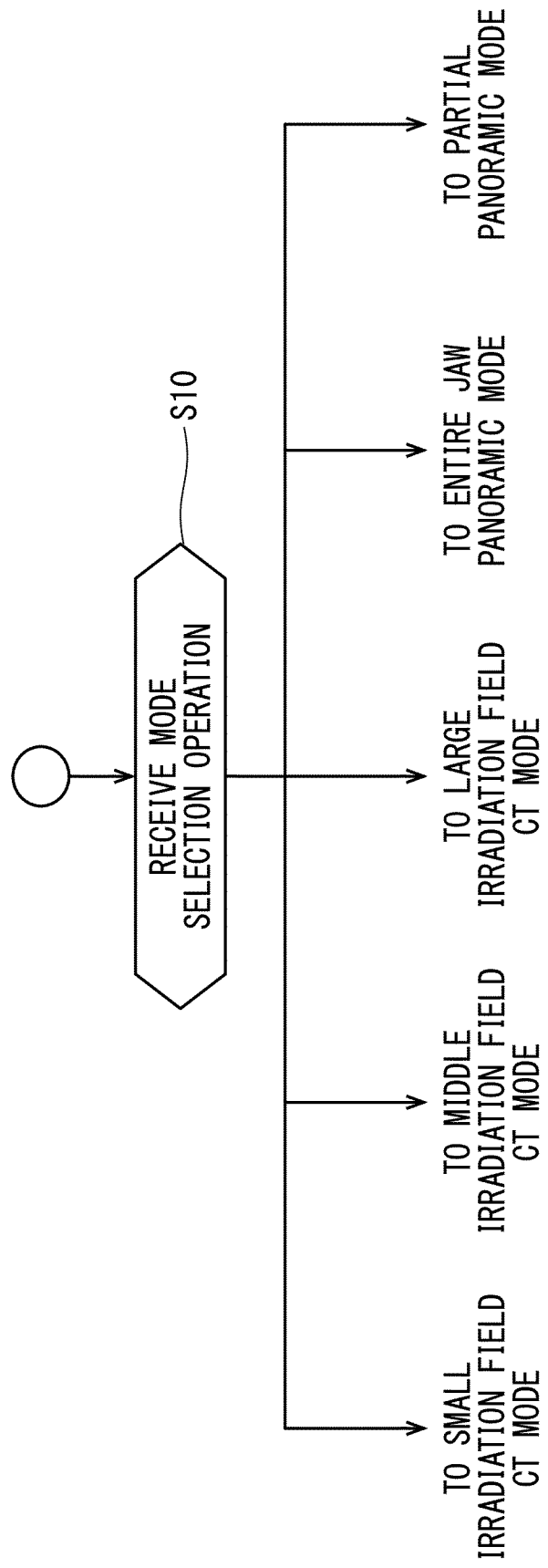
FIG. 18 is a flowchart illustrating operation of the X-ray imaging apparatus 10 of the first preferred embodiment.

FIG. 18 is a flowchart illustrating the operation of the X-ray imaging apparatus 10 of the first preferred embodiment. In the following description, the operation of the imaging unit 20 is performed under the control of the main body controller 80 unless otherwise specified.

When the X-ray imaging apparatus 10 is activated, electricity is supplied to each element, so that the imaging unit 20, the main body controller 80, and the image processing apparatus 30 become a standby state. Then, the mode setting screen W1 is displayed on the operation display 82 (or the display 32) to perform the processing of setting the imaging mode (step S10). In particular, the mode setting unit 800 causes the display 32 to display the mode setting screen W1 (see FIG. 12), receives the input operation input to select the imaging mode, and sets the imaging mode based on the input operation. In this case, the operation mode of the X-ray imaging apparatus 10 is set to one of three CT modes or two panoramic modes.

When the imaging mode is set in step S10, the X-ray imaging apparatus 10 performs the operation corresponding to the set mode. A processing content of each mode will be described below.

<Small Irradiation Field CT Mode>

Figure 19:
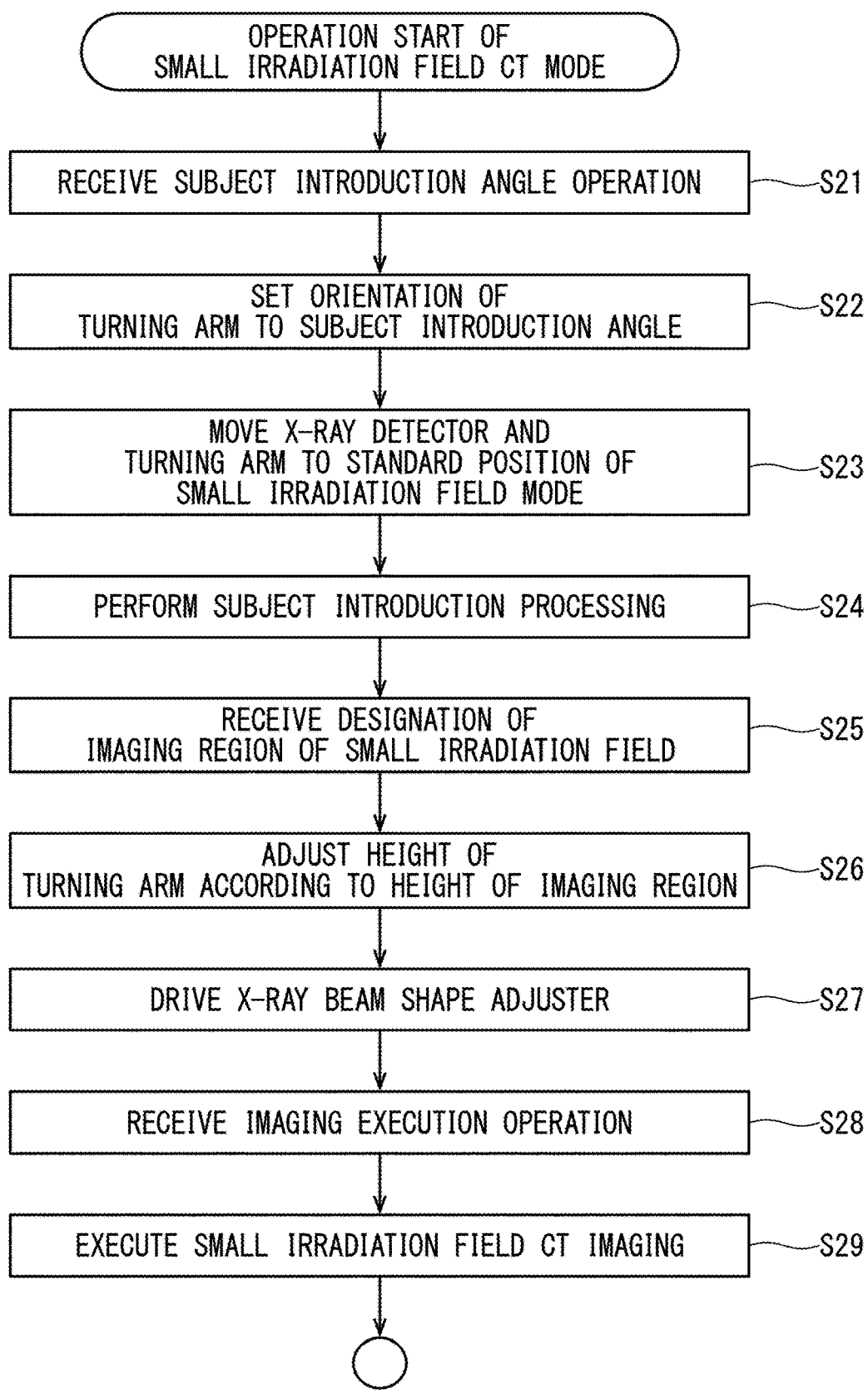
FIG. 19 is a flowchart illustrating the operation in a small irradiation field CT mode.
Figure 20:
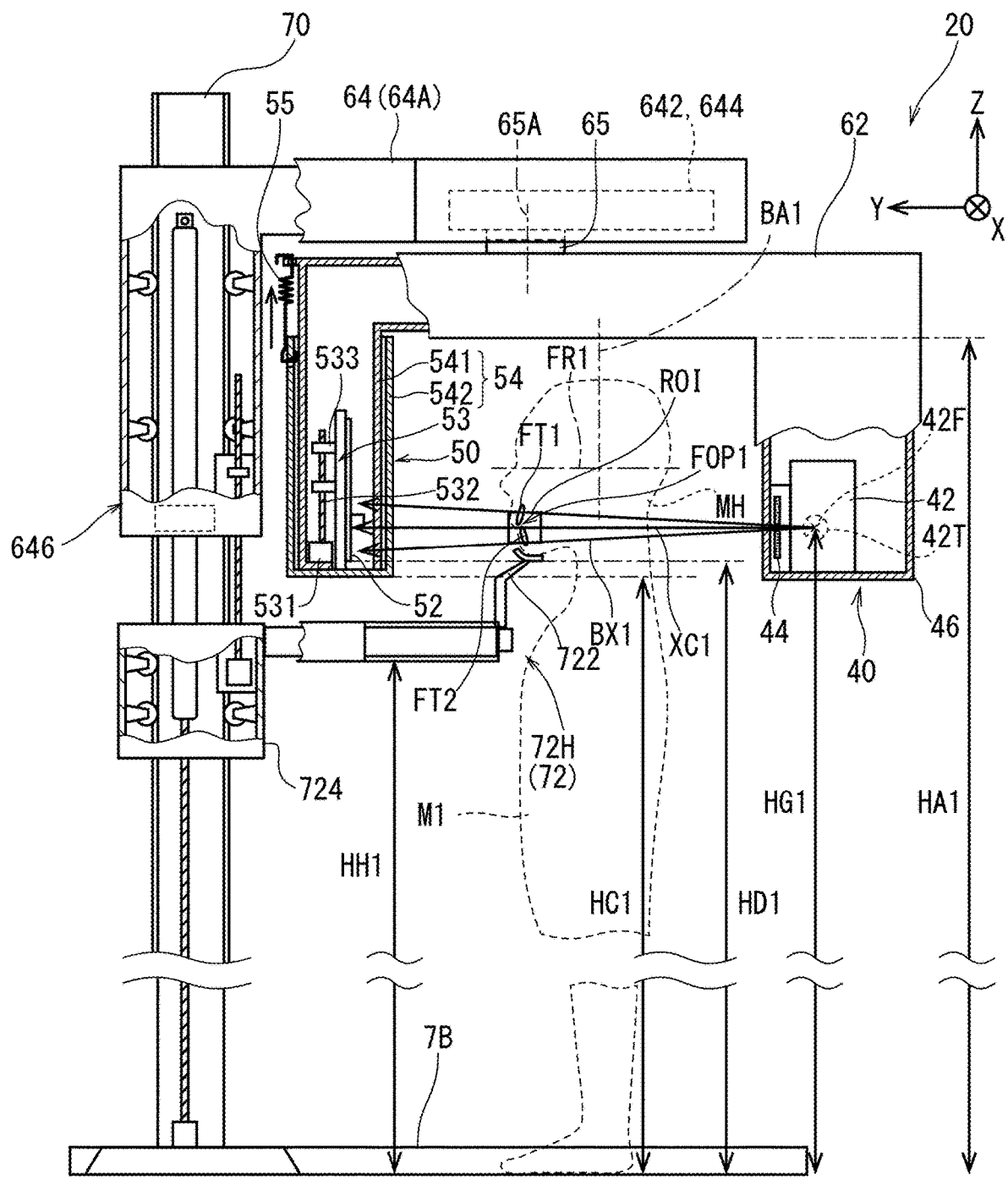
FIGS. 20 to 22 are side views illustrating the imaging unit 20 in the small irradiation field CT mode.
Figure 21:
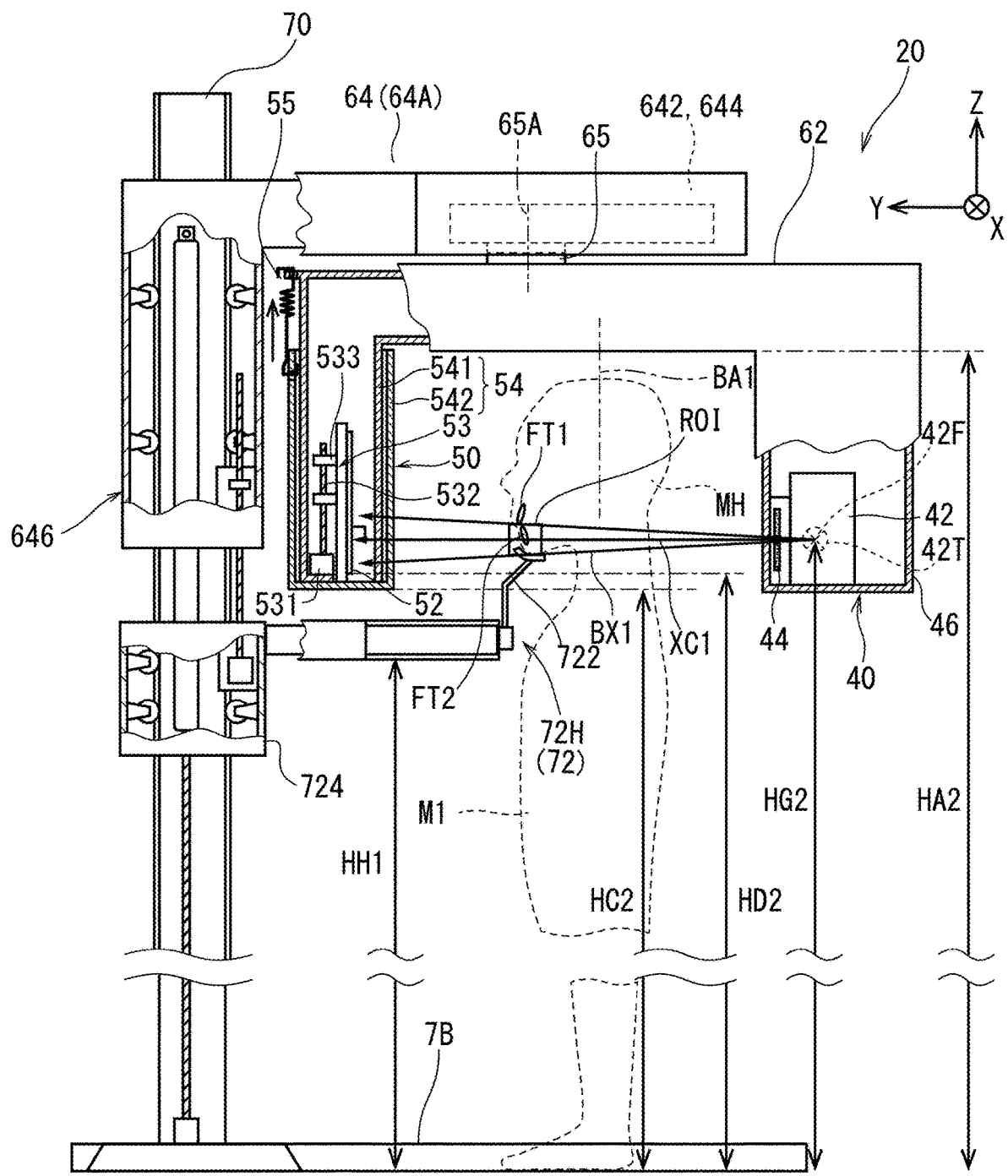
Figure 22:
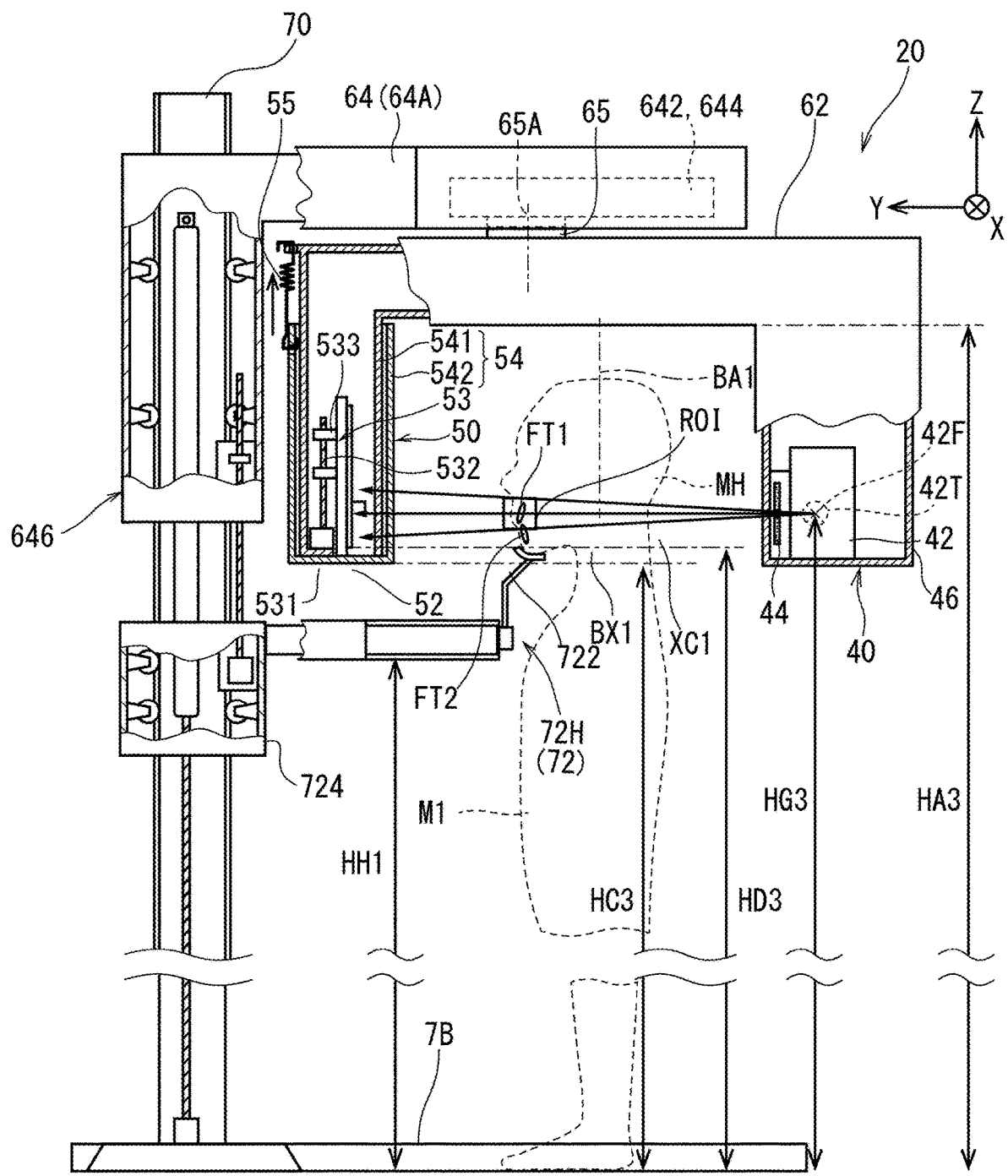

FIG. 19 is a flowchart illustrating the operation in the small irradiation field CT mode. FIGS. 20 to 22 are side views illustrating the imaging unit 20 in the large irradiation field CT mode. As described above, the small irradiation field CT mode is a mode in which a relatively small region (for example, a diameter of 40 mm and a height of 40 mm) is set to the imaging region. In the example of FIG. 20, front teeth FT1, FT2 of the small upper and lower jaws are set to the imaging region ROI. In the example of FIG. 21, the front teeth FT2 of the lower jaw are set to the imaging region ROI. In the example of FIG. 22, the front teeth FT1 of the upper jaw are set to the imaging region ROI. In the following description, unless otherwise noted, it is assumed that the subject M1 has a standard skeleton.

When the small irradiation field CT mode is started, the designation of the subject introduction angle is received (step S21). The subject introduction angle is an angle (orientation) of the turning arm 62 when the subject M1 is introduced between the X-ray generating unit 40 and the X-ray detecting unit 50. The operator introduction angle is specified by the manipulator through, for example, the operation display unit 82. For example, the manipulator may select a desired subject introduction angle from among a plurality of angles as one mode realizing the designation.

For example, the subject introduction angle may be an angle that is inclined with respect to the Y-axis direction (an angle parallel to a combination direction of the X-axis direction and the Y-axis direction). Specifically, as illustrated in FIG. 2, from the state in which the X-ray detecting unit 50 and the X-ray generating unit 40 are arranged in parallel along the Y-axis direction, for example, the X-ray detecting unit 50 is rotated to the −X side and the X-ray generating unit 40 is rotated to the +X side. In this case, with respect to the space between the pair of forehead rods opened to the −Y side of the head holder 723, the subject M1 can easily be accessed from the space (the space on the −X side of the X-ray generating unit 40) on the lateral side (−X side) of the X-ray generating unit 40. The subject introduction angle may be an angle at which the turning arm 62 is parallel to the Y-axis direction.

In the case that the subject M1 sitting on the wheelchair is introduced into the X-ray imaging apparatus 10, the subject introduction angle is preferably set to an angle at which the turning arm 62 is parallel to the X-axis direction. Consequently, the subject M1 sitting on the wheelchair travels straight toward the subject holder 72 (head holder 72H), which allows the subject M1 to be introduced into the X-ray imaging apparatus 10.

When the subject introduction angle is designated in step S21, the orientation of the turning arm 62 is matched with the designated subject introduction angle (step S22). Specifically, the support drive controller 802 drives the turning motor 6421 according to information about the subject introduction angle input through the operation display 82, and adjusts the orientation of the turning arm 62.

Subsequently, the X-ray detector 52 and the turning arm 62 are moved to the standard position corresponding to the small irradiation field CT mode (step S23).

In particular, the support drive controller 802 moves the turning arm 62 (support) to a standard height position corresponding to the small irradiation field CT mode. The standard height position is a height position where a center beam XC1 that is the center (optical axis) of the X-ray cone beam BX1 is incident on a front tooth occlusal position FOP1 in the head MH while the head MH of the standard skeleton is assumed to be held by the subject holder 72 (see FIG. 20). The front tooth occlusal position FOP1 is an intermediate height position between the upper end of the lower end of the front tooth (middle incisor or lateral incisor) of the upper jaw and the upper end of the front tooth (middle incisor tooth or lateral incisor) of the lower jaw when the upper and lower jaws of the standard MH that is the standard skeleton are engaged with each other. In this case, the center beam XC1 is the X-ray emitted horizontally from a focal point 42F (X-ray generation point) of the X-ray generator 42. In this case, the X-ray generator 42 is installed such that a main line (the X-ray having the highest intensity) of the X-ray is horizontally emitted. Strictly the focal point 42F is not a point but a surface.

In the small irradiation field CT mode in FIGS. 20 to 22 and the large irradiation field CT mode in FIG. 24 (to be described later), the center beam XC1 of the X-ray cone beam BX1 is orthogonally incident on a body axis BA1 passing through the head MH held by the subject holder 72. The center beam XC1 is perpendicularly incident on the detection surface of the X-ray detector 52.

As illustrated in FIG. 20, the X-ray detector drive controller 804 sets the height position (HD1) of the X-ray detector 52 such that the X-ray cone beam BX1 in which the center beam XC1 passes through the front tooth occlusal position FOP1 is incident as close as possible to the lower end of the detection surface of the X-ray detector 52. In FIG. 20, the X-ray detector drive controller 804 in FIG. 11 matches the X-ray incident position in the X-ray detector 52 at the lower end of the X-ray cone beam BX1 in which the center beam XC1 passes through the front tooth occlusal position FOP1 with the lower end (or a predetermined portion close to the lower end) of the detection surface of the X-ray detector 52. Consequently, the X-ray detector 52 is disposed at the position as high as possible, so that the lower end of the casing 54 can be rotated at the position (HC1) as high as possible during the X-ray imaging.

Subsequently, processing of introducing the subject M1 is performed (step S24). In particular, the manipulator performs a predetermined operation on the operation display 82 while the actual subject M1 is accommodated in the X-ray imaging apparatus 10. Consequently, the height position (HD1) of the subject holder 72 and the height position (HA1) of the turning arm 62 are adjusted according to the actual size of the subject M1.

Subsequently, the imaging region setting unit 801 receives the operation to designate the imaging region ROI, and sets the imaging region ROI (step S25). As illustrated in FIG. 17, the region setting screen W3 is displayed on the operation display 82 (or the display 32), and the manipulator operates the operation display 82 (or the operation unit 34), thereby setting the imaging region ROI.

Subsequently, the height position of the turning arm 62 with respect to the subject holder 72 is adjusted according to the height position of the imaging region ROI set in step S25 (step S26). In particular, the support drive controller 802 adjusts the height position of the turning arm 62, whereby the height position of the center beam XC1 is matched with the center of the set imaging region ROI.

Subsequently, the X-ray generating unit drive controller 806 drives the X-ray beam shape adjuster 44 (44A) such that the X-ray beam shape adjuster 44 (44A) shapes the X-ray beam suitable for the imaging region ROI as illustrated in FIGS. 7 and 9 (step S27). Consequently, in the case that the X-ray generator 42 emits the X-ray, the X-ray beam shape adjuster 44 (44A) shapes the X-ray cone beam BX1 suitable for the imaging region ROI of the small irradiation field.

Subsequently, the imaging execution operation is received (step S28). Specifically, the operation to execute the imaging (CT imaging) is received by operating an X-ray irradiation switch 85 connected to the operation display 82.

When the imaging execution operation is received in step S28, the main body controller 80 controls each element of the imaging unit 20 to execute the CT imaging on the imaging region ROI of the small irradiation field (step S29). At this point, the imaging at 180 degrees and the imaging at 360 degrees can be selected in the CT imaging. For the CT imaging at 180 degrees, an imaging time is shorter than that of the CT imaging at 360 degrees, and the exposure dose can be reduced. For the 360-degree CT imaging, the imaging time and the irradiation dose are larger than those of the 180-degree CT imaging, but a clearer image can be obtained.

As illustrated in FIG. 20, in the small irradiation field CT mode, the height position (HD1) of the X-ray detector 52 is set such that the X-ray cone beam BX1 is received on the lower end side of the detection surface of the X-ray detector 52. Consequently, the X-ray detector 52 can be disposed at the high position, so that the outer box 542 can be disposed at the high position. Thus, the X-ray detecting unit 50 can smoothly be turned around the subject M1 without any trouble.

The height position of each element will be described below. A height HA1 of the bottom surface of the turning arm 62 located above the subject, a height HG1 of the X-ray generator 42 (in particular, the height of the focal point 42F of the X-ray tube 42T included in the X-ray generator 42), a height HC1 of the bottom surface of the casing 54 (in particular, the outer box portion 542) of the X-ray detecting unit 50, a height HD1 of the bottom surface of the X-ray detector 52, and a height HH1 of the bottom surface of the subject holder 72 are defined as illustrated in FIG. 20.

In the examples of FIGS. 20 to 22, the subjects M1 are identical. For this reason, the heights HH1 of the bottom surface of the subject holder 72 are matched with one another. When the height of the subject varies, the height of the bottom surface of the subject holder 72 can appropriately be changed.

The imaging region ROI in FIG. 21 is set to the front teeth FT2 of the lower jaw, so that the imaging region ROI in FIG. 21 is located lower than the imaging region ROI in FIG. 20. Thus, a height HA2 of the bottom surface of the turning arm 62, a height HG2 of the X-ray generator 42, a height HC2 of the bottom surface of the casing 54, and a height HD2 of the bottom surface of the X-ray detector 52 in FIG. 21 are set lower than the respective heights HAL HG1, HC1, HD1 in FIG. 20.

The imaging region ROI in FIG. 22 is set to the front teeth FT1 of the upper jaw, so that the imaging region ROI in FIG. 22 is higher than the imaging region ROI in FIG. 20. Thus, a height HA3 of the bottom surface of the turning arm 62, a height HG3 of the X-ray generator 42, a height HC3 of the bottom surface of the casing 54, and a height HD3 of the bottom surface of the X-ray detector 52 in FIG. 22 are set higher than the respective heights HAL HG1, HC1, HD1 in FIG. 20.

<Large Irradiation Field CT Mode>

Figure 23:
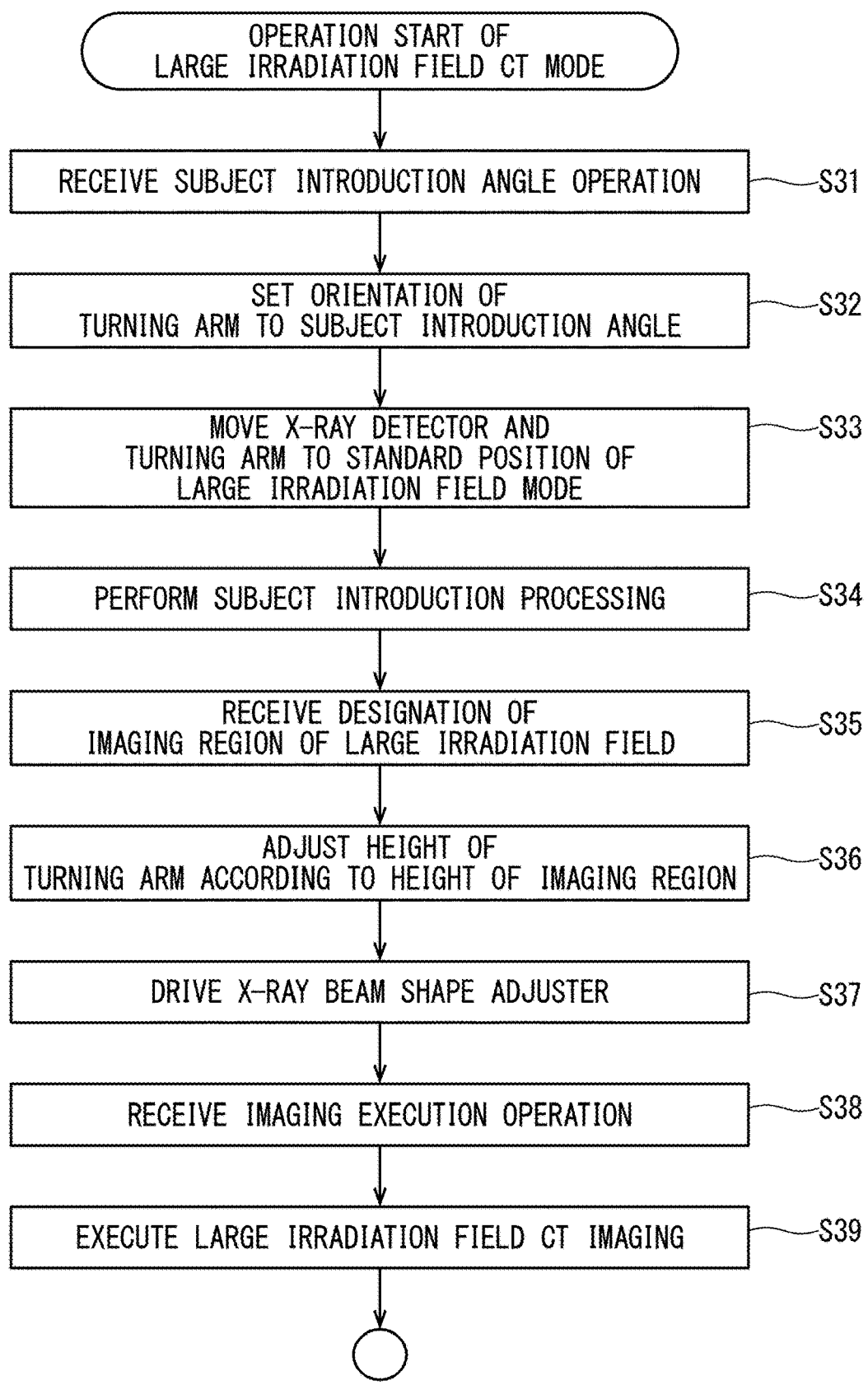
FIG. 23 is a flowchart illustrating the operation in a large irradiation field CT mode.

FIG. 23 is a flowchart illustrating the operation in the large irradiation field CT mode. FIG. 24 is a schematic side view illustrating the imaging unit 20 in the large irradiation field CT mode. In the large irradiation field CT mode, as described above, a relatively large region (for example, a diameter of 80 mm and a height of 80 mm) is set to the imaging region.

When the large irradiation field CT mode is started, the designation of the subject introduction angle is received (step S31). The orientation of the turning arm 62 is matched with the designated subject introduction angle (step S32). Steps S31, S32 have the same processing content as steps S21, S22 in FIG. 19.

Subsequently, the X-ray detector 52 and the turning arm 62 are moved to the standard position corresponding to the large irradiation field CT mode (step S33).

The standard height position of the turning arm 62 in the large irradiation CT mode is similar to the standard height of the small irradiation field CT mode. That is, in the case that the head MH of the standard skeleton is held by the subject holder 72, the height position is set such that is the center beam XC1 of the X-ray cone beam BX1 is incident on the front tooth occlusal position FOP1 in the head MH.

Figure 24:
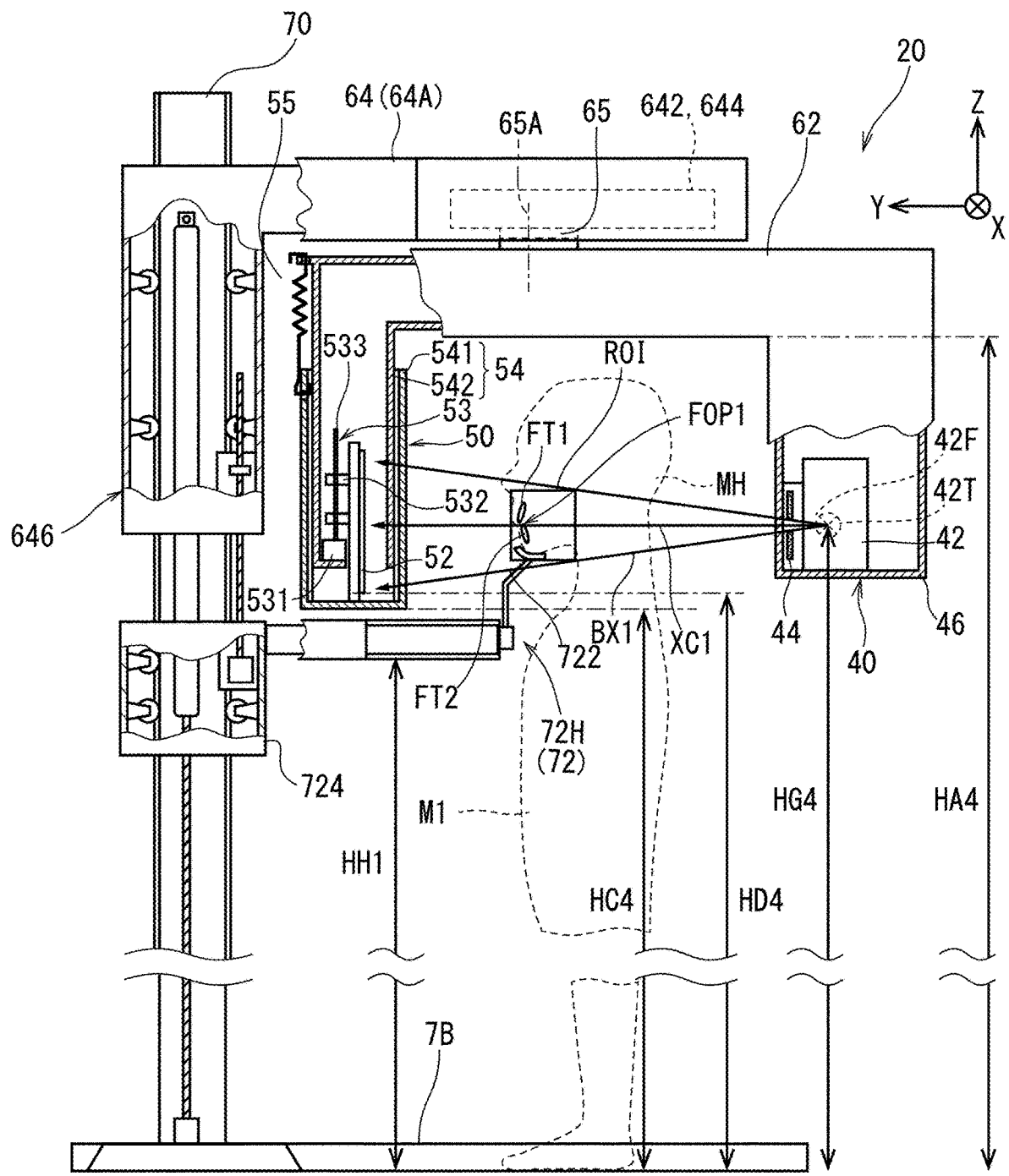
FIG. 24 is a side view illustrating the imaging unit 20 in the large irradiation field CT mode.

As illustrated in FIG. 24, a height HD4 of the bottom surface of the X-ray detector 52 is set to the position where the X-rays at the upper and lower ends of the X-ray cone beam BX1 in which the center beam XC1 passes through the front tooth occlusion position FOP1 can be incident on the X-ray detector 52. In this case, the incident position of the lower end of the X-ray cone beam BX1 at the X-ray detector 52 is matched with the lower end (or a predetermined portion near the lower end) of the detection surface of the X-ray detector 52. Consequently, the X-ray detector 52 is disposed at the position as high as possible, so that the lower end of the casing 54 can be rotated at the position as high as possible during the X-ray imaging.

Subsequently, the subject introduction processing is performed (step S34). Step S34 has the same processing content as step S24 in FIG. 19.

Subsequently, the imaging region setting unit 801 receives the operation to designate the imaging region ROI, and sets the imaging region ROI (step S35).

Subsequently, the height position of the turning arm 62 with respect to the subject holder 72 is adjusted according to the height position of the imaging region ROI set in step S35 (step S36). In particular, the support drive controller 802 adjusts the height position of the turning arm 62, whereby the height position of the center beam XC1 is matched with the center of the set imaging region ROI.

Subsequently, the X-ray generating unit drive controller 806 drives the X-ray beam shape adjuster 44 such that the X-ray beam shape adjuster 44 shapes the X-ray beam suitable for the imaging region ROI (step S37). Consequently, in the case that the X-ray generator 42 emits the X-ray, the X-ray beam shape adjuster 44 shapes the X-ray cone beam BX1 suitable for the imaging region ROI of the large irradiation field.

Subsequently, the imaging operation is received (step S38). Specifically, in the operation display 82, the operation of the X-ray irradiation switch 85 is received to execute the CT imaging.

When the imaging execution operation is received in step S38, the main body controller 80 controls each element of the imaging unit 20 to execute the CT imaging on the imaging region ROI of the large irradiation field (step S39). For the large irradiation field CT imaging, the 180-degree imaging and the 360-degree imaging can be selected similarly to the small irradiation field CT imaging.

As illustrated in FIG. 24, in the large irradiation field CT mode, the spread at both the upper and lower ends with respect to the center beam XC1 is larger than that in the case of the small irradiation field CT mode. Consequently, a height HC4 of the casing 54 (outer box 542) and a height HD4 of the X-ray detector 52 in the large irradiation field CT mode are higher than the heights HC1, HD1 in the small irradiation field CT mode in FIG. 20, respectively. On the other hand, a height HA4 of the bottom surface of the turning arm 62 and a height HG4 of the X-ray generator 42 are matched with the heights HAL HG1.

<Medium Irradiation Field CT Mode>

In the middle irradiation field CT mode, the imaging region ROI is larger than that in the small irradiation field CT mode, and is smaller than in the large irradiation field CT mode. In this case, the height of the imaging region ROI is set to 40 mm that is the same as the imaging region ROI of the small irradiation field CT mode, and the diameter of the imaging region ROI is set to 80 mm that is the same as the imaging region ROI of the large irradiation field CT mode. The flowchart of the operation of the X-ray imaging apparatus 10 in the middle irradiation field CT mode is substantially identical to the flowchart in FIG. 19. The middle irradiation field CT mode is different from the small irradiation field CT mode in that the imaging region ROI of the middle irradiation field is set in step S25, and that the X-ray beam shape adjustment section 44 is driven according to the imaging region ROI of the middle irradiation field in step S27.

As illustrated in FIGS. 20 to 22 (small irradiation field CT mode) and FIG. 24 (large irradiation field CT mode), in the CT imaging of the X-ray imaging apparatus 10, the center beam XC1 of the X-ray cone beam BX1 with which the head MH of the subject M1 is irradiated is perpendicularly incident on the body axis BA1 passing through the head MH. In this case, the body axis BA1 extends in the vertical direction, and the center beam XC1 is parallel to the horizontal direction. Hereinafter, an irradiation mode of the X-ray cone beam BX1 in which the center beam XC1 becomes horizontal is referred to as horizontal irradiation.

When metal is contained in the imaging region ROI, sometimes the radial artifact (metal artifact) is generated in the CT image. At this point, the artifact also tends to appear obliquely and radially as an inclination of the X-ray increases with respect to the metal. On the other hand, in the first preferred embodiment, the X-ray cone beam BX1 is subjected to the horizontal irradiation in which the center beam XC1 is perpendicularly incident on the detection surface. Consequently, each X-ray is incident perpendicularly or nearly perpendicularly on the detection surface, so that the oblique and radial appearance of the artifact can be reduced even if the metal exists in the imaging region ROI. Thus, the image quality of the CT image can be expected to be improved by the CT imaging of the horizontal irradiation.

In the first preferred embodiment, the center beam XC1 is the main line of the X-ray emitted in the horizontal direction. The vicinity of the center portion of the imaging region ROI is irradiated with the X-ray having the relatively high intensity by the incidence of the center beam XC1 on the center in the height direction of the imaging region ROI. Therefore, the manipulator sets the imaging region ROI such that the region of interest becomes the center of the imaging region ROI, which allows the manipulator to acquire the high-clearness CT image with respect to the region of interest.

<Entire Jaw Panoramic Mode>

Figure 25:
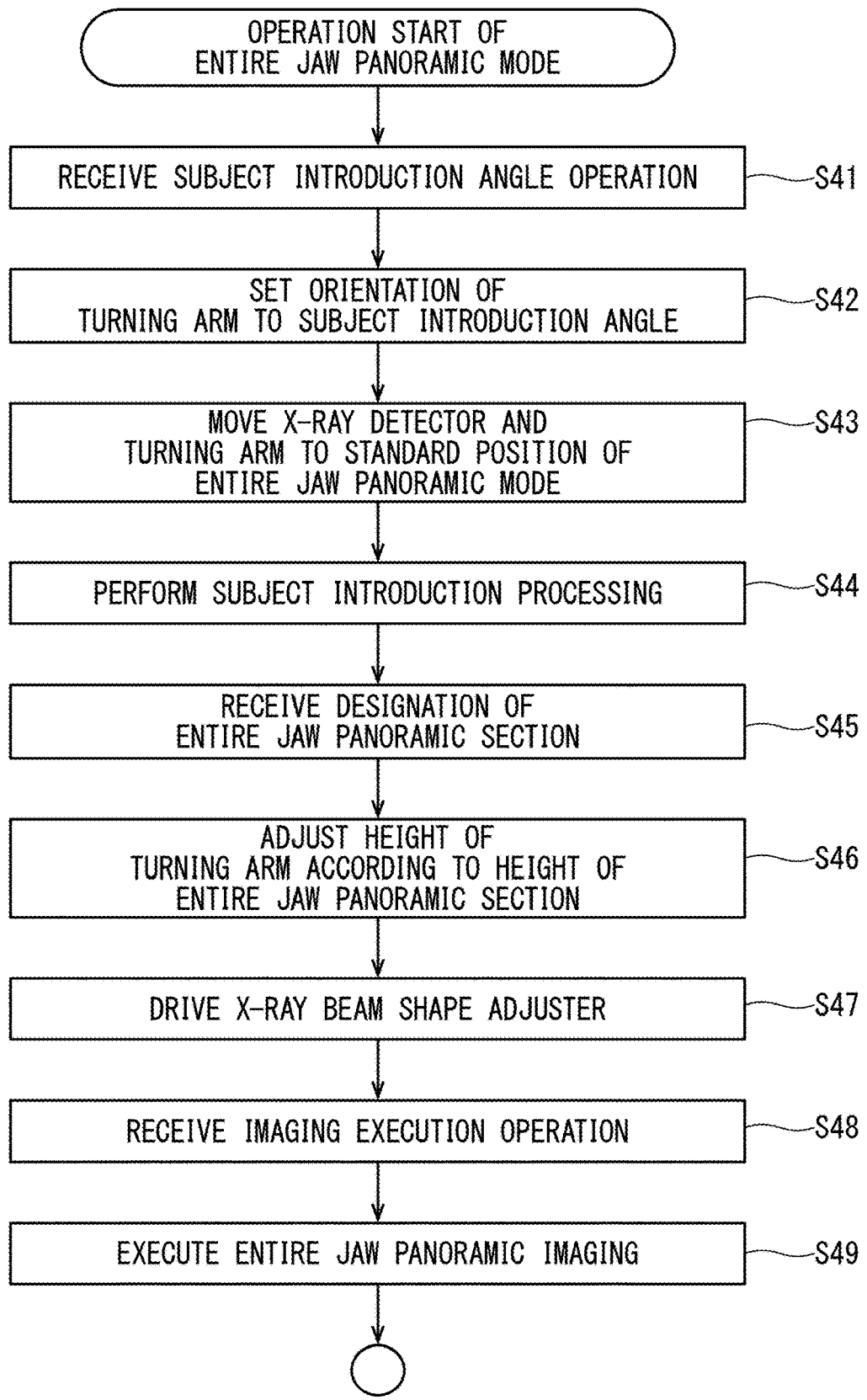
FIG. 25 is a flowchart illustrating the operation in an entire jaw panoramic mode.
Figure 26:
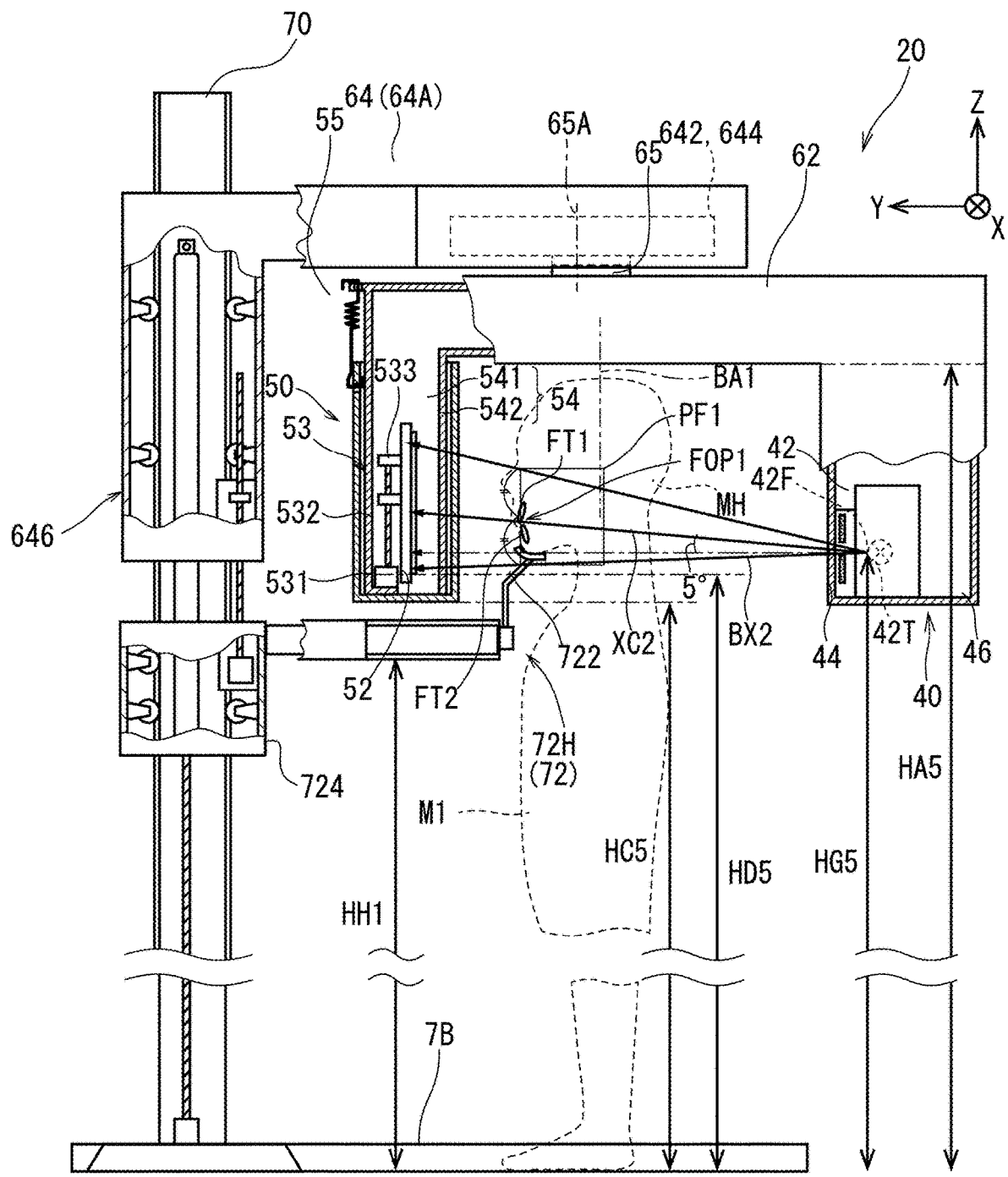
FIGS. 26 and 27 are side views illustrating the imaging unit 20 in the entire jaw panoramic mode.

FIG. 25 is a flowchart illustrating the operation in the entire jaw panoramic mode. FIG. 26 is a side view illustrating the imaging unit 20 in the entire jaw panoramic mode. As described above, the entire jaw panoramic mode is a mode in which the panoramic imaging is executed on the section across the entire jaw (all the teeth and the upper and lower jaw bones including the temporomandibular joint).

When the entire jaw panoramic mode is started, the designation of the subject introduction angle is received (step S41). Then, the orientation of the turning arm 62 is matched with the designated subject introduction angle (step S42). Steps S41, S42 have the same processing content as steps S21, S22 in FIG. 19.

Subsequently, the X-ray detector 52 and the turning arm 62 are moved to the standard position corresponding to the entire jaw panoramic mode (step S43).

As illustrated in FIG. 26, it is assumed that the standard height position of the turning arm 62 in the entire jaw panoramic mode is the height position where the center beam XC2 is incident on the center position (in this case, the front tooth occlusal position FOP1) in the height direction of the front tooth side of the entire jaw panoramic section PF1 (in this case, the standard-size entire jaw panoramic section PF1) in the head MH while the height position where the head MH of the standard skeleton is held by the subject holder 72. The entire jaw panoramic section PF1 in FIG. 26 has a rectangular shape as viewed from the side. When viewed from above, like a dental arch D1 in FIG. 16, the entire jaw panoramic section PF1 is curved into a substantially horseshoe shape that spreads rearward along tooth rows on both sides from the front teeth FT1, FT2 in the center of the tooth row. The entire jaw panoramic section PF1 is an example of a panoramic section (or panoramamic layer) PF.

In the panoramic mode, the center beam XC2 is incident on the entire jaw panoramic section PF1 and the X-ray detector 52 upward from below with respect to the horizontal direction. In this case, for example, the center beam XC2 is inclined by 5 degrees with respect to the horizontal plane (XY plane). That is, in the panoramic mode, the object M1 is irradiated with the X-ray narrow beam BX2 at the shooting-up angle of 5°. The center beam XC2 is incident upward from below with respect to body axis BA1. Hereinafter, such an irradiation mode of the X-ray narrow beam BX2 is referred to as shooting-up irradiation.

As illustrated in FIG. 26, the standard height position of the X-ray detector 52 is set to a height position capable of receiving the X-ray narrow beam BX2 emitted at the shooting-up angle of 5 degrees. In this case, in the standard height position of the X-ray detector 52, the X-ray detector 52 is disposed such that the lower-end beam of the X-ray narrow beam BX2 is incident on the portion close to the lower end (in this case, the lowermost end) of the detection surface of the X-ray detector 52. Consequently, in the panorama mode, the X-ray detector 52 and the outer box 542 can be disposed as high as possible. For this reason, the lower end of the outer box 542 can be rotated at the position as high as possible.

When the X-ray detector 52 and the turning arm 62 are moved to the standard position, the subject introduction processing is performed (step S44). Step S44 has the same processing content as step S24.

Subsequently, the imaging region setting unit 801 receives the operation to designate the imaging region ROI, and sets the imaging region ROI (step S45). In the entire jaw panoramic mode, the imaging region ROI is set to the entire jaw panoramic section PF1.

Subsequently, the height position of the turning arm 62 with respect to the subject holder 72 is adjusted according to the imaging region ROI (entire jaw panoramic section PF1) set in step S45 (step S46). In particular, the support drive controller 802 sets the height position of the turning arm 62 to the height at which the center beam XC2 emitted upward passes through the center position on the front tooth side of the set entire jaw panoramic section PF1.

Subsequently, the X-ray generating unit drive controller 806 drives the X-ray beam shape adjuster 44 such that the X-ray beam shape adjuster 44 shapes the X-ray narrow beam BX2 suitable for the entire jaw panoramic section PF1 that is the imaging region (step S47). Consequently, in the case that the X-ray generator 42 emits the X-ray, the X-ray narrow beam BX2 having a height width suitable for the entire jaw panoramic section PF1 is formed by the X-ray beam shape adjuster 44.

Subsequently, the imaging execution operation is received (step S48). Specifically, the operation display 82 receives the operation to execute the panoramic imaging. When the imaging execution operation is received in step S48, the main body controller 80 controls each element of the imaging unit 20 to execute the panoramic imaging on the entire jaw panoramic section PF1 (step S49).

As illustrated in FIG. 26, in the entire jaw panoramic mode, a height HA5 of the bottom surface of the turning arm 62 is lower than the height HA4 in the large irradiation field CT mode of FIG. 24. That is, in the X-ray imaging apparatus 10, the turning arm 62 (support) in the CT mode is positioned on the upper side in the vertical direction as compared with the panoramic mode. In this way, in the X-ray imaging apparatus 10, the horizontal irradiation of the X-ray cone beam BX1 is easily performed by positioning the turning arm 62 in the CT mode on the upper side as compared with the panoramic mode.

A height HG5 of the bottom surface of the X-ray generator 42 is lower than the height HG4 in the large irradiation field CT mode of FIG. 24. A height HC5 of the bottom surface of the casing 54 and a height HD5 of the bottom surface of the X-ray detector 52 are higher than the heights HC4, HD4 in the large irradiation field CT mode of FIG. 24, respectively. In the entire jaw panoramic mode, the difference between the height HC5 of the bottom surface of the casing 54 and the height HD5 of the X-ray detector 52 (the height width from the lower end of the casing 54 to the lower end of the X-ray detector 52) is larger than that in the large irradiation field CT mode.

Figure 27:
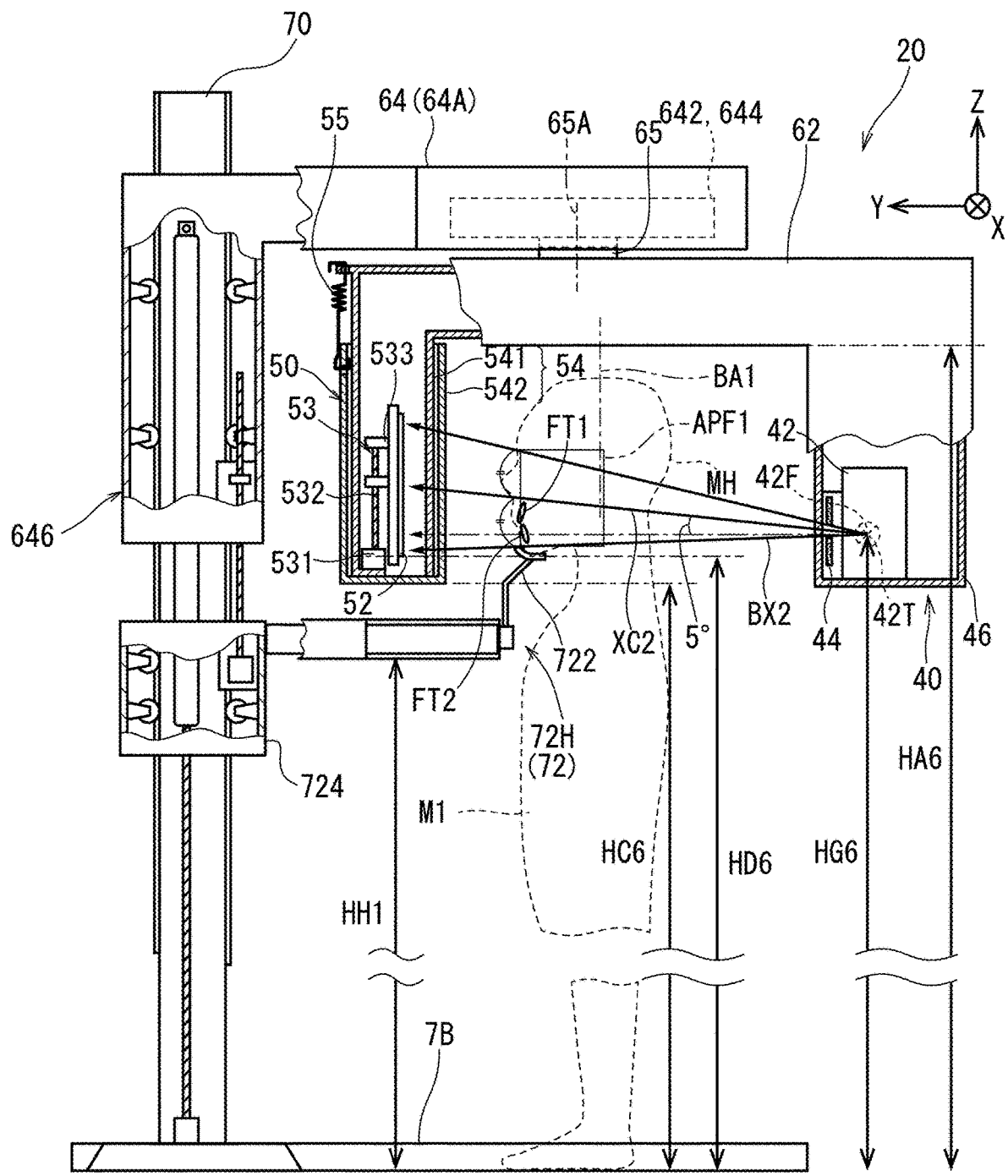

FIG. 27 is a side view illustrating the imaging unit 20 in the entire jaw panoramic mode. In FIG. 27, the entire jaw panoramic section PF1 is set above the position in FIG. 26. The entire jaw panoramic section PF1 is set above the tip of the jaw. For this reason, in the panoramic imaging, the panoramic image including the image of the upper region as compared with the case of the panoramic imaging in FIG. 26 is acquired although the tip of the jaw is cut.

When the height of each element in the case of FIG. 27 is compared to the case of FIG. 26, a height HA6 of the bottom surface of the turning arm 62, a height HG6 of the X-ray generator 42, a height HD6 of the bottom surface of the X-ray detector 52, and a height HC6 of the bottom surface of the casing 54 are higher than the respective heights HA5, HC5, HD5, HG5. In panoramic imaging of FIG. 27, in step S44 (subject introduction processing), the turning arm 62 and the X-ray detector 52 are elevated from the height in FIG. 26 immediately after the introduction of the actual subject M1 to the height in FIG. 27.

<Partial Panoramic Mode>

Figure 28:
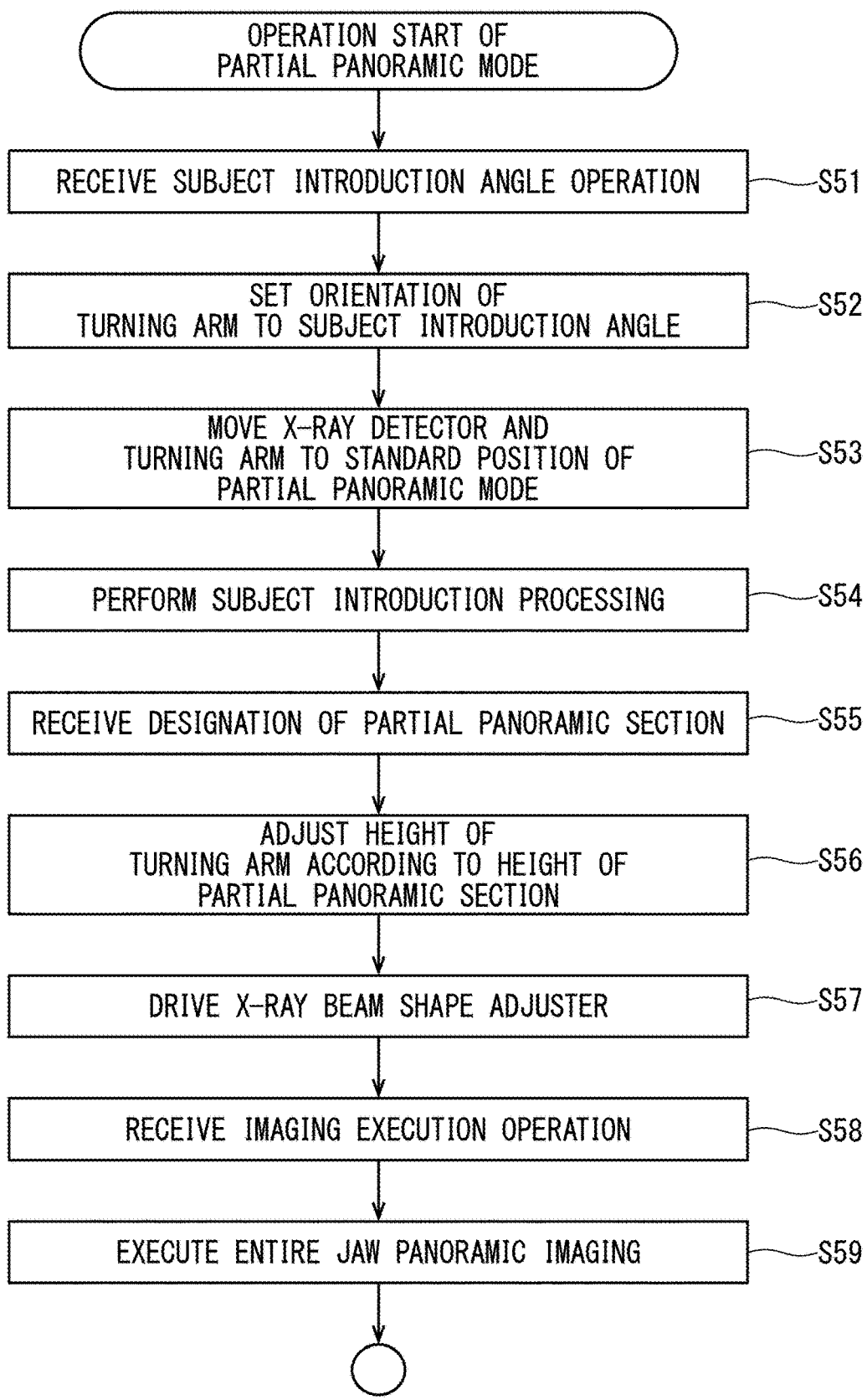
FIG. 28 is a flowchart illustrating the operation in the partial panoramic mode.
Figure 29:
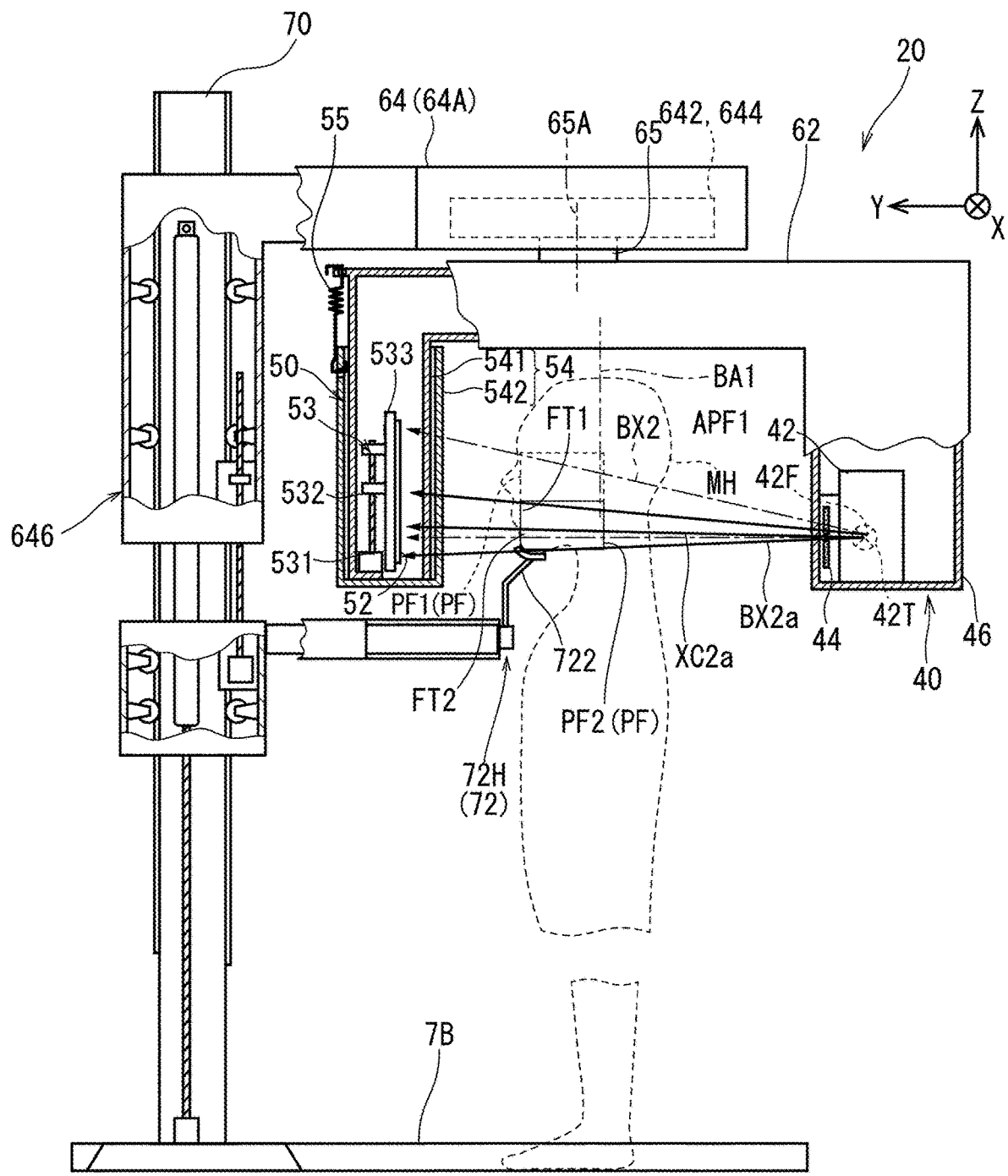
FIG. 29 is a side view illustrating the imaging unit 20 in a partial panorama.

FIG. 28 is a flowchart illustrating the operation in the partial panoramic mode. FIG. 29 is a side view illustrating the imaging unit 20 in the partial panorama. In the partial panoramic mode, a partial panoramic section PF2 that is a part of the entire jaw panoramic section PF1, which is the imaging region in the entire jaw panoramic mode, is set to the imaging region. In FIG. 29, the partial panoramic section PF2 is set over the lower jaw of a lower half in the entire jaw panoramic section PF1. The partial panoramic section PF2 is an example of the panoramic section PF.

As illustrated in FIG. 28, when the partial panoramic mode is started, the setting of the subject introduction angle is received (step S51). Subsequently, the orientation of the turning arm 62 is matched with the designated subject introduction angle (step S52). Steps S51, S52 have the same processing content as steps S21, S22 in FIG. 19.

Subsequently, the X-ray detector 52 and the turning arm 62 are moved to the standard position corresponding to the partial panoramic mode (step S53). At this point, the standard position corresponding to the partial panoramic mode is matched with the standard position of the entire jaw panoramic mode in step S43. The entire jaw panoramic mode and the partial panoramic mode may be different from each other in the standard positions of the X-ray detector 52 and the turning arm 62.

When the X-ray detector 52 and the turning arm 62 are moved to the standard position, the subject introduction processing is performed (step S54). Step S54 has the same processing content as step S24.

Subsequently, the imaging region setting unit 801 receives the operation to designate the partial panoramic section PF2 that is the imaging region in the partial panoramic mode, and sets the partial panoramic section PF2 (step S55). Specifically, as described in FIGS. 13 to 15, the mode setting screen W1 or the region setting screen W2 is displayed on the operation display 82 (or the display 32), and the manipulator operates the operation display 82 (or the operation unit 34), thereby setting the partial panoramic section PF2.

Subsequently, the height position of the bottom surface of the turning arm 62 is adjusted with respect to the subject holding unit 72 according to the height position of the partial panoramic section PF2 set in step S55 (step S56). At this point, the entire jaw panoramic section PF1 is assumed to be an origin of the partial panoramic section PF2, and the height position of the bottom surface of the turning arm 62 is set to the height position where the center beam XC1 is incident on the center position (in this case, the front tooth occlusal position) in the height direction on the front tooth side of the entire jaw panoramic section PF1.

Subsequently, the X-ray generating unit drive controller 806 drives the X-ray beam shape adjuster 44 such that the X-ray beam shape adjuster 44 forms an X-ray narrow beam BX2a suitable for the partial panoramic section PF2 (step S57). Consequently, in the case that the X-ray generator 42 emits the X-ray, the X-ray narrow beam BX2a having the height width suitable for the partial panoramic section PF2 is formed by the X-ray beam shape adjuster 44. In FIG. 29, the partial panoramic section PF2 is the lower half of the entire jaw panoramic section PF1, so that the X-ray narrow beam BX2a is formed by shielding the upper half of the X-ray narrow beam BX2 using the shielding member 441 (see FIG. 7).

Subsequently, the imaging execution operation is received (step S58). Specifically, the operation display 82 receives the operation to execute the panoramic imaging. When the imaging execution operation is received in step S58, the main body controller 80 controls each element of the imaging unit 20 to execute the panoramic imaging on the entire jaw panoramic section PF1 (step S59).

In the partial panoramic mode, a turning range of the turning arm 62 is decided according to the set partial panoramic section PF2. For example, in the case that only the right half of the entire jaw panoramic section PF1 is set to the partial panoramic section PF2, the X-ray generator 42 turns on the rear left side of the head MH, and the X-ray detector 52 turns on the front right side of the head MH. The rotation angle of the turning arm 62 is set to a half of the angle at which the entire jaw panoramic section PF1 is imaged.

Figure 30:
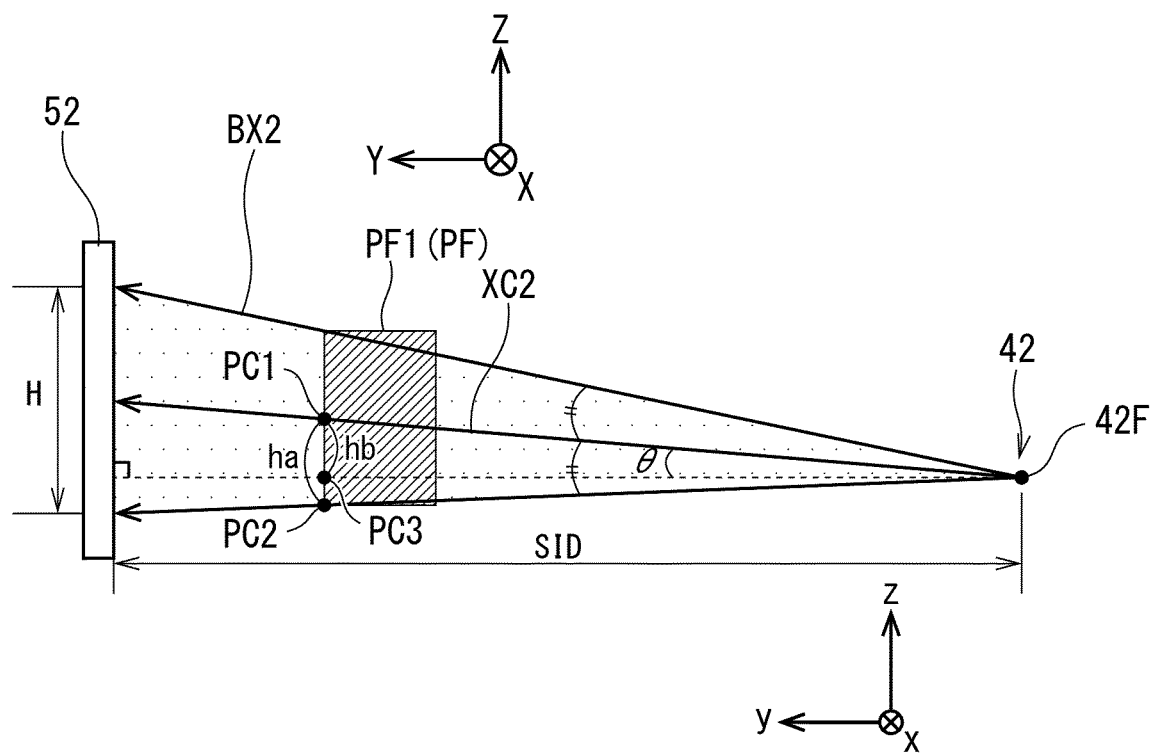
FIG. 30 is a schematic side view illustrating a state in which an entire jaw panoramic section PF1 is irradiated with an the X-ray narrow beam BX2 while the X-ray narrow beam BX2 is shot up.

FIG. 30 is a schematic side view illustrating a state in which the entire jaw panoramic section PF1 is irradiated with the X-ray narrow beam BX2 while the X-ray narrow beam BX2 is shot up. As illustrated in FIG. 30, the center beam XC2 of the X-ray narrow beam BX2 is incident on the center (point PC1) of the tip on the front tooth side in the entire jaw panoramic section PF1. Where θ is the shooting-up angle of the X-ray narrow beam BX2 (the angle at which the center beam XC2 is inclined with respect to the horizontal line). H is a vertical width when the X-ray narrow beam BX2 is incident on the X-ray detector 52. ha is a height dimension from the point PC1 through which the center beam XC2 passes to a point PC2 through which the lower end of the X-ray narrow beam BX2 passes at the tip on the front tooth side of the entire jaw panoramic section PF1, and hb is a height dimension from a point PC3 (the point through which the X-ray incident perpendicularly on the detection plane of the X-ray detector 52 passes in the entire jaw panoramic section PF1) through which the horizontal line extending from the focal point 42F passes to the point PC1. m is a magnification ratio (a ratio of a distance from the focal point 42F to the panoramic section with respect to the distance SID from the focal point 42F to an image receiving surface of the X-ray detector 52). Consequently, the following equation (1) is established.

$$hb=(SID/m)\tan \theta \quad (1)$$

For the panoramic imaging, the height dimension ha desirably ranges from 50 mm to 70 mm in order to include the standard jaw tip to the hard palate, and the height dimension hb desirably ranges from 15 mm to 65 mm. In the case that this requirement is satisfied, the following inequality (2) is obtained from the equation (1).

$$15<(SID/m)\tan \theta <65 \quad (2)$$

The turning radius of the turning unit 67 increases when the SID increases, so that the X-ray imaging apparatus 10 occupies a large space. For this reason, the SID is preferably less than or equal to 900 mm. In the case that the SID is too small, the X-ray detector 52 (or the X-ray generator 42) is hardly turns. For this reason, the SID is preferably greater than or equal to 500 mm. The rotation radii of the X-ray generator and the X-ray detector necessary for the panoramic imaging or CT imaging of the jaw of the human head can satisfactorily be secured by setting the SID to the range of 500 mm to 900 mm.

As described above, strictly the focal point 42F is not a point but a surface having a slight spread. Consequently, as the enlargement ratio m increases, a blur increases according to the size of the focal point 42F in the projection image of the X-ray, and the sharpness is degraded. The enlargement ratio m is preferably decreased as small as possible. Empirically, the enlargement factor m in the panoramic shooting is desirably set to 1.2 to 1.3. In the X-ray imaging apparatus 10, the enlargement ratio m in the panoramic mode is decreased smaller than the enlargement factor m in the CT mode. Consequently, the image quality of the panoramic image can be improved. The enlargement factor m in the CT radiography may be the enlargement factor at the central part of the imaging region ROI (FOV) with respect to the path direction of X-ray.

In panoramic imaging, the shade obstacle due to the hard palate, the lower jaw corner, and the spine can be reduced on the panoramic image by the shooting-up irradiation of the imaging region ROI with the X-ray narrow beam BX2. From this viewpoint, for example, the shooting-up angle θ desirably ranges from 4 degrees to 8 degrees.

<Electric Cable 90>

Figure 31:
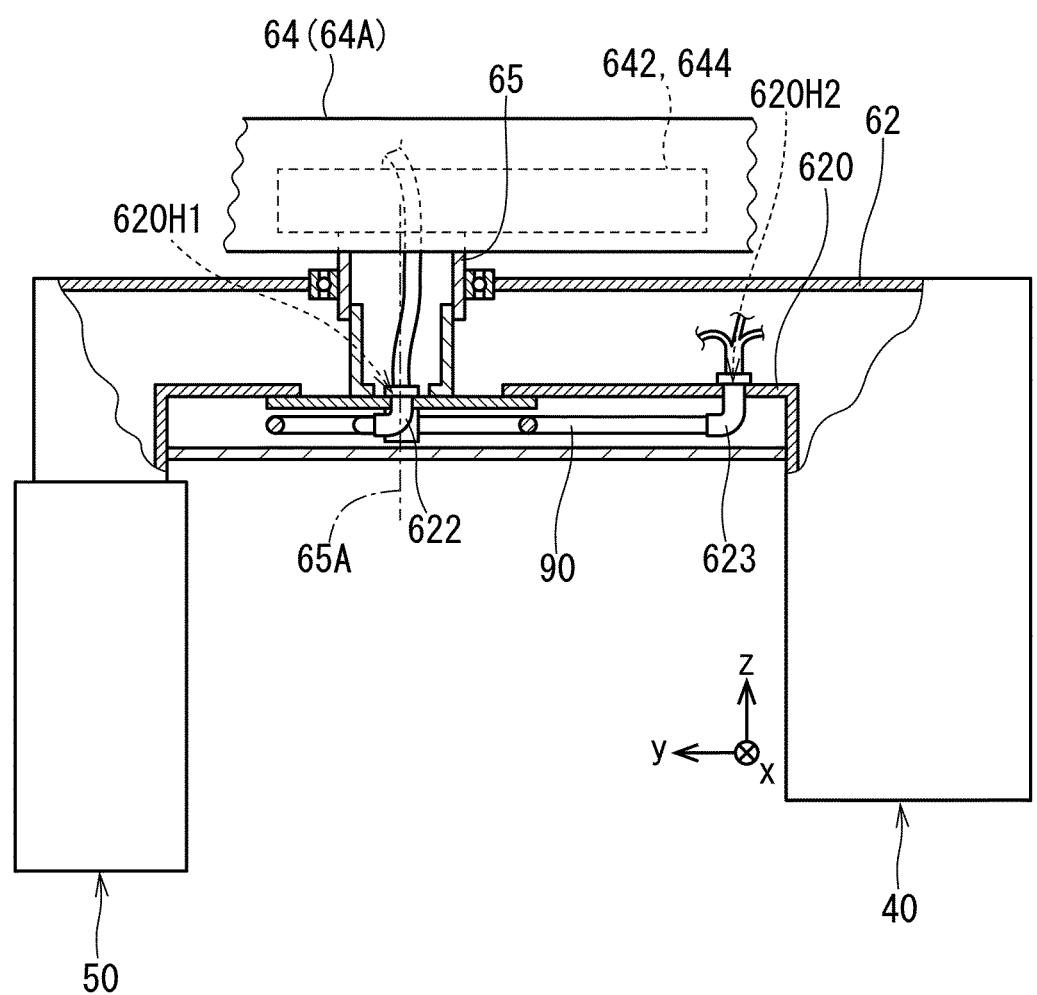
FIG. 31 is a side view illustrating an electric cable 90 routed in an upper frame 64, a rotation shaft 65, and a turning arm 62.
Figure 33:
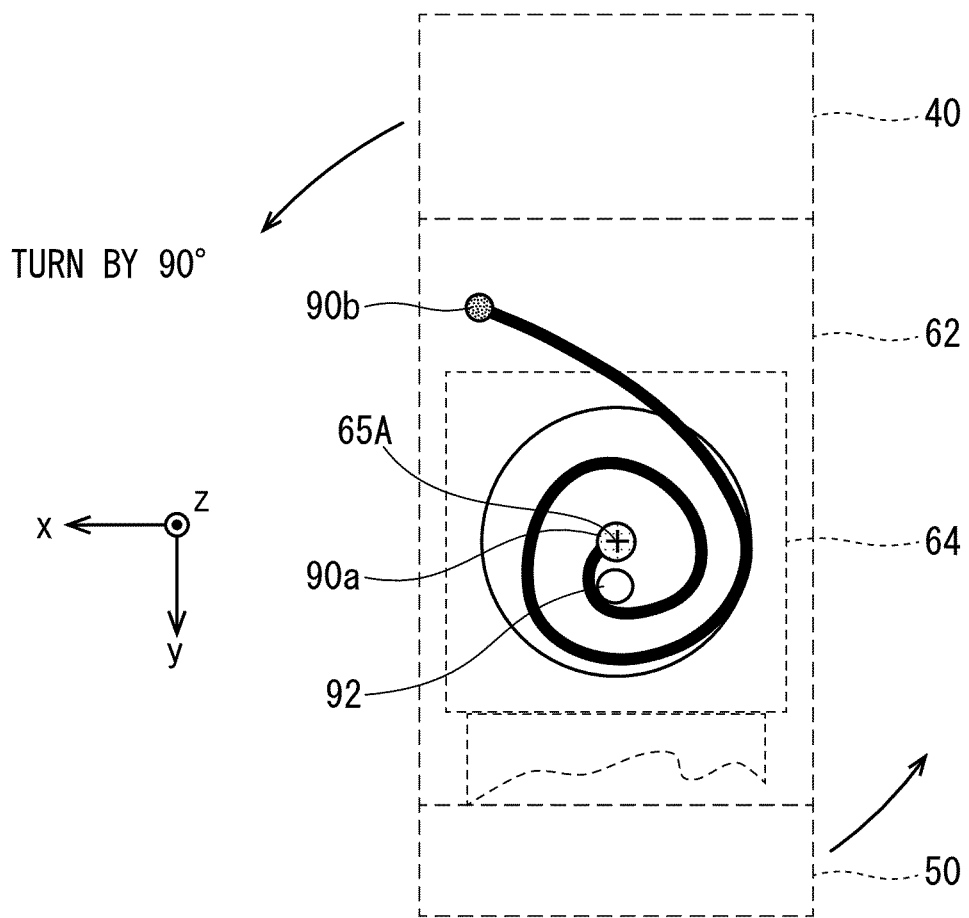
Figure 34:
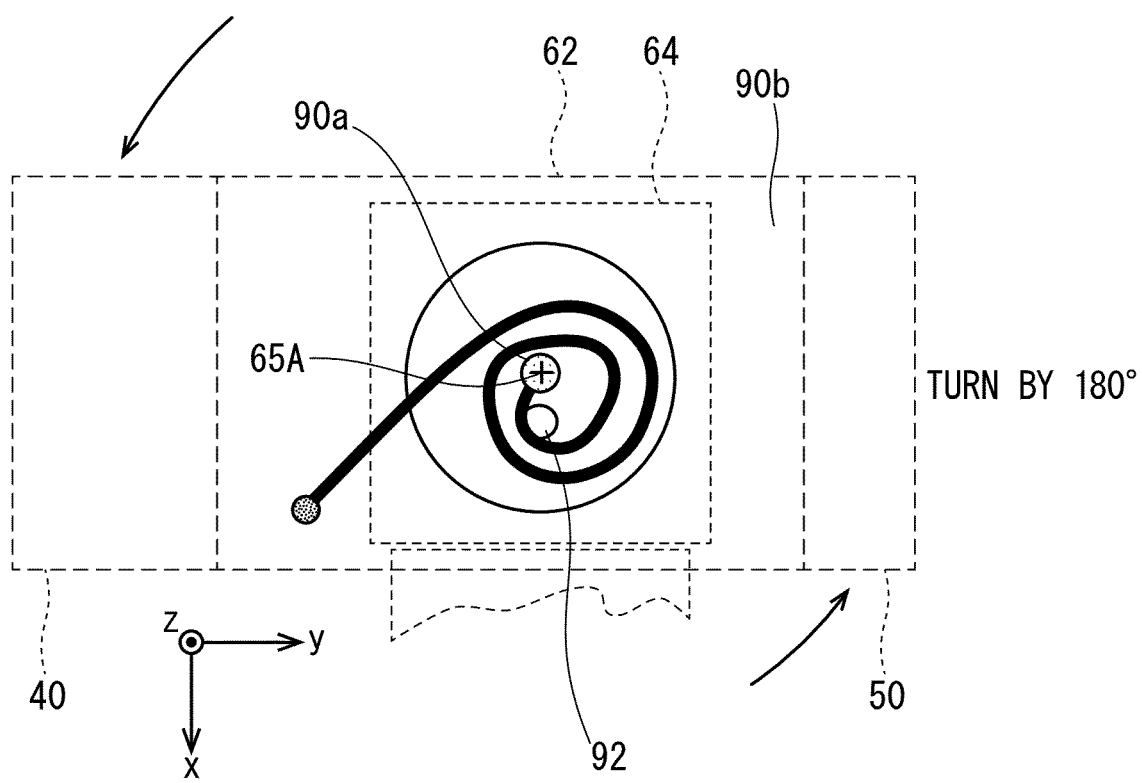

FIG. 31 is a side view illustrating the electric cable 90 routed in the upper frame 64, the rotation shaft 65, and the turning arm 62. FIGS. 32 to 34 are plan views illustrating the electric cable 90 in the turning arm 62 during rotation. FIG. 32 shows a state immediately after the turning arm 62 starts rotating, FIG. 33 shows a state in which the turning arm 62 has rotated 90 degrees from the state illustrated in FIG. 32, FIG. 34 shows a state in which it is rotated 180 degrees from the state illustrated in FIG. 32 Respectively.

As illustrated in FIG. 31, the rotation shaft 65 of the first preferred embodiment is a hollow member formed into a substantially cylindrical shape. The electric cable 90 is routed in the turning arm 62 through the inside of the upper frame 64 (bracket) and the inside of the rotation shaft 65. The electric cable 90 is constructed with an electric wire through which electric power is supplied to elements (such as the X-ray generator 42, the X-ray beam shape adjuster 44, the X-ray detector 52, the X-ray detector vertical movement driving unit 53) provided in the turning arm 62 or an electric wire through which electrical information communication is conducted between the element provided on the turning arm 62 and the main body controller 80.

As illustrated in FIG. 31, an accommodation unit 620 is provided in the turning arm 62. The electric cable 90 passing through the rotation shaft 65 enters the accommodation unit 620 from an opening 620H1, and is wound into a spiral shape so as to be outwardly away from the rotating axis line 65A in the accommodation unit 620. In the first preferred embodiment, the opening center of the opening 620H1 is matched with the rotation axis 65A. The electric cable 90 is exposed to the outside (however, in this case, the inside of the turning arm 62) from an opening 620H2 at a portion away (in this case, X-ray generating unit 40 side) from the rotation axis 65A of the accommodation unit 620, and branched toward each element.

In the first preferred embodiment, pipes 622, 623, which are formed into a tubular shape and bent substantially at right angles, are provided in the accommodation unit 620. One end of the pipe 622 is attached to an edge of the opening 620H1. The electric cable 90 is passed through the pipe 622 to enter the accommodation unit 620 along the vertical direction through the opening 620H1, and guided so as to extend in the horizontal direction along the pipe 622. One end of the pipe 623 is attached to an edge of the opening 620H2. By passing through the pipe 623, the electric cable 90 is bent in the vertical direction, and guided to the outside of the accommodation unit 620 through the opening 620H2.

In FIGS. 32 to 34, one end 90a of the electric cable 90 indicates a portion passing through the opening portion 620H1 (a portion opposed to an inner edge of the opening 620H1), the other end 90b of the electric cable 90 indicates the opening 620H2 (a portion opposed to an inner edge of the opening 620H2). Only the portion (the portion forming the spiral) accommodated in the accommodation unit 620 of the electric cable 90 is illustrated in FIGS. 32 to 34. As illustrated in FIGS. 32 to 34, an abutting member 92 extending in the vertical direction is provided in the accommodation unit 620. The abutting member 92 is formed into a rounded shape in which an outer peripheral surface has no corner. In this case the abutting member 92 is formed into a cylindrical shape. The abutting member 92 is fixedly provided in the accommodation unit 620 at a position that is outwardly away from the rotation axis 65A. The electric cable 90 enters the accommodation unit 620 from the end 90a, abuts on the outer peripheral surface of the abutting member 92, is bent, and is spirally wound.

In the X-ray imaging apparatus 10, the turning arm 62 rotates when, for example, the X-ray imaging (the CT imaging or the panoramic imaging) is executed. In the state in which the turning arm 62 starts to rotate, the spiral of the electric cable 90 is loosened as illustrated in FIG. 32. As the turning arm 62 rotates, the electric cable 90 is wound as illustrated in FIGS. 33 and 34. Upon completion of the X-ray imaging, the turning arm 62 returns to the rotation start position, whereby the spiral of the electric cable 90 is returned to the loosened state as illustrated in FIG. 32.

In this way, the turning arm 62 (support) rotates in the opposite direction to the winding direction of the spiral of the electric cable 90 with respect to the upper frame 64 (bracket). Consequently, shortage of the electric cable 90 can be prevented. The electric cable 90 is wound into the spiral shape when the turning arm 62 returns to the initial position, so that the surplus portion of the electric cable 90 can be prevented from obstructing the rotation of the turning arm 62.

The electric cable 90 is bent along the abutting member 92, so that a curvature radius of the bending of the electrical cable 90 can be set larger as compared with that case that the abutting member 92 is absent. Consequently, tension applied to the electric cable 90 can be reduced, and disconnection of the wire cable can be prevented. The abutting member 92 is preferably a cylindrical member, but may be a plate member in which a curved surface is formed only at the abutting portion.

2. Second Preferred Embodiment

Figure 35:
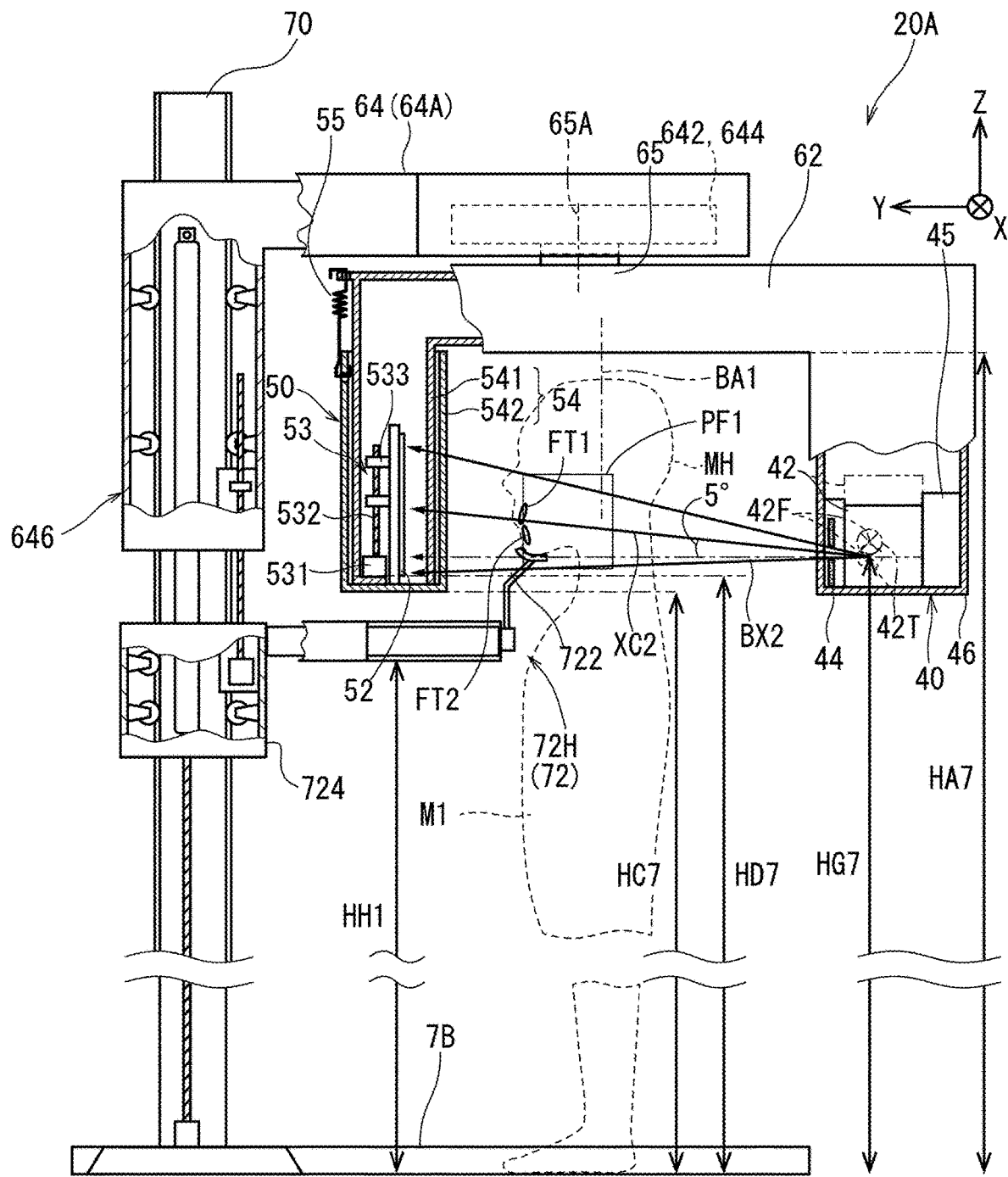
FIG. 35 is a view illustrating an imaging unit 20A according to a second preferred embodiment.

FIG. 35 is a view illustrating an imaging unit 20A according to a second preferred embodiment. FIG. 35 is a side view illustrating the imaging unit 20A that executes the entire jaw panoramic section PF1. It is assumed that the entire jaw panoramic section PF1 in FIG. 35 is set at the same position as the entire jaw panoramic section PF1 in FIG. 26, namely, the height position including the tip of the jaw.

The imaging unit 20A of the second preferred embodiment has substantially the same configuration as the imaging unit 20 except that the imaging unit 20A includes an X-ray generator vertical movement driving unit 45. The X-ray generator vertical movement driving unit 45 is provided in the casing 46. The X-ray generator vertical movement driving unit 45 integrally moves the X-ray generator 42 and the X-ray beam shape adjuster 44 in the vertical direction (Z-axis direction) with respect to the turning arm 62. The X-ray generator vertical movement driving unit 45 may be constructed with a ball screw mechanism or a linear motor mechanism. The X-ray generator vertical movement drive unit 45 is controlled by the X-ray generating unit drive controller 806. As illustrated in FIG. 35, for the imaging unit 20A, the X-ray tube 42T and the focal point 42F are vertically moved when the X-ray generator vertical movement driving unit 45 vertically moves the X-ray generator 42.

At this point, as illustrated in FIG. 35, the height of each element of the imaging unit 20A in performing the panoramic imaging of the entire jaw panoramic section PF1 is compared with the height of each element of the imaging unit 20 of the first preferred embodiment in imaging the entire jaw panoramic section PF1 at the same position. The entire jaw panoramic section PF1 is irradiated while the X-ray beam is shot up with a shooting-up angle of 5°, so that a height HG7 of the X-ray generator 42 (in particular, the focal point 42F) in the imaging unit 20A is set identical to the height HG5 in the imaging unit 20. On the other hand, in the imaging unit 20A, a height HA7 of the bottom surface of the turning arm 62 can be set higher than the height HA5 of the bottom surface of the turning arm 62 in the imaging unit 20 during the entire jaw panoramic mode in FIG. 26. Consequently, a height HC7 of the bottom surface of the casing 54 and a height HD7 of the bottom surface of the X-ray detector 52 can be set higher than the height HC5 of the bottom surface of the casing 54 and the height HD5 of the X-ray detector 52 in the entire jaw panoramic mode in FIG. 26. Thus, the X-ray detecting unit 50 can smoothly be turned around the subject M1.

Although the invention has been described in detail, the above description is illustrative in all aspects, but the invention is not limited thereto. Innumerable modifications not illustrated can be envisaged without departing from the scope of the present invention. The respective configurations described in the above preferred embodiments and modifications can appropriately be combined or omitted as long as they are inconsistent each other.

While the invention has been shown and described in detail, the foregoing description is in all aspects illustrative and not restrictive. It is therefore understood that numerous modifications and variations can be devised without departing from the scope of the invention.

What is claimed is:

1. An X-ray imaging apparatus comprising:
an X-ray generator;
an X-ray detector;
a support that supports said X-ray generator and said X-ray detector such that said X-ray generator and said X-ray detector oppose each other;
a turning motor that turns said X-ray generator and said X-ray detector supported by said support about a rotation shaft of said support;
a driving motor that moves said shaft;
a head holder that holds a head of a subject;
a shield that regulates a spread of an X-ray beam emitted from the X-ray generator; and
a processor configured to:
receive a selection of a mode among a plurality of modes including a panoramic mode in which a curved section corresponding to a dental arch is imaged and a CT mode in which a predetermined imaging region is imaged; and
adjust a shape of the X-ray beam emitted from said X-ray generator with said shield according to the selection of the mode received by the processor,
wherein
the processor is further configured to adjust the shape of said X-ray beam to shape the X-ray beam into an X-ray cone beam in which a center beam that is a center of the X-ray beam is incident orthogonally to a body axis of said head in said CT mode,
the processor is further configured to adjust the shape of said X-ray beam to shape the X-ray beam into an X-ray narrow beam in which a center beam that is a center of the X-ray beam is incident upward from obliquely downward with respect to said body axis, said X-ray narrow beam having a length in a direction of said body axis, in said panoramic mode,
said driving motor changes a magnification ratio by moving said X-ray detector with respect to said head held by said head holder, and
said drive motor decreases the magnification ratio in said panoramic mode as compared with the magnification ratio in said CT mode.

2. The X-ray imaging apparatus according to claim 1, wherein an SID that is an interval between a generation point of said X-ray beam in said X-ray generator and a detection surface of said X-ray beam in said X-ray detector is 500 mm or more and 900 mm or less.

3. The X-ray imaging apparatus according to claim 1, wherein
said turning motor rotates said support about a rotation axis line parallel to a vertical direction,
said processor adjusts the shape of said X-ray beam to shape the X-ray beam into said X-ray cone beam in which said center beam is incident in parallel to a horizontal direction in said CT mode, and
said processor adjusts the shape of said X-ray beam to shape the X-ray beam into said X-ray narrow beam in which said center beam is incident upward from obliquely downward with respect to the horizontal direction in said panoramic mode.

4. The X-ray imaging apparatus according to claim 3, further comprising:

a support post rising in said vertical direction; and
a vertical movement driving motor that independently and vertically moves said support and said head holder along said support post.

5. The X-ray imaging apparatus according to claim 4, wherein said vertical movement driving motor positions said support in said CT mode higher vertically than said support in said panoramic mode.

6. The X-ray imaging apparatus according to claim 1, wherein said CT mode includes a first mode in which said turning motor rotates said X-ray generator and said X-ray detector by 360 degrees and a second mode in which said turning motor rotates said X-ray generator and said X-ray detector by 180 degrees.

7. An X-ray imaging apparatus comprising:
an X-ray generator;
an X-ray detector;
a support that supports said X-ray generator and said X-ray detector such that said X-ray generator and said X-ray detector oppose each other;
a turning motor that turns said X-ray generator and said X-ray detector supported by said support;
a head holder that holds a head of a subject;
a shield that regulates a spread of an X-ray beam emitted from the X-ray generator; and
a processor configured to:
receive selection of a mode among a plurality of modes including a panoramic mode in which a curved section corresponding to a dental arch is imaged and a CT mode in which a predetermined imaging region is imaged; and
adjust a shape of said X-ray beam emitted from said X-ray generator according to the selection of the mode received by the processor,
wherein
the processor is further configured to adjust the shape of said X-ray beam to shape the X-ray beam into an X-ray cone beam in which a center beam that is a center of the X-ray beam is incident orthogonally to a body axis of said head in said CT mode,
the processor is further configured to adjust the shape of said X-ray beam to shape the X-ray beam into an X-ray narrow beam in which a center beam that is a center of the X-ray beam is incident upward from obliquely downward with respect to said body axis, said X-ray narrow beam having a length in a direction of said body axis, in said panoramic mode,
said turning motor rotates said support about a rotation axis line parallel to a vertical direction,
said processor adjusts the shape of said X-ray beam to shape the X-ray beam into said X-ray cone beam in which said center beam is incident in parallel to a horizontal direction in said CT mode,
said processor adjusts the shape of said X-ray beam to shape the X-ray beam into said X-ray narrow beam in which said center beam is incident upward from obliquely downward with respect to the horizontal direction in said panoramic mode, and
$hb=(SID/m)\tan\theta$ and $15<hb<65$ is satisfied with respect to said X-ray narrow beam formed in said panoramic mode, where said curved section imaged in panoramic mode is a panoramic section, hb is a distance between a point on said panoramic section through which said center beam extends and a point on said panoramic section through which a horizontal line extends from an generation point of said X-ray narrow beam, SID is an interval between said generation point of said X-ray beam in said X-ray generator and a detection surface of said X-ray beam in said X-ray detector, m is a magnification ratio, and θ is an angle formed between said center beam and the horizontal line.

8. The X-ray imaging apparatus according to claim 7, wherein said plurality of modes include an entire jaw panoramic mode in which an entire jaw is set to be an imaging object and a partial panoramic mode in which a part of said entire jaw is set to be the imaging object.

9. The X-ray imaging apparatus according to claim 7, further comprising an X-ray detector vertical movement driving motor that vertically moves said X-ray detector with respect to said support, wherein
said CT mode includes a large irradiation field CT mode having a relatively large imaging region and a small irradiation field CT mode having a relatively small imaging region, and
said X-ray detector vertical movement driving motor lowers said X-ray detector in said large irradiation field CT mode as compared with said small irradiation field CT mode.

10. The X-ray imaging apparatus according to claim 7, further comprising:
a support post rising in said vertical direction; and
a vertical movement driving motor that independently and vertically moves said support and said head holder along said support post.

11. The X-ray imaging apparatus according to claim 10, wherein said vertical movement driving motor positions said support in said CT mode higher vertically than said support in said panoramic mode.

12. The X-ray imaging apparatus according to claim 7, wherein said CT mode includes a first mode in which turning motor rotates said X-ray generator and said X-ray detector by 360 degrees and a second mode in which said turning motor rotates said X-ray generator and said X-ray detector by 180 degrees.

13. The X-ray imaging apparatus according to claim 7, wherein an SID that is an interval between a generation point of said X-ray beam in said X-ray generator and a detection surface of said X-ray beam in said X-ray detector is 500 mm or more and 900 mm or less.

14. The X-ray imaging apparatus according to claim 7, further comprising:
a bracket that suspends and supports said support;
a vertical movement driving motor vertically moves said bracket;
an arm extending horizontally from said bracket; and
a head fixture for a cephalometric imaging that is provided at a distal end of said arm to fix the head.

15. An X-ray imaging method comprising:
holding a head of a subject with a head holder;
turning around said head an X-ray generator and an X-ray detector that are supported by a support such that said X-ray generator and said X-ray detector oppose each other;
detecting an X-ray beam emitted from said X-ray generator using said X-ray detector;
receiving a selected mode from a plurality of modes including a panoramic mode in which a curved section corresponding to a dental arch is imaged and a CT mode in which a predetermined imaging region is imaged; and
adjusting a shape of the X-ray beam emitted from said X-ray generator by a shield according to the mode of which the selection is received, said shield regulates a spread of the X-ray beam emitted from the X-ray generator,
wherein
said X-ray beam forms an X-ray cone beam in which a center beam that is a center of the X-ray beam is incident orthogonally to a body axis of said head in said CT mode,
said adjusting the shape of the X-ray beam forms an X-ray narrow beam in which a center beam that is a center of the X-ray beam is incident upward from obliquely downward with respect to said body axis, said X-ray narrow beam having a length in a direction of said body axis, in said panoramic mode,
a magnification ratio is changed by moving said X-ray detector with respect to said head held by said head holder, and
the magnification ratio is decreased in said panoramic mode as compared with the magnification ratio in said CT mode.

16. The X-ray imaging method according to claim 15, further comprising:
rotating said support about a rotation axis line parallel to a vertical direction,
shaping the X-ray beam into said X-ray cone beam in which said center beam is incident in parallel to a horizontal direction in said CT mode, and
shaping the X-ray beam into said X-ray narrow beam in which said center beam is incident upward from obliquely downward with respect to the horizontal direction in said panoramic mode.

17. The X-ray imaging method according to claim 16, further comprising:
independently and vertically moving said support along a support post rising in said vertical direction and said head holder along said support post.

18. The X-ray imaging method according to claim 17, further comprising:
vertically moving said support in said CT mode onto a vertically upper side than said support in said panoramic mode.

19. An X-ray imaging method comprising:
holding a head of a subject with a head holder;
turning around said head an X-ray generator and an X-ray detector that are supported by a support such that said X-ray generator and said X-ray detector oppose each other;
detecting an X-ray beam emitted from said X-ray generator using said X-ray detector;
receiving a selected mode from a plurality of modes including a panoramic mode in which a curved section corresponding to a dental arch is imaged and a CT mode in which a predetermined imaging region is imaged; and
adjusting a shape of the X-ray beam emitted from said X-ray generator by a shield according to the mode of which the selection is received, said shield regulates a spread of the X-ray beam emitted from the X-ray generator,
wherein
said X-ray beam forms an X-ray cone beam in which a center beam that is a center of the X-ray beam is incident orthogonally to a body axis of said head in said CT mode, and
said adjusting the shape of the X-ray beam forms an X-ray narrow beam in which a center beam that is a center of the X-ray beam is incident upward from obliquely downward with respect to said body axis, said X-ray narrow beam having a length in a direction of said body axis, in said panoramic mode, said turning around said head the X-ray generator and the X-ray detector rotates said support about a rotation axis line parallel to a vertical direction, said adjusting the shape of the X-ray beam shapes the X-ray beam into said X-ray cone beam in which said center beam is incident in parallel to a horizontal direction in said CT mode, said adjusting the shape of the X-ray beam shapes the X-ray beam into said X-ray narrow beam in which said center beam is incident upward from obliquely downward with respect to the horizontal direction in said panoramic mode, and $hb=(SID/m)\tan\theta$ and $15<hb<65$ is satisfied with respect to said X-ray narrow beam formed in said panoramic mode, where said curved section imaged in panoramic mode is a panoramic section, hb is a distance between a point on said panoramic section through which said center beam extends and a point on said panoramic section through which a horizontal line extends from an generation point of said X-ray narrow beam, SID is an interval between said generation point of said X-ray beam in said X-ray generator and a detection surface of said X-ray beam in said X-ray detector, m is a magnification ratio, and $\theta$ is an angle formed between said center beam and the horizontal line.

20. The X-ray imaging method according to claim 19, further comprising: independently and vertically moving said support along a support post rising in said vertical direction and said head holder along said support post.

21. The X-ray imaging method according to claim 20, further comprising: vertically moving said support in said CT mode onto a vertically upper side than said support in said panoramic mode.

\* \* \* \* \*